(12) United States Patent
Jiang et al.

(10) Patent No.: US 11,357,806 B2
(45) Date of Patent: Jun. 14, 2022

(54) METHOD OF ISOLATING SPHINGOLIPIDS FROM CORDYCEPS AND THEIR USE

(71) Applicant: Macau University of Science and Technology, Taipa (MO)

(72) Inventors: Zhi-Hong Jiang, Taipa (MO); Jing-Rong Wang, Taipa (MO); Jia-Ning Mi, Taipa (MO); Junping Kou, Taipa (MO); Yuwei Han, Taipa (MO); Yingqiong Xu, Taipa (MO)

(73) Assignee: Macau University of Science and Technology, Taipa (MO)

( * ) Notice: Subject to any disclaimer, the term of this patent is extended or adjusted under 35 U.S.C. 154(b) by 858 days.

(21) Appl. No.: 15/131,218

(22) Filed: Apr. 18, 2016

(65) Prior Publication Data

US 2017/0128507 A1     May 11, 2017

Related U.S. Application Data

(60) Provisional application No. 62/251,195, filed on Nov. 5, 2015.

(51) Int. Cl.

| A61K 36/068 | (2006.01) |
|---|---|
| A61K 31/133 | (2006.01) |
| A61K 31/164 | (2006.01) |
| A61K 31/688 | (2006.01) |
| G01N 30/34 | (2006.01) |
| G01N 30/72 | (2006.01) |
| B01D 15/42 | (2006.01) |
| C12Q 1/04 | (2006.01) |
| G01N 33/92 | (2006.01) |
| G01N 30/00 | (2006.01) |
| G01N 30/02 | (2006.01) |

(52) U.S. Cl.
CPC ......... *A61K 36/068* (2013.01); *A61K 31/133* (2013.01); *A61K 31/164* (2013.01); *A61K 31/688* (2013.01); *B01D 15/426* (2013.01); *C12Q 1/04* (2013.01); *G01N 30/34* (2013.01); *G01N 30/72* (2013.01); *G01N 30/7233* (2013.01); *G01N 33/92* (2013.01); *A61K 2236/333* (2013.01); *A61K 2236/39* (2013.01); *A61K 2236/50* (2013.01); *A61K 2236/53* (2013.01); *G01N 2030/009* (2013.01); *G01N 2030/027* (2013.01); *G01N 2333/37* (2013.01); *G01N 2405/08* (2013.01)

(58) Field of Classification Search
CPC ........................... A61K 36/068; A61K 31/133
See application file for complete search history.

(56) References Cited

U.S. PATENT DOCUMENTS

| 7,597,899 B2 * | 10/2009 | Lambers | A61K 8/41 |
|---|---|---|---|
| | | | 424/401 |
| 2003/0095982 A1 * | 5/2003 | Lin | A61K 36/068 |
| | | | 424/195.15 |

FOREIGN PATENT DOCUMENTS

FR          2820037 A1 *  8/2002  ........... A61K 9/0014

OTHER PUBLICATIONS

Type 1 diabetes from Mayo Clinic. Retrieved from the interneton: Jul. 18, 2020. Retrieved from: <URL: https://www.mayoclinic.org/diseases-conditions/type-1-diabetes/diagnosis-treatment/drc-20353017?p=1>. 13 pages. (Year: 2020).*
Celiac Disease from Mayo Clinic. Retrieved from the Interneton: Jul. 18, 2020. Retrieved from: <URL: https://www.mayoclinic.org/diseases-conditions/celiac-disease/diagnosis-treatment/drc-20352225?p=1>. 4 pages. (Year: 2020).*
Lupus from Mayo Clinic. Retrieved from the Interneton: Jul. 18, 2020. Retrieved from: <URL: https://www.mayoclinic.org/diseases-conditions/lupus/diagnosis-treatment/drc-20365790?p=1>. 7 pages. (Year: 2020).*
Hay Fever from Mayo Clinic. Retrieved from the Interneton: Jul. 18, 2020. Retrieved from: <URL: https://www.mayoclinic.org/diseases-conditions/hay-fever/diagnosis-treatment/drc-20373045?p=1>. 4 pages. (Year: 2020).*
(U1) Eczema from Mayo Clinic. Retrieved from the Interneton: Jul. 18, 2020. Retrieved from: <URL: https://www.mayoclinic.org/diseases-conditions/atopic-dermatitis-eczema/diagnosis-treatment/drc-20353279?p=1>. 6 pages. (Year: 2020).*
G. S. Bondy et al. (2000) "Immunomodulation by Fungal Toxins", Journal of Toxicology and Environmental Health, Part B, 3:2, 109-143, DOI: 10.1080/109374000281113.

(Continued)

*Primary Examiner* — Amy L Clark
(74) *Attorney, Agent, or Firm* — Renner Kenner Greive Bobak Taylor & Weber

(57) ABSTRACT

A method of isolating at least one sphingolipid portion selected from a sphingoid base portion, a ceramide portion, a glycosphingolipid portion or a phosphosphingolipid portion from *Cordyceps*, in particular from wild-type *Cordyceps*, allows for obtaining sphingolipid portions having an increased amount of one of sphingoid bases, ceramides, glycosphingolipids or phosphosphingolipids. The sphingolipid portions isolated contained significant amounts of sphingolipids not reported so far, and possess exceptional immunosuppressive activities. A method of treating a subject suffering from an inflammatory disease like an autoimmune disease or an allergic disease includes administering sphingolipids isolated from *Cordyceps*, in particular from wild-type *Cordyceps*. A method of treating a subject suffering from an inflammatory disease includes administering certain sphingolipids to the subject. Still further in accordance with the present invention is a composition, in particular a pharmaceutical composition comprising at least one sphingolipid portion.

5 Claims, 19 Drawing Sheets

(56) References Cited

OTHER PUBLICATIONS

S. C. Diesner et al., "Perspectives on Immunomodulation Early in Life", Pediatr. Allergy Immunol. 2012, 23, pp. 210-223.

T. H. Beckham et al., "Interdiction of Sphingolipid Metabolism to Improve Standard Cancer Therapies", Adv. Cancer Res. 2013, vol. 117, pp. 1-36.

A. Delgado et al., "Natural Products as Platforms for the Design of Sphingolipid-Related Anticancer Agents", Adv. Cancer Res. 2013, vol. 117, pp. 237-281.

The Pharmacopoeia Commission of PRC (Eds.), "Cordyceps", Pharmacopoeia of the People's Republic of China, Chemical Industry Publishing House, Beijing, 2010.

X. Zhou et al., "Cordyceps Fungi: Natural Products, Pharmacological Functions and Developmental Products", J. Pharm. Pharmacol. 2009, vol. 61, pp. 279-291.

T. Fujita et al., "Fungal Metabolites. Part II. A Potent Immunosuppressive Activity Found in Isaria Sinclairii Metabolite", J. Antibiotics, Feb. 1994, vol. 47, No. 2, pp. 208-215.

J. R. Wang et al., "Improved Sphingolipidomic Approach Based on Ultra-High Performance Liquid Chromatography and Multiple Mass Spectrometries with Application to Cellular Neurotoxicity", Anal. Chem., 2014, vol. 86, pp. 5688-5696.

J. N. MI et al., "Quantitative Profiling of Sphingolipids in Wild Cordyceps and its Mycelia by Using UHPLC-MS", Sci. Rep. 2016,6, 20870. DOI: 10.1038/srep20870.

X. L. Guan et al., "Biochemical Membrane Lipidomics During *Drosophila* Development", Developmental Cell, 2013, vol. 24, pp. 98-111.

N. C. Zitomer et al., "Ceramide Synthase Inhibition by Fumonisin B1 Causes Accumulation of 1-Deoxysphinganine", J. Biol. Chem. 2009, vol. 284, No. 8, pp. 4786-4795.

F. B. Jungalwala et al., "High Performance Chromatography-Chemical Ionization Mass Spectrometry of Sphingoid Bases Using Moving-Belt Interface", J. Lipid Res., 1984, vol. 25, No. 2, pp. 209-216.

A. H. Merrill Jr., "Sphingolipid and Glycosphingolipid Metabolic Pathways in the Era of Sphingolipidomics", Chem. Rev., 2011, vol. 111, pp. 6387-6422.

A. Penno et al., "Hereditary Sensory Neuropathy Type 1 is Caused by the Accumulation of Two Neurotoxic Sphingolipids", J. Biol. Chem., 2010, vol. 285, No. 15, pp. 11178-11187.

R. Tkindt et al., "Profiling and Characterizing Skin Ceramides Using Reversed-Phase Liquid Chromatography-Quadrupole Time-of-Flight Mass Spectrometry", Anal. Chem., 2012, vol. 84, pp. 403-411.

M. Valsecchi et al., Ceramides as Possible Nutraceutical Compounds: Characterization of the Ceramides of the Moro Blood Orange (Citrus Sinensis), J. Agric. Food Chem., 2012, vol. 60, pp. 10103-10110.

D. A. Penalva et al., "Atypical Surface Behavior of Ceramides with Nonhydroxy and 2-Hydroxy Very Long-Chain (C28-C32) PUFAs", Biochem. Biophys. Acta., 2014, vol. 1838, pp. 731-738.

G. Yang et al., "Suppression of Splenic Lymphocyte Proliferation by Eucommia Ulmoides and Genipin", Chem. Biodivers., 2015, vol. 12, p. 538.

* cited by examiner

METHOD OF ISOLATING SPHINGOLIPIDS FROM CORDYCEPS AND THEIR USE

TECHNICAL FIELD

The present invention relates to a method of isolating at least one sphingolipid portion selected from a sphingoid base portion, a ceramide portion, a glycosphingolipid portion or a phosphosphingolipid portion from *Cordyceps*, in particular from wild-type *Cordyceps*. In a further aspect, the present invention relates to a method of treating a subject suffering from an inflammatory disease like an autoimmune disease or an allergic disease by administering sphingolipids isolated from *Cordyceps*, in particular from wild-type *Cordyceps*. In accordance with the invention is also a method of treating a subject suffering from an inflammatory disease by administering certain sphingolipids to the subject. Still further in accordance with the present invention is a composition, in particular a pharmaceutical composition comprising at least one sphingolipid portion.

BACKGROUND OF THE INVENTION

Inflammatory or immune diseases, i.e. diseases resulting from an aberrant immune response, are among leading causes of death. Unfortunately, there seems to be a steady and rapid increase of autoimmune diseases as well as of allergic diseases over the last decades. Autoimmune diseases can affect, for example, the skin (e.g. psoriasis), the joints (e.g. rheumatoid arthritis), the nervous system (e.g. multiple sclerosis), the gut (e.g. ulcerative colitis and Crohn's disease) and the endocrine system (e.g. type 1 diabetes and thyroid disease). The incidence rates vary among the respective autoimmune diseases and seem to depend on several environmental factors. Prominent and severe allergic diseases include respiratory diseases like bronchial asthma and chronic obstructive pulmonary diseases (COPD).

Conventional therapies for treatment of autoimmune diseases or inflammatory diseases usually include the administration of steroids, which treatment is however often accompanied by adverse events and several contraindications or interactions with further drugs need to be considered. Long-term treatment with steroids is, moreover, not to be recommended.

Thus, there is still a need for therapeutically effective compounds and improved ways for successfully treating such diseases. As usual, it is generally desirable to have compounds with reduced risk for side effects, which can be prepared in a cost-effective way.

Recently, Traditional Chinese medicine as well as complementary and alternative medicine has getting popular providing a lot of treatment options. Traditional Chinese medicines based on plant materials as well as plants or respective components gained from plants usually allow for treatment of various diseases and conditions while bearing a reduced risk for side effects. In view of the rich medicinal plant resources, available respective medicines can usually be produced in a cost-effective way. Accordingly, there has been a lot of research with regard to plants and respective ingredients for treatment of several diseases and conditions.

For example, *Cordyceps* is a famous traditional Chinese medicinal material owing to its various therapeutic effects and a broad spectrum of pharmacological activities, respectively. Wild-type *Cordyceps* is a composite consisting of a stroma of a fungus that grows on a dead caterpillar whose larva is the primary host of the fungus, which is also known as caterpillar fungus. More specifically, wild-type *Cordyceps* grows in a natural environment and mainly consists of stroma of *Cordyceps sinensis* [Berk.] Sacc. (family Hypocreaceae) and a dead caterpillar of *Hepialus armoricanus* (family Hepialidae). Further, several products based on fungi or mycelia isolated from wild-type *Cordyceps* and being artificially cultured have been developed and manufactured in large quantities in particular by using fermentation technology. Five of such *Cordyceps* derivates have been approved so far as drugs by the China Food and Drug Administration (CFDA), comprising *Cordyceps sinensis*, *Hirsutella sinensis*, *Cephalosporium sinensis*, *Mortierella SP* and *Gliocadium roseum*.

In 1994, myriocin, a natural sphingolipid was isolated from the culture broth of *Isaria sinclairii* (the imperfect stage of *Cordyceps sinclairii*) as a potent immunosuppressive constituent. Starting from myriocin, FTY720 was synthesized and finally developed into a drug (Fingolimod) for the treatment of multiple sclerosis and organ transplantation. Thus, sphingolipids might be active constituents of *Cordyceps* and respective derivates.

The specific structure of the constituents of *Cordyceps*, in particular of wild-type *Cordyceps*, is not completely known and the number of reports dealing with an isolation and identification of sphingolipids from *Cordyceps* is limited. Before the discovery of myriocin, there was almost no report on sphingolipids from wild-type *Cordyceps*. Basically, since diversified components in Chinese herbal medicines often act via multiple modes, there is a strong need for identifying and providing components in isolated form with sufficient therapeutic efficiency. Having those active ingredients in isolated form could further reduce the risk of side effects or interactions which might limit the therapeutic use due to the presence of further ingredients with reduced or insufficient efficacy for treating the respective disease. And although available data suggest that natural sphingolipids are generally pharmacologically active constituents of several natural medicines, there remain challenges in isolating and identifying sphingolipids in natural materials.

Accordingly, there remains a need for methods which allow for isolating and identifying components such as from wild-type *Cordyceps* with sufficient therapeutic efficacy.

SUMMARY OF THE INVENTION

The present invention refers in a first aspect to a method of isolating at least one sphingolipid portion from *Cordyceps*, in particular from wild-type *Cordyceps*, selected from a sphingoid base portion, a ceramide portion, a glycosphingolipid portion or a phosphosphingolipid portion. The method comprises steps of:

(i) subjecting a *Cordyceps* material to a solvent extraction with at least a first and a second extracting solvent in order to obtain a sphingolipid crude extract, wherein the first and the second extracting solvent independently comprise an aliphatic alcohol and a halogenated hydrocarbon; and (ii) subjecting the sphingolipid crude extract to at least a first and a second chromatographic separation step for obtaining the sphingolipid portion, which first chromatographic separation step includes liquid chromatography with a stationary phase comprising an unmodified silica and which second chromatographic separation step includes liquid chromatography with a stationary phase comprising silica modified with polar functional groups.

The method preferably further comprises steps of:

(iii) subjecting the at least one sphingolipid portion to liquid chromatography with a mobile phase comprising at least a first and a second eluting solvent, wherein the at least first and second eluting solvent comprise a mixture of at least one aliphatic alcohol, at least one carboxylic acid and at least one carboxylic acid salt and wherein the second eluting solvent has a higher total amount of aliphatic alcohol compared to the first eluting solvent; and (iv) performing a mass spectrometry following step (iii).

In particular LC-MS, most preferably coupled UHPLC-Q-TOF MS is applied in step (iii) and step (iv).

Further in accordance with the present invention is a composition, preferably a pharmaceutical composition comprising and in particular essentially consisting of:

at least one sphingolipid portion, in particular one sphingolipid portion, in particular as pharmaceutically effective ingredients, isolated from *Cordyceps* according to the method described above, and at least one pharmaceutically tolerable excipient such as one or more of a diluent, a filler, a binder, a disintegrant, a lubricant, a coloring agent, a surfactant and a preservative.

In another aspect, the present invention refers to a method of treating a subject such as a mammal suffering from an inflammatory disease, in particular an autoimmune disease or an allergic disease. The method comprises administering an effective amount of at least one sphingolipid portion to the subject, which sphingolipid portion is selected from a sphingoid base portion, a ceramide portion, a glycosphingolipid portion or a phosphosphingolipid portion isolated from *Cordyceps* according to the method described above. In particular, the sphingolipid portion is the sphingoid base portion.

In still another aspect, the present invention refers to a method of treating a subject, preferably a human, suffering from an inflammatory disease, in particular an autoimmune disease or an allergic disease. The method comprises administering an effective amount of sphingoid base sphingolipids to the subject, which sphingoid base sphingolipids comprise:

So (d18:5) having the following Formula (3) with x=1 and y=2:

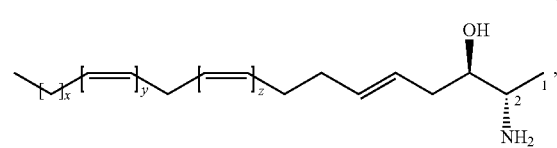

Formula (3)

So(d20:3) having Formula (3) as given above with x=7 and y=0,
So(d22:5) having Formula (3) as given above with x=5 and y=2,
So(t15:2) having Formula (4) with x=4 and y=0:

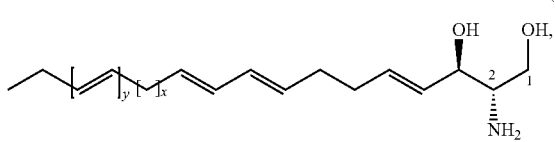

Formula (4)

So(t15:3) having Formula (4) as given above with x=2 and y=1,
So(t19:2) having Formula (4) as given above with x=8 and y=0, So(t21:3) having Formula (4) as given above with x=8 and y=1,
So(t21:4) having Formula (4) as given above with x=6 and y=2,
So(m22:1) having Formula (5) with x=12, y=0 and z=0:

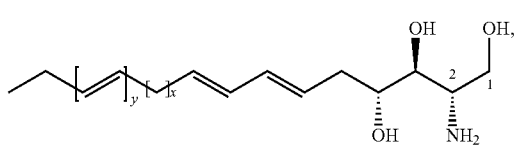

Formula (5)

So(m22:2) having Formula (5) as given above with x=10, y=0 and z=1, and
So(m22:3) having Formula (5) as given above with x=8, y=1 and z=1.

Another aspect of the present invention relates to a method of treating an inflammatory disease comprising:

isolating at least one sphingolipid portion from *Cordyceps* by the method described above, in particular selected from a sphingoid base portion, a ceramide portion or a glycosphingolipid portion, further preferably a sphingoid base portion; and formulating the sphingolipid portion into a pharmaceutical composition; and administering said pharmaceutical composition to a subject suffering from an inflammatory disease. The subject is preferably a mammal such as a human.

The present invention based on the extraction, in particular the extraction with extracting solvents comprising an aliphatic alcohol and a halogenated hydrocarbon accompanied by a sequential chromatographic enrichment with an unmodified followed by a modified polar silica phase, allows for isolating sphingolipid portions from *Cordyceps*, namely for obtaining sphingolipid portions having an increased amount of one of sphingoid bases, ceramides, glycosphingolipids or phosphosphingolipids, wherein the sphingolipid portions isolated proved to have exceptional immunosuppressive activities. The results of immunosuppressive activity tests in particular demonstrated that the sphingoid base sphingolipid portion exhibits the most potent immunosuppressive activity.

The method of the present invention for isolating at least one sphingolipid portion from *Cordyceps* further allowed for the isolation of about 275 sphingolipids including 12 sphingoid bases, 159 ceramides, 65 glycosphingolipids and 39 sphingomyelins which have not been reported so far. The number of novel sphingolipids accounts for more than 50% of the total number of isolated and identified sphingolipids in *Cordyceps*, showing an enormous potential of this material as a resource of pharmacologically-active sphingolipids, in particular immunosuppressive sphingolipids. Besides, *Cordyceps* sphingolipids with great structural diversity not reported so far could be identified with the method of the present invention.

BRIEF DESCRIPTION OF DRAWINGS

FIGS. 13A and 13B show MS/MS spectra of ceramides isolated from wild-type *Cordyceps* material and the corresponding sphingolipid standards, wherein FIG. 13A shows MS/MS spectra of Cer (d18:1/16:0), Cer (d18:0/16:0), Cer (d14:0/22:1), Cer (d14:1/22:0), Cer (d14:0/22:0), Cer (d18:1/22:0), Cer (d18:0/22:0), Cer (d18:1/24:1) and Cer (d18:0/24:1) isolated from wild-type *Cordyceps* and compares these spectra with that of the corresponding sphingolipid standards, and FIG. 13B shows MS/MS spectra of Cer (d18:1/24:0), Cer (d18:0/24:0), Cer (d18:1/24:0(OH)), Cer (t18:0/24:0) and Cer (t18:0/24:0(OH)) isolated from wild-type *Cordyceps* material and compares these spectra with that of the corresponding sphingolipid standards.

FIGS. 14A and 14B show MS/MS spectra of sphingomyelins isolated from wild-type *Cordyceps* material and the corresponding sphingolipid standards, wherein FIG. 14A shows MS/MS spectra of SM (d30:1), SM (d30:0), SM (d14:1/20:0), SM (d14:0/20.0), SM (d15:1/20.0), SM (d35:0), SM (d14:1/22:0), SM (d36:0) and SM (d14:1/24:0) isolated from wild-type *Cordyceps* material and compares these spectra with that of the corresponding sphingolipid standards, and FIG. 14B shows MS/MS spectra of SM (d38:0), SM (d18:1/22:0), SM (d40:0), SM (d42:1) and SM (d42:0) isolated from wild-type *Cordyceps* material and compares these spectra with that of the corresponding sphingolipid standards.

FIG. 16A shows the effect of FTY720 on the proliferation inhibition ratio in LPS-induced splenic lymphocytes. FIG. 16B shows the effect of the sphingoid base portion isolated from wild-type *Cordyceps* on the proliferation inhibition ratio in LPS-induced splenic lymphocytes. FIG. 16C shows the effect of the ceramide portion isolated from wild-type *Cordyceps* on the proliferation inhibition ratio in LPS-induced splenic lymphocytes. FIG. 16D shows the effect of the glycosphingolipid portion isolated from wild-type *Cordyceps* on the proliferation inhibition ratio in LPS-induced splenic lymphocytes. FIG. 16E shows the effect of the sphingomyelin portion isolated from wild-type *Cordyceps* on the proliferation inhibition ratio in LPS-induced splenic lymphocytes.

FIG. 17A shows the effect of FTY720 on the proliferation inhibition ratio in Con A-induced splenic lymphocytes. FIG. 17B shows the effect of the sphingoid base portion isolated from wild-type *Cordyceps* on the proliferation inhibition ratio in Con A-induced splenic lymphocytes. FIG. 17C shows the effect of the ceramide portion isolated from wild-type *Cordyceps* on the proliferation inhibition ratio in Con A-induced splenic lymphocytes. FIG. 17D shows the effect of the glycosphingolipid portion isolated from wild-type *Cordyceps* on the proliferation inhibition ratio in Con A-induced splenic lymphocytes. FIG. 17E shows the effect of the sphingomyelin portion isolated from wild-type *Cordyceps* on the proliferation inhibition ratio in Con A-induced splenic lymphocytes.

DESCRIPTION OF THE INVENTION AND EMBODIMENTS

Figure 1A:
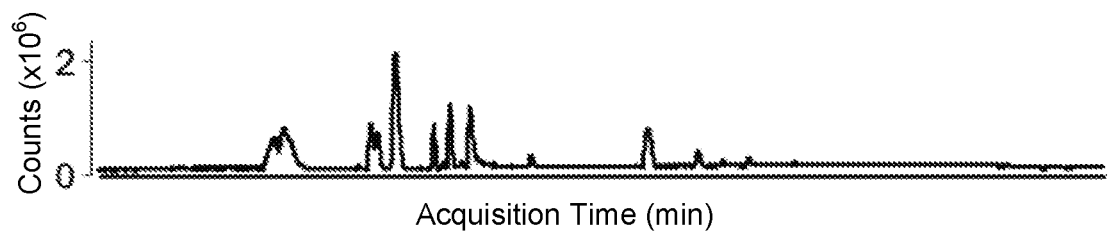
FIG. 1A shows a base peak chromatogram of a blank sample obtained with UHPLC-UHD iFunnel-Q-TOF MS after chromatographic separation.

The following embodiments and examples are given to enable those skilled in the art to more clearly understand and to practice the present invention. They should not be considered as limiting the scope of the invention, but merely as being illustrative and representing preferred embodiments thereof. The technical terms used in the present patent application have the meaning as commonly understood by a respective skilled person unless specifically defined otherwise.

As used herein and in the claims, "comprising" means including the following elements but not excluding others. "Essentially consisting of" means that the material consists of the respective element along with usually and unavoidable impurities such as side products and components usually resulting from the respective preparation or method for obtaining the material such as traces of further components. "Consisting of" means that the material is solely consist of, i.e. is formed by the respective element.

In one aspect, the present invention relates to a method of isolating at least one sphingolipid portion from *Cordyceps* selected from a sphingoid base portion, a ceramide portion, a glycosphingolipid portion or a phosphosphingolipid portion. The *Cordyceps* material is preferably of wild-type *Cordyceps*.

The term "*Cordyceps*" used herein includes wild-type *Cordyceps* as well as *Cordyceps* derivates. The term "wild-type *Cordyceps*" (or "wild *Cordyceps*") is used for the naturally available and grown form of *Cordyceps*, i.e. the naturally available parasitic complex of a *Cordyceps* fungus with a caterpillar, namely and in the meaning of the present invention of the species *Cordyceps sinensis* (also known as *Ophiocordyceps sinensis*) with a caterpillar. Basically, the fungus infects the underground larva of one particular species of moth, *Hepialus armoricanus* and occasionally other species, grows and gradually changes into a fruiting body.

The term "*Cordyceps* derivates" as used herein means fungi in particular mycelia derived from wild-type *Cordyceps* in particular obtained by artificial cultivation of mycelia isolated from wild-type *Cordyceps* such as respective anamorphs of wild-type *Cordyceps sinensis*. The artificial cultivation preferably includes several techniques such as fermentation technology like submerged fermentation *Cordyceps* derivates include the artificial mycelial strains approved as drugs by the CFDA and commonly sold referenced as *Cordyceps sinensis* such as available from Jiangxi Jiminkexin Pharmaceutical Co., Ltd., *Hirsutella sinensis* such as marketed by Hangzhou Zhongmei Huadong Pharmaceutical Co., Ltd., *Cephalosporium sinensis* such as available from Yunnan Baiyao Group Lijiang Pharmaceutical Co. Ltd., Shenyang Dongxin Pharmaceutical Co., Ltd., Hunan Kangerjia Pharmaceutical Co., Ltd., Guizhou Liangji Pharmaceutical Co., Ltd. and Jiangsu Shenhua Pharmaceutical Co., Ltd., *Mortierella SP* such as marketed by Hangzhou Tianyuan Pharmaceutical Co., Ltd. and Datong Liqun Pharmaceutical Co., Ltd. and *Gliocadium roseum* such as from Hebei Changtian Pharmaceutical Co., Ltd.

A *Cordyceps* material comprises and preferably consists of *Cordyceps*, namely wild-type *Cordyceps* or *Cordyceps* derivates. The *Cordyceps* material preferably comprises more than 80 wt.-%, further preferred more than 90 wt.-%, more preferably more than 95 wt.-% of wild-type *Cordyceps* based on the total weight of the *Cordyceps* material and in particular the *Cordyceps* material consists of either wild-type *Cordyceps* or of a *Cordyceps* derivate, preferably of wild-type *Cordyceps*.

The term "sphingolipids" as used herein and as known to a skilled person refers to a family of compounds with a common structural feature, namely a sphingoid base backbone that is synthesized from serine and long-chain fatty acyl-CoA, and then converted into one of the respective subgroups. Sphingolipids generally include four subgroups, namely sphingoid bases, ceramides, phosphosphingolipids and glycosphingolipids.

Sphingolipids are generally based on the structure of Formula (1) also referenced as sphingolipid basic structure:

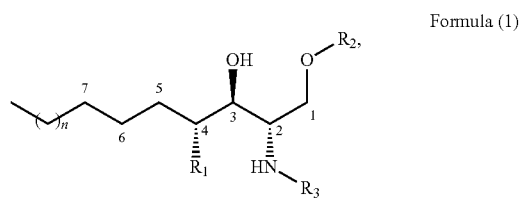

Formula (1)

The numbers 1 to 7 in Formula (1) indicate the position of the respective carbon atom in the carbon chain of the sphingolipid basic structure (i.e. without considering any carbon atoms in $R_2$ or $R_3$). $R_1$ is selected from —H or —OH. "d" meaning "dihydroxy base" in the respective sphingolipid name indicates that two hydroxyl groups are present, wherein "t" meaning "trihydroxy base" in the respective sphingolipid name indicates the presence of three hydroxyl groups. $R_2$ and $R_3$ vary depending on the specific subgroup of sphingolipids and, thus, determine the specific subgroup of sphingolipids. n is an integer and usually higher than 1. There are also sphingolipids in which the —OH group in the sphingolipid basic structure at carbon position 3 (C3) or 1 (C1) is missing, which embodiments are referenced with an "m". One or more than one double bond may optionally be present in the sphingolipid basic structure of Formula (1) (i.e. without considering possible double bonds in $R_2$ or $R_3$).

The subgroup of "sphingoid bases" generally includes, for example, sphingosines, sphinganines, sphingoid base-1-phosphate and lysosphingomyelin. For example, sphingosines (also abbreviated as "So") are based on the general structure of Formula (1), wherein $R_2$ and $R_3$ are —H and wherein at least one double bond is present in the sphingolipid basic structure of Formula (1). Sphinganines (also abbreviated as "Sa") are based on the general structure of Formula (1), wherein $R_2$ and $R_3$ are —H and wherein no double bond is present in the sphingolipid basic structure of Formula (1).

The subgroup of ceramides (also abbreviated as "Cer") as used herein refers to sphingoid bases with an amide-linked saturated or unsaturated fatty acid also named N-acyl-sphingoid bases and are based on the general structure of Formula (1), wherein $R_2$ is —H and wherein $R_3$ is a structure like the one of Formula (2):

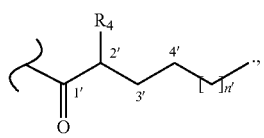

Formula (2)

wherein $R_4$ can be —H or —OH and wherein further —OH groups may be present in the structure of Formula (2). "d" indicates presence of two hydroxyl groups in $R_3$ and "t" of three hydroxyl groups. In embodiments, in which $R_4$ is —OH, this is indicated in the respective name of the compound used herein with a supplementary expression "(OH)". n' is an integer and usually above 1. One or more than one double bond may be present in the structure of Formula (2).

Phosphosphingolipids as a subgroup are complex sphingolipids with head groups that are attached via phosphodiester linkages and in particular include sphingomyelins, inositol phosphorylceramides and mannosylinositol phosphorylceramides. For example, sphingomyelins (also abbreviated as "SM") are based on the Formula (1) with $R_3$ being based on Formula (2), wherein $R_2$ is

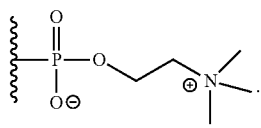 [SMILES: *P(=O)([O-])OCC[N+](C)(C)C]

Glycosphingolipids generally are complex sphingolipids with head groups that are attached via glycosidic bonds, like hexosyl (Hex-) and/or fucosyl (Fuc-) ceramides. For example, hexosyl ceramides (also abbreviated as "HexCer") are based on the Formula (1) with $R_3$ being based on Formula (2), wherein $R_2$ can be

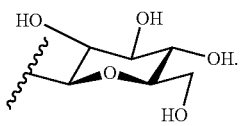

In sphingoid bases, the number of carbon atoms in Formula (1) as well as presence of double bonds and number thereof and whether $R_1$ is —H or —OH is evident from the respective name of the sphingolipid used herein and in accordance with the usual nomenclature used for sphingolipids. As an example of sphingoid bases, "So(d18:1)" means that a total of 18 carbon atoms are present in the sphingolipid basic structure of Formula (1) (i.e. without considering possible carbon atoms in $R_2$ or $R_3$) and that the number of double bonds in the sphingolipid basic structure of Formula (1) (i.e. without considering possible double bonds in $R_2$ or $R_3$) is 1. In case $R_1$ is —H, this is indicated with an initial "d" (dihydroxy base), wherein in case $R_1$ is —OH, this is evident from the initial letter "t".

For ceramides, phosphosphingolipids and glycosphingolipids, the same applies with regard to Formula (1) indicated in the name of the respective compound as first part within the brackets. In addition to the features of Formula (1), the names of those sphingolipids used herein in accordance with the usual nomenclature further include features of the Formula (2) as second part within the brackets after the slash, i.e. $R_3$, namely the number of carbon atoms in $R_3$ and kind of $R_4$ are evident from the respective name indicated. As an example, Cer (d18:1/18:2) means that the structure of Formula (1) indicated as first part within the brackets, i.e. "d18:1", has 18 carbon atoms and one double bond and is a dihydroxy base, i.e. $R_1$ is —H. As evident from the second part within the brackets, i.e. "18:2", $R_3$ has 18 carbon atoms and two double bonds and $R_4$ is —H. In Cer (d18:1/18:2 (OH)), $R_4$ is —OH.

The method of the present invention of isolating at least one sphingolipid portion comprises steps of:
(i) subjecting the *Cordyceps* material to a solvent extraction with at least a first and a second extracting solvent in order to obtain a sphingolipid crude extract, wherein the first and the second extracting solvent independently comprise an aliphatic alcohol and a halogenated hydrocarbon;
(ii) subjecting the sphingolipid crude extract to at least a first and a second chromatographic separation step for obtaining the sphingolipid portion, which first chromatographic separation step includes liquid chromatography with a stationary phase comprising an unmodified silica and which second chromatographic separation step includes liquid chromatography with a stationary phase comprising silica modified with polar functional groups.

The term "isolating" or "isolation" used herein means separating sphingoid bases, ceramides, glycosphingolipids or phosphosphingolipids like sphingomyelins in the *Cordyceps* material from 1) other non-sphingolipid components contained therein and 2) from other sphingolipid subgroups such that a sphingoid base portion, a ceramide portion, a glycosphingolipid portion or a phosphosphingolipid portion such as a sphingomyelin portion is obtained. The terms "sphingoid base portion", "ceramide portion", "glycosphingolipid portion" and "phosphosphingolipid portion" as used herein mean a portion rich in the respective subgroup, namely having an amount of the respective subgroup of sphingolipids of more than 50 wt.-%, preferably at least 70 wt.-% and more preferably of more than 80 wt.-% based on the weight of the respective sphingolipid portion. I.e. a sphingoid base portion comprises more than 50 wt.-%, preferably at least 70 wt.-% and more preferably more than 80 wt.-% of sphingoid bases based on the weight of the sphingoid base portion. Preferably, in step (i) a powdered *Cordyceps* material is used. Step (i) may, thus, further comprise pulverizing the *Cordyceps* material for obtaining a powdered *Cordyceps* material before step (i). For example, between 50 and 75 g, like 65 g of the *Cordyceps* material, in particular of the powdered *Cordyceps* material, can be subjected in step (i) to the solvent extraction.

In particular, the amount of *Cordyceps* material in relation to the total amount of the first extracting solvent is preferably between 10 mg/ml and 200 mg/ml, further preferred between 20 mg/ml and 150 mg/ml, in particular between 20 mg/ml and 50 mg/ml such as 25 mg/ml to 35 mg/ml and most preferably about 32.5 mg/ml *Cordyceps* material relative to the total amount of first extracting solvent used for extracting the *Cordyceps* material. The amount of *Cordyceps* material in relation to the total amount of the second extracting solvent is preferably between 10 mg/ml and 200 mg/ml, further preferred between 20 mg/ml and 150 mg/ml, in particular between 20 mg/ml and 50 mg/ml such as 25 mg/ml to 35 mg/ml and most preferably about 32.5 mg/ml *Cordyceps* material relative to the total amount of second extracting solvent used for extracting the *Cordyceps* material.

The first and the second extracting solvent in step (i) comprise an aliphatic alcohol, which means herein an aliphatic hydrocarbon, preferably a branched or straight chain alkane, wherein at least one hydrogen atom of the aliphatic hydrocarbon is substituted with a hydroxyl group, preferably one hydrogen atom is substituted with a hydroxyl group referenced as monohydric aliphatic alcohol. More preferably, the aliphatic alcohol of the first and second extracting solvent is preferably a monohydric aliphatic alcohol containing 1 to 4 carbon atoms, preferably an alkane with 1 to 4 carbon atoms with one hydrogen atom being replaced with a hydroxyl group. I.e. the first and the second extracting solvent comprise an aliphatic alcohol, which is independently selected from methanol, ethanol, propanol, isopropanol, n-butanol, isobutanol, sec-butyl alcohol or tert-butyl alcohol. In preferred embodiments of the present invention, the aliphatic alcohol of one or both of the first and the second extracting solvent is methanol. Most preferably, the aliphatic alcohol of the first and the second extracting solvent is methanol.

The first and the second extracting solvent further comprise a halogenated hydrocarbon, i.e. as used herein a hydrocarbon, preferably an alkane, which hydrocarbon has at least one hydrogen atom substituted with a halogen atom. Preferably, the halogenated hydrocarbon in the first and the second extracting solvent is independently selected from a hydrocarbon, preferably a branched or straight chain alkane, which hydrocarbon has 1 to 4 carbon atoms and wherein at least one hydrogen atom is substituted with a halogen selected from Br, Cl, or F, in particular from Cl. Preferably, the halogenated hydrocarbon in the first and the second extracting solvent is independently selected from an alkane with 1 to 2 carbon atoms in which at least one hydrogen atom is substituted with a Cl atom, in particular selected from methyl chloride, dichloromethane or chloroform. Most preferably, the halogenated hydrocarbon in the first or the second or both extracting solvents is chloroform. In still more preferred embodiments, the halogenated hydrocarbon in the first and the second extracting solvent is chloroform.

Preferably, the volume ratio of halogenated hydrocarbon to aliphatic alcohol in the first extracting solvent is less than 1, i.e. less than 1:1. Preferably, the volume ratio of halogenated hydrocarbon to aliphatic alcohol in the second extracting solvent is above 1, i.e. above 1:1

In more preferred embodiments of the present invention, the first extracting solvent comprises chloroform and methanol, preferably with a volume ratio of chloroform to methanol of less than 1:1, preferably at most 2:3, more preferably between 2:3 and 1:5, further preferably of about 1:2.

The second extracting solvent more preferably comprises chloroform and methanol, preferably with a volume ratio of chloroform to methanol of more than 1:1, more preferably of at least 3:2, in particular of 3:2 to 2.5:1, most preferably about 2:1.

In especially preferred embodiment, the first extracting solvent comprises and in particular essentially consists of chloroform and methanol with a ratio of about 1:2 (v/v) and the second extracting solvent comprises and preferably essentially consists of chloroform and methanol with a ratio of about 2:1 (v/v). The extracting solvents are in particular used sequentially, i.e. subsequently.

Preferably, the *Cordyceps* material is sequentially extracted with two extracting solvents, namely with the first and the second extracting solvent. More preferably, the *Cordyceps* material is extracted with the first extracting solvent at least 2 and preferably 2 times. The *Cordyceps* material is preferably extracted with the second extracting solvent at least 2 and preferably 2 times. Most preferably, the *Cordyceps* material is extracted with the first extracting solvent 2 times and subsequently with the second extracting solvent 2 times.

Preferably, step (i) comprises steps of
a) contacting the *Cordyceps* material with a first part of the first extracting solvent and incubating for at least 1 h at at least 30° C. and filtering the extract for obtaining a first filtrate and a first residue;
b) contacting the first residue with the second part of the first extraction solvent and sonicating the mixture for at least 10 min and filtering the extract for obtaining a second filtrate and a second residue;
c) contacting the second residue with a first part of the second extracting solvent and sonicating the mixture for at least 10 min and filtering the extract for obtaining a third filtrate and a third residue;
d) contacting the third residue with a second part of the second extracting solvent and sonicating the mixture for at least 10 min and filtering the extract for obtaining a fourth filtrate and a fourth residue;
e) combining the first to fourth filtrate;
f) adding a base to the combined filtrates and incubating for at least 1 h at at least 30° C.;
g) neutralizing the mixture obtained after step f) with a carboxylic acid;
h) subjecting the neutralized mixture after step g) to centrifugation and optionally evaporating the supernatant for obtaining the sphingolipid crude extract.

In step a), incubation is preferably carried out for at least 10 h, in particular for about 12 h, preferably at least 40° C., in particular at about 48° C. The filtration is preferably a pressure filtration in particular an atmospheric pressure filtration preferably with a filter with an aperture size of from 80 μm to 120 μm such as with the qualitative filter paper with the characteristics D 70 mm, aperture size: 80-120 μm.

In step b), sonicating is carried out preferably by means of ultrasonication preferably with operating frequencies of least 10 kHz, further preferred of at least 20 kHz, preferably for at least 20 min, in particular for about 30 min. The filtration is preferably a pressure filtration, in particular an atmospheric pressure filtration preferably with a filter with an aperture size of from 80 μm to 120 μm such as with the qualitative filter paper with the characteristics D 70 mm, aperture size: 80-120 μm.

In step c), sonicating is carried out preferably by means of ultrasonication preferably with operating frequencies of least 10 kHz, further preferred of at least 20 kHz, preferably for at least 20 min, in particular for about 30 min. The filtration is preferably a pressure filtration in particular an atmospheric pressure filtration preferably with a filter with an aperture size of from 80 μm to 120 μm such as with the qualitative filter paper with the characteristics D 70 mm, aperture size: 80-120 μm.

In step d), sonicating is carried out preferably by means of ultrasonication preferably with operating frequencies of least 10 kHz, further preferred of at least 20 kHz, preferably for at least 20 min, in particular for about 30 min. The filtration is preferably a pressure filtration in particular an atmospheric pressure filtration preferably with a filter with an aperture size of from 80 μm to 120 μm such as with the qualitative filter paper with the characteristics D 70 mm, aperture size: 80-120 μm.

In step e), the combined filtrates are preferably concentrated, i.e. the volume is reduced to a desired volume preferably by means of a rotary evaporator.

In step f), incubation is carried out for preferably about 2 h, preferably at about 37° C., preferably accompanied by shaking. The base is preferably an alkali hydroxide. Alkali hydroxides are a class of chemical compounds which are composed of an alkali metal cation, i.e. cation of lithium (Li), sodium (Na), potassium (K), rubidium (Rb), caesium (Cs), and the hydroxide anion (HO$^-$). In particular, the alkali metal cation is K or Na. More preferably, the base is KOH in an aliphatic alcohol, preferably in methanol.

The term "neutralizing" in step g) as used herein means adding a carboxylic acid for obtaining a pH between 6 and 8. A carboxylic acid as used herein is a compound containing at least one carboxyl group, i.e. —COOH, in particular based on a hydrocarbon such as a branched or straight chain alkane in which at least one carbon atom forms a carboxyl group. In particular, the carboxylic acid is based on a straight chain alkane with 1 to 4 carbon atoms more preferably 1 to 2 carbon atoms, wherein at least one carbon atom forms a carboxyl group, preferably one carboxyl group is present. More preferably, the carboxylic acid in step g) is acetic acid.

Step h) preferably comprises evaporating the supernatant at at least 35° C., preferably at about 40° C. to the desired volume or to a solid to form the sphingolipid crude extract. The first chromatographic separation step in step (ii) is preferably carried out by means of column chromatography, in particular classical (low pressure) column chromatography. The second chromatographic separation step in step (ii) is preferably carried out by means of column chromatography, in particular classical (low pressure) column chromatography. More preferably, both of the first and the second chromatographic separation step are carried out by means of column chromatography, more preferred by means of classical (low pressure) column chromatography. Classical (low pressure) column chromatography is known to the skilled person and is usually operating with a lower pressure up to about 0.5 MPa compared to medium pressure or high performance liquid chromatography.

The first chromatographic separation step is carried out with a liquid chromatography, preferably column chromatography and in particular classical column chromatography, with a stationary phase comprising unmodified silica and in particular essentially consisting of unmodified silica gel. The stationary phase preferably has a particle size of up to 70 μm, more preferably up to 45 μm, most preferably 10 to 14 μm and a pore size of preferably about 60 Å. The skilled person is aware of the term "unmodified silica" which means that no polar groups or non-polar groups have been chemically attached to the silica. The inner diameter of the column in the first chromatographic separation step in embodiments, in which column chromatography is applied, is preferably between 3 and 5 cm, in particular about 4.2 cm and the length of the column is preferably between 20 and 40 cm, in particular about 29 cm.

Preferably at least a first and a second and more preferably at least a first, a second and a third and in particular a first, a second and a third eluting solvent are sequentially applied. I.e. an amount of the first eluting solvent is applied, then an amount of the second eluting solvent and finally the third eluting solvent such that in case of a column chromatography the column is penetrated by the first, then by the second and finally by the third eluting solvent. Preferably the first eluting solvent comprises and in particular essentially consists of a halogenated hydrocarbon. The second eluting solvent preferably comprises and more preferably essentially consists of a ketone and an aliphatic alcohol. The third eluting solvent preferably comprises and more preferably essentially consists of an aliphatic alcohol.

The halogenated hydrocarbon of the first eluting solvent is preferably based on a branched or straight chain alkane which has 1 to 4 carbon atoms and wherein at least one hydrogen atom is substituted with a halogen selected from Br, Cl, or F, in particular from Cl. Preferably, the halogenated hydrocarbon in the first eluting solvent is selected from an alkane with 1 to 2 carbon atoms in which at least one hydrogen atom is substituted with a Cl atom, in particular selected from methyl chloride, dichloromethane or chloroform. Most preferably, the halogenated hydrocarbon in the first eluting solvent is chloroform.

A ketone is in particular a straight chain, branched, or cyclic alkyl ketone having from 3 to 8 carbon atoms, inclusive of the carbonyl carbon, and may include acetone, butanone, 2-pentanone, 3-pentanone, hexanone, methyl isobutyl ketone, cyclohexanone, and the like. The ketone in the second eluting solvent is preferably an alkyl ketone with a total of 2 to 4 carbon atoms, in particular acetone. The aliphatic alcohol in the second eluting solvent is preferably a monohydric aliphatic alcohol containing 1 to 4 carbon atoms such as methanol, ethanol, propanol, isopropanol, n-butanol, isobutanol, sec-butyl alcohol or tert-butyl alcohol. In preferred embodiments of the present invention, the aliphatic alcohol of the second eluting solvent is methanol. Most preferably, the aliphatic alcohol is methanol and the ketone is acetone in the second eluting solvent. The volume ratio of ketone to aliphatic alcohol in the second eluting solvent is preferably about 9:1.

The aliphatic alcohol in the third eluting solvent is preferably an aliphatic alcohol with 1 to 4 carbon atoms, in particular a monohydric aliphatic alcohol, such as methanol, ethanol, propanol, isopropanol, n-butanol, isobutanol, sec-butyl alcohol or tert-butyl alcohol. In preferred embodiments of the present invention, the aliphatic alcohol in the third eluting solvent is methanol.

In particular embodiments of the present invention, the first eluting solvent comprises and in particular essentially consists of chloroform, the second eluting solvent preferably comprises and more preferably essentially consists of acetone and methanol and the third eluting solvent preferably comprises and more preferably essentially consists of methanol. Suitable amounts used include about 5 bed volume of the first eluting solvent, about 3.5 bed volume of the second eluting solvent and about 7.5 bed volume of the third eluting solvent.

Preferably, at least two and more preferably at least three and further preferred more than three fractions are collected, preferably the fractions are collected as determined by a desired fixed volume of each fraction such as a certain bed volume, in particular the fractions are collected such that each fraction has 100 ml or 0.1 bed volume, in particular such that each fraction has 0.1 bed volume.

Fractions collected are preferably used for forming at least three sphingolipid-enriched fractions. Preferably, these sphingolipid-enriched fractions are subjected to the second chromatographic separation step. Whether a fraction is a "sphingolipid-enriched fraction", which at least contains sphingolipids in detectable amounts, is in particular determined based on LC-MS behavior, i.e. based on a LC-MC analysis preferably a LC-MS analysis as used for steps (iii) and (iv) which will be further described below.

More specifically, the fractions collected by volume like 0.1 bed volume/fraction or 100 ml/fraction are preferably subsequently subjected to LC-MS in order to identify the fractions comprising sphingolipids and the fractions comprising similar sphingolipids among them. Preferably, two or more fractions are combined for forming one sphingolipid-enriched fraction. In particular all fractions collected which comprise similar sphingolipids are combined for forming a sphingolipid-enriched fraction. At least three sphingolipid-enriched fractions can be formed and in particular three sphingolipid-enriched fractions are formed, which are subjected to the second chromatographic separation step.

The second chromatographic separation step is carried out as liquid chromatography, preferably column chromatography in particular classical column chromatography, with a stationary phase comprising silica modified with polar groups and in particular essentially consisting of silica like silica gel modified with polar groups. "Polar groups" as known in the art are functional groups containing electronegative atoms like nitrogen or oxygen.

The skilled person is aware of the term "modified silica" and able to select suitable polar groups for modification. Such polar groups in particular include amino-, diol- and/or cyano-groups bonded to the silica matrix via short-chain non-polar spacers, usually straight chain or branched alkyl groups, also known as "amino-modified", "cyano-modified" or "diol-modified" silica. In particular, 3-(2,3-dihydroxypropoxy)propyl, aminopropyl and/or cyanopropyl can be bonded to the silica matrix. Most preferably, the polar groups are amino groups in particular in form of aminopropyl-groups bonded to the silica matrix, i.e. the modified silica is in particular an amino-modified silica and silica gel, respectively. The modified silica stationary phase preferably has a particle size of up to 70 μm, more preferably 35 to 70 μm and a pore size of preferably about 60 Å. The inner diameter of the column in the second chromatographic separation step in embodiments, in which column chromatography is applied, is preferably between 3 and 5 cm, in particular about 4.2 cm and the length of the column is preferably between 20 and 40 cm, in particular about 25 cm.

In embodiments of the present invention, at least three and in particular three sphingolipid-enriched fractions as obtained with the first chromatographic separation step are separately subjected to the second chromatographic separation step.

Preferably at least four and in particular at least five, namely a first, second, third, fourth and fifth eluting solvent are sequentially applied in the second chromatographic separation step. Preferably, in the second chromatographic separation step:

the first eluting solvent comprises and more preferably essentially consists of a hydrocarbon;

the second eluting solvent comprises and more preferably essentially consists of a hydrocarbon and an ester;

the third eluting solvent comprises and more preferably essentially consists of a halogenated hydrocarbon and an aliphatic alcohol;

the fourth eluting solvent comprises and more preferably essentially consists of a ketone and an aliphatic alcohol;

the fifth eluting solvent comprises and more preferably essentially consists of a halogenated hydrocarbon and an aliphatic alcohol.

The hydrocarbon in the first eluting solvent of the second chromatographic separation step is preferably a hydrocarbon with 3 to 8 carbon atoms, in particular an alkane with 3 to 8 carbon atoms and in particular hexane.

The hydrocarbon in the second eluting solvent of the second chromatographic separation step is preferably a hydrocarbon with 3 to 8 carbon atoms, in particular an alkane with 3 to 8 carbon atoms and in particular hexane. The ester in the second eluting solvent of the second chromatographic separation step is preferably a $C_1$-$C_6$ aliphatic alcohol ester of a $C_1$-$C_7$ alkyl carboxylic acid. Further preferably, the ester is a $C_3$-$C_7$ ester, in particular the ester is ethyl acetate. Most preferably, the hydrocarbon is hexane and the ester is ethyl acetate and the volume ratio is preferably about 85:15.

The halogenated hydrocarbon of the third eluting solvent of the second chromatographic separation step is preferably based on a branched or straight chain alkane which has 1 to 4 carbon atoms and wherein at least one hydrogen atom is substituted with a halogen selected from Br, Cl, or F, in particular from Cl. Preferably, the halogenated hydrocarbon in the third eluting solvent is selected from an alkane with 1 to 2 carbon atoms in which at least one hydrogen atom is substituted with a Cl atom, in particular selected from methyl chloride, dichloromethane or chloroform. Most preferably, the halogenated hydrocarbon in the third eluting solvent of the second chromatographic separation step is chloroform. The aliphatic alcohol in the third eluting solvent of the second chromatographic separation step is preferably an aliphatic alcohol with 1 to 4 carbon atoms, in particular a monohydric aliphatic alcohol, such as methanol, ethanol, propanol, isopropanol, n-butanol, isobutanol, sec-butyl alcohol or tert-butyl alcohol. In preferred embodiments of the present invention, the aliphatic alcohol in the third eluting solvent of the second chromatographic separation step is methanol. The volume ratio of halogenated hydrocarbon to aliphatic alcohol in the third eluting solvent of the second chromatographic separation step is preferably about 23:1.

A ketone in the fourth eluting solvent of the second chromatographic separation step is in particular a straight chain, branched, or cyclic alkyl ketone having from 3 to 8 carbon atoms, inclusive of the carbonyl carbon, and may include acetone, butanone, 2-pentanone, 3-pentanone, hexanone, methyl iso-butyl ketone, cyclohexanone, and the like. The ketone in the fourth eluting solvent is preferably an alkyl ketone with a total of 2 to 4 carbon atoms, in particular acetone. The aliphatic alcohol in the fourth eluting solvent of the second chromatographic separation step is preferably a monohydric aliphatic alcohol containing 1 to 4 carbon atoms such as methanol, ethanol, propanol, isopropanol, n-butanol, isobutanol, sec-butyl alcohol or tert-butyl alcohol. In preferred embodiments of the present invention, the aliphatic alcohol of the fourth eluting solvent of the second chromatographic separation step is methanol. Most preferably, the ketone is acetone and the aliphatic alcohol is methanol in the fourth eluting solvent of the second chromatographic separation step with a volume ratio of preferably about 9:1.35.

Suitable amounts used in the second chromatographic separation step include about 2 bed volume of the first eluting solvent, about 6 bed volume of the second eluting solvent, about 5 bed volume of the third eluting solvent, about 5 bed volume of the fourth eluting solvent and about 5 bed volume of the fifth eluting solvent.

The halogenated hydrocarbon of the fifth eluting solvent of the second chromatographic separation step is preferably based on a branched or straight chain alkane which has 1 to 4 carbon atoms and wherein at least one hydrogen atom is substituted with a halogen selected from Br, Cl, or F, in particular from Cl. Preferably, the halogenated hydrocarbon in the fifth eluting solvent of the second chromatographic separation step is selected from an alkane with 1 to 2 carbon atoms in which at least one hydrogen atom is substituted with a Cl atom, in particular selected from methyl chloride, dichloromethane or chloroform. Most preferably, the halogenated hydrocarbon in the fifth eluting solvent of the second chromatographic separation step is chloroform. The aliphatic alcohol in the fifth eluting solvent of the second chromatographic separation step is preferably an aliphatic alcohol with 1 to 4 carbon atoms, in particular a monohydric aliphatic alcohol, such as methanol, ethanol, propanol, isopropanol, n-butanol, isobutanol, sec-butyl alcohol or tert-butyl alcohol. In preferred embodiments of the present invention, the aliphatic alcohol in the fifth eluting solvent of the second chromatographic separation step is methanol. The volume ratio of halogenated hydrocarbon to aliphatic alcohol in the fifth eluting solvent of the second chromatographic separation step is preferably about 2:1.

In particular, at least three, preferably at least four and more preferably more than four fractions are collected, preferably the fractions are collected as determined by a desired fixed amount of each fraction like 100 ml of each fraction or a certain bed volume, in particular the fractions are collected such that each fraction has 0.1 bed volume.

The fractions collected are used for forming a "first sphingolipid fraction", a "second sphingolipid fraction", a "third sphingolipid fraction" and a "fourth sphingolipid fraction". These terms are not to be understood to imply any order of collection or time of collection of the respective fraction or fractions forming it during the second chromatographic separation step. In particular, first, second, third and fourth sphingolipid fraction are selected from the total number of collected fractions based on LC-MS behavior, i.e. based on a LC-MC analysis preferably a LC-MS analysis carried out as steps (iii) and (iv) which will be further described below.

More specifically, fractions collected by volume like 0.1 bed volume/fraction or 100 ml/fraction are preferably subsequently subjected to LC-MS in order to identify the fractions comprising sphingolipids and the subgroup of the sphingolipids, namely sphingoid bases, ceramides, phosphosphingolipids or glycosphingolipids. In particular, all fractions which contain the same subgroup of sphingolipids are combined for forming one of the first, second, third or fourth sphingolipid fraction. Preferred conditions for obtaining the first, second, third and fourth sphingolipid fraction are described in table 1.

TABLE 1 preferred conditions for obtaining the first, second, third and fourth sphingolipid fraction

| Sphingolipid fraction | Eluting solvent |
| --- | --- |
| first sphingolipid fraction | CHCl$_3$/methanol (23:1, v:v) and acetone/methanol (9:1.35, v:v) |
| second sphingolipid fraction | CHCl$_3$/methanol (23:1, v:v) |
| third sphingolipid fraction | acetone/methanol (9:1.35, v:v) |
| fourth sphingolipid fraction | CHCl$_3$/methanol (2:1, v:v) |

The first sphingolipid fraction preferably comprises the "sphingoid base portion", in particular it essentially consists of solvents and the sphingoid base portion, i.e. a portion with a high amount of sphingoid bases in particular of sphingosines and sphinganines, i.e. with preferably more than 50 wt.-%, in particular at least 70 wt.-% and further preferred of more than 80 wt.-% of sphingoid bases based on the weight of the sphingoid base portion. The sphingoid base portion preferably comprises one or more of the sphingoid bases given in table 2:

TABLE 2 preferred sphingoid bases in the sphingoid base portion

| Sphingoid base | Formula |
| --- | --- |
| Sa (d14:0) | C14 H31 N O2 |
| So (d14:1) | C14 H29 N O2 |
| So (d14:2) | C14 H27 N O2 |
| So (d14:3) | C14 H25 N O2 |
| So (d15:1) | C15 H31 N O2 |
| So (d16:1) | C16 H33 N O2 |
| Sa (d17:0) | C17 H37 N O2 |
| Sa (d18:0) | C18 H39 N O2 |
| So (d18:1) | C18 H37 N O2 |
| So (d18:5) | C18 H29 N O2 |
| So (d19:1) | C19 H39 N O2 |
| So (d19:2) | C19 H37 N O2 |
| So (d20:2) | C20 H39 N O2 |
| So (d20:3) | C20 H37 N O2 |
| So (d22:1) | C22 H45 N O2 |
| So (d22:1) isomer | C22 H45 N O2 |
| So (d22:2) | C22 H43 N O2 |
| So (d22:3) | C22 H41 N O2 |
| So (d22:5) | C22 H37 N O2 |
| So (t15:2) | C15 H29 N O3 |
| So (t15:3) | C15 H27 N O3 |
| Sa (t16:0) | C16 H35 N O3 |
| Sa (t18:0) | C18 H39 N O3 |
| So (t18:1) | C18 H37 N O3 |
| So (t18:2) | C18 H35 N O3 |
| So (t19:1) | C19 H39 N O3 |
| So (t19:2) | C19 H37 N O3 |
| So (t20:1) | C20 H41 N O3 |
| So (t21:3) | C21 H39 N O3 |
| So (t21:4) | C21 H37 N O3 |
| Sa (t22:0) | C22 H47 N O3 |
| So (t22:1) | C22 H45 N O3 |
| So (t22:2) | C22 H43 N O3 |
| So (t23:4) | C23 H41 N O3 |
| So (m14:3) | C14 H25 N O |
| Sa (m17:0) | C17 H37 N O |
| Sa (m18:0) | C18 H39 N O |
| So (m18:1) | C18 H37 N O |
| So (m22:1) | C22 H45 N O |
| So (m22:2) | C22 H43 N O |
| So (m22:3) | C22 H41 N O |
| So (m22:3) isomer | C22 H41 N O |
| Sphingofungin A | C21 H41 N3 O6 |

More preferably, the sphingoid base portion comprises one or more of the sphingoid bases of table 3:

TABLE 3 more preferred sphingoid bases in the sphingoid base portion

| Sphingoid base | Formula |
| --- | --- |
| So (d18:5) | C18 H29 N O2 |
| So (d20:3) | C20 H37 N O2 |
| So (d22:5) | C22 H37 N O2 |
| So (t15:2) | C15 H29 N O3 |
| So (t15:3) | C15 H27 N O3 |
| So (t19:2) | C19 H37 N O3 |
| So (t21:3) | C21 H39 N O3 |
| So (t21:4) | C21 H37 N O3 |
| So (m22:1) | C22 H45 N O |
| So (m22:2) | C22 H43 N O |
| So (m22:3) | C22 H41 N O |
| So (m22:3) isomer | C22 H41 N O |

In particular, the sphingoid base portion comprises all of the following sphingoid bases:

So (d18:5) having the following Formula (3) with x=1 and y=2:

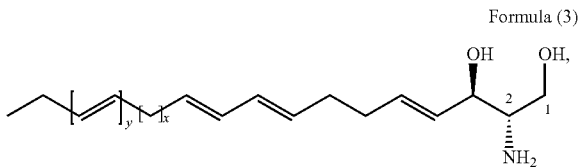

Formula (3)

So(d20:3) having Formula (3) as given above with x=7 and y=0,

So(d22:5) having Formula (3) as given above with x=5 and y=2,

So(t15:2) having Formula (4) with x=4 and y=0:

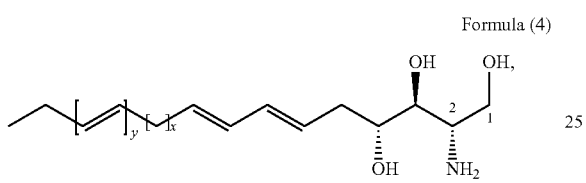

Formula (4)

So(t15:3) having Formula (4) as given above with x=2 and y=1,

So(t19:2) having Formula (4) as given above with x=8 and y=0,

So(t21:3) having Formula (4) as given above with x=8 and y=1,

So(t21:4) having Formula (4) as given above with x=6 and y=2,

So(m22:1) having Formula (5) with x=12, y=0 and z=0:

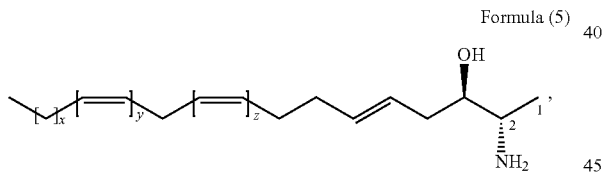

Formula (5)

So(m22:2) having Formula (5) as given above with x=10, y=0 and z=1, and

So(m22:3) having Formula (5) as given above with x=8, y=1 and z=1.

The second sphingolipid fraction preferably comprises the "ceramide portion", in particular it essentially consists of solvents and the ceramide portion, i.e. a portion with a high amount of ceramides, i.e. with preferably more than 50 wt.-%, in particular at least 70 wt.-% and more preferably more than 80 wt.-% of ceramides based on the weight of the ceramide portion. The ceramide portion preferably comprises one or more of the ceramides given in table 4:

TABLE 4

| preferred ceramides in the ceramide portion | |
|---|---|
| Ceramide | Formula |
| Cer (m14:2/18:2) | C32 H57 N O2 |
| Cer (m14:3/18:2) | C32 H55 N O2 |

TABLE 4-continued

| preferred ceramides in the ceramide portion | |
|---|---|
| Ceramide | Formula |
| Cer (m14:3/18:2) isomer | C32 H55 N O2 |
| Cer (m14:3/24:1) | C38 H69 N O2 |
| Cer (m15:1/5:0) | C20 H39 N O2 |
| Cer (m15:2/18:2) | C33 H59 N O2 |
| Cer (m15:3/18:1) | C33 H59 N O2 |
| Cer (m16:3/18:1) | C34 H61 N O2 |
| Cer (m16:3/22:1) | C38 H69 N O2 |
| Cer (m18:2/3:0) | C21 H39 N O2 |
| Cer (m18:2/19:0) | C37 H71 N O2 |
| Cer (m18:3/18:1) | C36 H65 N O2 |
| Cer (m18:3/18:2) | C36 H63 N O2 |
| Cer (m18:5/5:0) | C23 H37 N O2 |
| Cer (m19:4/16:0) | C35 H63 N O2 |
| Cer (m19:3/17:0) | C35 H65 N O2 |
| Cer (d14:0/16:0) | C30 H61 N O3 |
| Cer (d14:0/18:0) | C32 H65 N O3 |
| Cer (d14:0/18:1) | C32 H63 N O3 |
| Cer (d14:0/20:0) | C34 H69 N O3 |
| Cer (d14:0/22:0) | C36 H73 N O3 |
| Cer (d14:0/23:0) | C37 H75 N O3 |
| Cer (d14:0/24:0) | C38 H77 N O3 |
| Cer (d16:0/20:0) | C36 H73 N O3 |
| Cer (d16:0/22:0) | C38 H77 N O3 |
| Cer (d16:0/23:0) | C39 H79 N O3 |
| Cer (d18:0/16:0) | C34 H69 N O3 |
| Cer (d18:0/17:0) | C35 H71 N O3 |
| Cer (d18:0/18:0) | C36 H73 N O3 |
| Cer (d18:0/18:1) | C36 H71 N O3 |
| Cer (d18:0/18:2) | C36 H69 N O3 |
| Cer (d18:0/20:0) | C38 H77 N O3 |
| Cer (d18:0/22:0) | C40 H81 N O3 |
| Cer (d18:0/22:0) isomer | C40 H81 N O3 |
| Cer (d18:0/23:0) | C41 H83 N O3 |
| Cer (d18:0/24:0) | C42 H85 N O3 |
| Cer (d18:0/25:0) | C43 H87 N O3 |
| Cer (d18:0/26:0) | C44 H89 N O3 |
| Cer (d20:0/25:0) | C45 H91 N O3 |
| Cer (d20:0/26:0) | C46 H93 N O3 |
| Cer (d20:0/27:0) | C47 H95 N O3 |
| Cer (d22:0/26:0) | C48 H97 N O3 |
| Cer (d24:0/26:0) | C50 H101 N O3 |
| Cer (d25:0/24:0) | C49 H99 N O3 |
| Cer (d18:0/16:0(OH)) | C34 H69 N O4 |
| Cer (d18:0/20:0(OH)) | C38 H77 N O4 |
| Cer (d18:0/24:0(OH)) | C42 H85 N O4 |
| Cer (d20:0/26:0(OH)) | C46 H93 N O4 |
| Cer (d22:0/25:0(OH)) | C47 H95 N O4 |
| Cer (t14:0/14:0) | C28 H57 N O4 |
| Cer (t18:0/16:0) | C34 H69 N O4 |
| Cer (t18:0/16:1) | C34 H67 N O4 |
| Cer (t18:0/17:0) | C35 H71 N O4 |
| Cer (t18:0/17:1) | C35 H69 N O4 |
| Cer (t18:0/18:0) | C36 H73 N O4 |
| Cer (t18:0/18:1) | C36 H71 N O4 |
| Cer (t18:0/18:2) | C36 H69 N O4 |
| Cer (t18:0/19:1) | C37 H73 N O4 |
| Cer (t18:0/20:0) | C38 H77 N O4 |
| Cer (t18:0/20:1) | C38 H75 N O4 |
| Cer (t18:0/21:0) | C39 H79 N O4 |
| Cer (t18:0/21:1) | C39 H77 N O4 |
| Cer (t18:0/22:0) | C40 H81 N O4 |
| Cer (t18:0/22:1) | C40 H79 N O4 |
| Cer (t18:0/23:0) | C41 H83 N O4 |
| Cer (t18:0/23:1) | C41 H81 N O4 |
| Cer (t18:0/24:0) | C42 H85 N O4 |
| Cer (t18:0/24:1) | C42 H83 N O4 |
| Cer (t18:0/24:2) | C42 H81 N O4 |
| Cer (t18:0/24:5) | C42 H75 N O4 |
| Cer (t18:0/25:0) | C43 H87 N O4 |
| Cer (t18:0/26:0) | C44 H89 N O4 |
| Cer (t18:0/27:0) | C45 H91 N O4 |
| Cer (t18:0/26:0) isomer | C44 H89 N O4 |
| Cer (t18:0/27:0) isomer | C45 H91 N O4 |
| Cer (t18:0/25:1) | C43 H85 N O4 |
| Cer (t18:0/26:1) | C44 H87 N O4 |
| Cer (t18:0/26:5) | C44 H79 N O4 |

TABLE 4-continued preferred ceramides in the ceramide portion

| Ceramide | Formula |
|---|---|
| Cer (t19:0/18:1) | C37 H73 N O4 |
| Cer (t19:0/18:2) | C37 H71 N O4 |
| Cer (t20:0/26:0) | C46 H93 N O4 |
| Cer (t20:0/26:1) | C46 H91 N O4 |
| Cer (t20:0/30:1) | C50 H99 N O4 |
| Cer (t20:0/31:1) | C51 H101 N O4 |
| Cer (t22:0/25:0) | C47 H95 N O4 |
| Cer (t22:0/26:0) | C48 H97 N O4 |
| Cer (t22:0/26:1) | C48 H95 N O4 |
| Cer (t22:0/27:0) | C49 H99 N O4 |
| Cer (t22:0/28:0) | C50 H101 N O4 |
| Cer (t16:0/12:0(OH)) | C28 H57 N O5 |
| Cer (t18:0/16:0(OH)) | C34 H69 N O5 |
| Cer (t18:0/17:0(OH)) | C35 H71 N O5 |
| Cer (t18:0/17:4(OH)) | C35 H63 N O5 |
| Cer (t18:0/18:0(OH)) | C36 H63 N O5 |
| Cer (t18:0/20:0(OH)) | C38 H77 N O5 |
| Cer (t18:0/21:0(OH)) | C39 H79 N O5 |
| Cer (t18:0/22:0(OH)) | C40 H81 N O5 |
| Cer (t18:0/23:0(OH)) | C41 H83 N O5 |
| Cer (t18:0/23:1(OH)) | C41 H81 N O5 |
| Cer (t18:0/24:0(OH)) | C42 H85 N O5 |
| Cer (t18:0/24:1(OH)) | C42 H83 N O5 |
| Cer (t18:0/25:0(OH)) | C43 H87 N O5 |
| Cer (t18:0/26:0(OH)) | C44 H89 N O5 |
| Cer (d14:1/16:0) | C30 H59 N O3 |
| Cer (d14:1/18:0) | C32 H63 N O3 |
| Cer (d14:1/18:1) | C32 H61 N O3 |
| Cer (d14:1/18:2) | C32 H59 N O3 |
| Cer (d14:1/20:0) | C34 H67 N O3 |
| Cer (d14:1/20:4) | C34 H59 N O3 |
| Cer (d14:1/22:0) | C36 H71 N O3 |
| Cer (d14:1/23:0) | C37 H73 N O3 |
| Cer (d14:1/24:0) | C38 H75 N O3 |
| Cer (d14:2/16:0) | C30 H57 N O3 |
| Cer (d14:2/18:2) | C32 H57 N O3 |
| Cer (d14:2/20:4) | C34 H57 N O3 |
| Cer (d14:2/20:5) | C34 H55 N O3 |
| Cer (d14:2/20:6) | C34 H53 N O3 |
| Cer (d14:2/24:3) | C38 H67 N O3 |
| Cer (d14:2/25:3) | C39 H69 N O3 |
| Cer (d14:2/26:3) | C40 H71 N O3 |
| Cer (d15:1/20:0) | C35 H69 N O3 |
| Cer (d15:1/22:0) | C37 H73 N O3 |
| Cer (d15:1/22:1) | C37 H71 N O3 |
| Cer (d15:2/22:1) | C37 H69 N O3 |
| Cer (d16:1/22:0) | C38 H75 N O3 |
| Cer (d16:1/22:1) | C38 H73 N O3 |
| Cer (d16:1/22:2) | C38 H71 N O3 |
| Cer (d16:1/24:0) | C40 H79 N O3 |
| Cer (d16:2/22:2) | C38 H69 N O3 |
| Cer (d16:2/23:1) | C39 H73 N O3 |
| Cer (d16:2/23:2) | C39 H71 N O3 |
| Cer (d16:2/24:2) | C40 H73 N O3 |
| Cer (d18:1/14:1) | C32 H61 N O3 |
| Cer (d18:1/16:0) | C34 H67 N O3 |
| Cer (d18:1/16:1) | C34 H65 N O3 |
| Cer (d18:1/17:0) | C35 H69 N O3 |
| Cer (d18:1/17:1) | C35 H67 N O3 |
| Cer (d18:1/18:0) | C36 H71 N O3 |
| Cer (d18:1/18:1) | C36 H69 N O3 |
| Cer (d18:1/18:2) | C36 H67 N O3 |
| Cer (d18:1/20:0) | C38 H75 N O3 |
| Cer (d18:1/20:1) | C38 H73 N O3 |
| Cer (d18:1/21:0) | C39 H77 N O3 |
| Cer (d18:1/22:0) | C40 H79 N O3 |
| Cer (d18:1/22:1) | C40 H77 N O3 |
| Cer (d18:1/22:2) | C40 H75 N O3 |
| Cer (d18:1/23:0) | C41 H81 N O3 |
| Cer (d18:1/23:1) | C41 H79 N O3 |
| Cer (d18:1/23:5) | C41 H71 N O3 |
| Cer (d18:1/24:0) | C42 H83 N O3 |
| Cer (d18:1/24:1) | C42 H81 N O3 |
| Cer (d18:1/24:2) | C42 H79 N O3 |
| Cer (d18:1/24:5) | C42 H73 N O3 |
| Cer (d18:1/25:0) | C43 H85 N O3 |
| Cer (d18:1/25:1) | C43 H83 N O3 |
| Cer (d18:1/25:2) | C43 H81 N O3 |
| Cer (d18:1/25:4) | C43 H77 N O3 |
| Cer (d18:1/26:0) | C44 H87 N O3 |
| Cer (d18:1/26:1) | C44 H85 N O3 |
| Cer (d18:1/26:4) | C44 H77 N O3 |
| Cer (d18:1/26:4) isomer | C44 H77 N O3 |
| Cer (d18:1/27:5) | C45 H79 N O3 |
| Cer (d18:1/28:4) | C46 H83 N O3 |
| Cer (d18:1/28:5) | C46 H81 N O3 |
| Cer (d18:1/29:5) | C47 H83 N O3 |
| Cer (d18:1/32:4) | C50 H91 N O3 |
| Cer (d18:1/32:5) | C50 H89 N O3 |
| Cer (d19:1/24:0) | C43 H85 N O3 |
| Cer (d19:2/16:0) | C35 H67 N O3 |
| Cer (d19:2/16:1) | C35 H65 N O3 |
| Cer (d19:2/16:2) | C35 H63 N O3 |
| Cer (d19:2/18:2) | C37 H67 N O3 |
| Cer (d19:2/18:3) | C37 H65 N O3 |
| Cer (d19:2/18:4) | C37 H63 N O3 |
| Cer (d19:2/20:0) | C39 H75 N O3 |
| Cer (d19:2/20:4) | C39 H67 N O5 |
| Cer (d19:2/21:5) | C40 H67 N O3 |
| Cer (d19:2/22:1) | C41 H77 N O3 |
| Cer (d19:2/24:1) | C43 H81 N O3 |
| Cer (d19:2/24:2) | C43 H79 N O3 |
| Cer (d19:3/17:4) | C36 H59 N O3 |
| Cer (d20:1/24:1) | C44 H85 N O3 |
| Cer (d20:1/25:0) | C45 H89 N O3 |
| Cer (d20:1/26:0) | C46 H91 N O3 |
| Cer (d20:1/26:2) | C46 H87 N O3 |
| Cer (d20:1/27:0) | C47 H93 N O3 |
| Cer (d20:2/28:0) | C48 H93 N O3 |
| Cer (d21:1/28:0) | C49 H97 N O3 |
| Cer (d22:1/26:2) | C48 H91 N O3 |
| Cer (d22:1/26:0) | C48 H95 N O3 |
| Cer (d22:1/27:2) | C49 H93 N O3 |
| Cer (d22:1/28:0) | C50 H99 N O3 |
| Cer (d14:1/18:3(OH)) | C32 H57 N O4 |
| Cer (d14:2/14:3(OH)) | C28 H47 N O4 |
| Cer (d18:1/26:2(OH)) | C44 H83 N O4 |
| Cer (d19:2/16:1(OH)) | C35 H65 N O4 |
| Cer (d19:2/25:2(OH)) | C44 H81 N O4 |
| Cer (d19:3/16:1(OH)) | C35 H63 N O4 |
| Cer (d20:1/26:2(OH)) | C46 H87 N O4 |
| Cer (d20:1/28:2(OH)) | C48 H91 N O4 |
| Cer (t18:1/16:0) | C34 H67 N O4 |
| Cer (t18:1/16:1) | C34 H65 N O4 |
| Cer (t18:1/17:0) | C35 H69 N O4 |
| Cer (t18:1/18:0) | C36 H71 N O4 |
| Cer (t18:1/18:1) | C36 H69 N O4 |
| Cer (t18:1/18:2) | C36 H67 N O4 |
| Cer (t18:1/18:2) isomer | C36 H67 N O4 |
| Cer (t18:1/18:3) | C36 H65 N O4 |
| Cer (t18:1/18:4) | C36 H63 N O4 |
| Cer (t18:1/18:5) | C36 H61 N O4 |
| Cer (t18:1/19:0) | C37 H73 N O4 |
| Cer (t18:1/20:0) | C38 H75 N O4 |
| Cer (t18:1/20:3) | C38 H69 N O4 |
| Cer (t18:1/21:0) | C39 H77 N O4 |
| Cer (t18:1/22:0) | C40 H79 N O4 |
| Cer (t18:1/22:2) | C40 H75 N O4 |
| Cer (t18:1/22:3) | C40 H73 N O4 |
| Cer (t18:1/22:4) | C40 H71 N O4 |
| Cer (t18:1/23:0) | C41 H81 N O4 |
| Cer (t18:1/24:0) | C42 H83 N O4 |
| Cer (t18:1/24:1) | C42 H81 N O4 |
| Cer (t18:1/24:2) | C42 H79 N O4 |
| Cer (t18:1/25:0) | C43 H85 N O4 |
| Cer (t18:1/25:1) | C43 H83 N O4 |
| Cer (t18:1/25:2) | C43 H81 N O4 |
| Cer (t18:1/28:2) | C46 H87 N O4 |
| Cer (t19:1/18:2) | C37 H69 N O4 |
| Cer (t19:1/18:4) | C37 H65 N O4 |
| Cer (t19:1/24:3) | C43 H79 N O4 |
| Cer (t18:1/14:0(OH)) | C32 H63 N O5 |

TABLE 4-continued preferred ceramides in the ceramide portion

| Ceramide | Formula |
| --- | --- |
| Cer (t18:1/16:0(OH)) | C34 H67 N O5 |
| Cer (t18:1/17:1(OH)) | C35 H67 N O5 |
| Cer (t18:1/18:0(OH)) | C36 H61 N O5 |
| Cer (t18:1/18:1(OH)) | C36 H69 N O5 |
| Cer (t18:1/18:2(OH)) | C36 H67 N O5 |
| Cer (t18:1/20:0(OH)) | C38 H75 N O5 |
| Cer (t18:1/20:1(OH)) | C38 H73 N O5 |
| Cer (t18:1/21:0(OH)) | C39 H77 N O5 |
| Cer (t18:1/22:0(OH)) | C40 H79 N O5 |
| Cer (t18:1/22:1(OH)) | C40 H77 N O5 |
| Cer (t18:1/22:2(OH)) | C40 H75 N O5 |
| Cer (t18:1/23:0(OH)) | C41 H81 N O5 |
| Cer (t18:1/23:1(OH)) | C41 H79 N O5 |
| Cer (t18:1/24:0(OH)) | C42 H83 N O5 |
| Cer (t18:1/24:1(OH)) | C42 H81 N O5 |
| Cer (t18:1/24:2(OH)) | C42 H79 N O5 |
| Cer (t18:1/25:0(OH)) | C43 H85 N O5 |
| Cer (t18:1/25:1(OH)) | C43 H83 N O5 |
| Cer (t18:1/25:2(OH)) | C43 H81 N O5 |
| Cer (t18:1/26:0(OH)) | C44 H87 N O5 |
| Cer (t18:1/24:0(OH)) | C42 H83 N O5 |
| Cer (t19:1/16:0(OH)) | C35 H69 N O5 |
| Cer (t19:1/18:0(OH)) | C37 H73 N O5 |
| Cer (t14:1/25:5(tOH)) | C39 H67 N O7 |
| Cer (t14:1/22:1(tOH)) | C36 H69 N O7 |
| Cer (t18:1/23:5(tOH)) | C41 H71 N O7 |
| Cer (t20:0/33:5(tOH)) | C53 H95 N O7 |
| Cer (d16:0/35:1(dOH)) | C51 H101 N O5 |
| Cer (t14:1/16:1(dOH)) | C30 H57 N O6 |
| Cer (t14:1/16:0(dOH)) | C30 H59 N O6 |
| Cer (t14:1/22:1(dOH)) | C36 H69 N O6 |
| Cer (t14:1/24:3(dOH)) | C38 H69 N O6 |
| Cer (t14:1/25:3(dOH)) | C39 H71 N O6 |
| Cer (t14:1/26:0(dOH)) | C40 H79 N O6 |
| Cer (t18:0/23:4(dOH)) | C41 H75 N O6 |
| Cer (t18:0/42:1(dOH)) | C60 H117 N O6 |
| Cer (t18:1/24:0(dOH)) | C42 H83 N O6 |
| Cer (t18:1/29:2(dOH)) | C47 H89 N O6 |
| Cer (t18:1/42:1(dOH)) | C60 H115 N O6 |
| Cer (d18:2/16:1) | C34 H63 N O3 |
| Cer (d18:2/16:2) | C34 H61 N O3 |
| Cer (d18:2/16:3) | C34 H59 N O3 |
| Cer (d18:2/18:2) | C36 H65 N O3 |
| Cer (d18:2/18:3) | C36 H63 N O3 |
| Cer (d18:2/18:4) | C36 H61 N O3 |
| Cer (d18:2/20:4) | C38 H65 N O3 |
| Cer (d18:2/20:5) | C38 H63 N O3 |
| Cer (d18:2/21:6) | C39 H63 N O3 |
| Cer (d18:2/22:2) | C40 H73 N O3 |
| Cer (d18:2/22:3) | C40 H71 N O3 |
| Cer (d18:2/22:5) | C40 H67 N O3 |
| Cer (d18:2/23:2) | C41 H75 N O3 |
| Cer (d18:2/23:3) | C41 H73 N O3 |
| Cer (d18:2/23:5) | C41 H69 N O3 |
| Cer (d18:2/23:5) isomer | C41 H69 N O3 |
| Cer (d18:2/23:6) | C41 H67 N O3 |
| Cer (d18:2/24:2) | C42 H77 N O3 |
| Cer (d18:2/24:3) | C42 H75 N O3 |
| Cer (d18:2/24:5) | C42 H71 N O3 |
| Cer (d18:2/25:4) | C43 H75 N O3 |
| Cer (d18:2/25:5) | C43 H73 N O3 |
| Cer (d18:2/26:1) | C44 H83 N O3 |
| Cer (d18:2/26:4) | C44 H75 N O3 |
| Cer (d18:2/26:4) isomer | C44 H75 N O3 |
| Cer (d18:2/27:5) | C45 H77 N O3 |
| Cer (d18:2/27:6) | C45 H75 N O3 |
| Cer (d18:2/28:5) | C46 H79 N O3 |
| Cer (d18:2/29:5) | C47 H81 N O3 |
| Cer (d18:2/29:6) | C47 H79 N O3 |
| Cer (d18:2/32:5) | C50 H87 N O3 |
| Cer (d18:2/32:6) | C50 H85 N O3 |

More preferably, the ceramide portion comprises one or more of the ceramides of table 5:

TABLE 5 more preferred ceramides in the ceramide portion

| Ceramide | Formula |
| --- | --- |
| Cer (m14:2/18:2) | C32 H57 N O2 |
| Cer (m14:3/18:2) | C32 H55 N O2 |
| Cer (m14:3/18:2) isomer | C32 H55 N O2 |
| Cer (m14:3/24:1) | C38 H69 N O2 |
| Cer (m15:1/5:0) | C20 H39 N O2 |
| Cer (m15:2/18:2) | C33 H59 N O2 |
| Cer (m15:3/18:1) | C33 H59 N O2 |
| Cer (m16:3/18:1) | C34 H61 N O2 |
| Cer (m16:3/22:1) | C38 H69 N O2 |
| Cer (m18:2/3:0) | C21 H39 N O2 |
| Cer (m18:2/19:0) | C37 H71 N O2 |
| Cer (m18:3/18:1) | C36 H65 N O2 |
| Cer (m18:3/18:2) | C36 H63 N O2 |
| Cer (m18:5/5:0) | C23 H37 N O2 |
| Cer (m19:4/16:0) | C35 H63 N O2 |
| Cer (m19:3/17:0) | C35 H65 N O2 |
| Cer (d14:0/18:1) | C32 H63 N O3 |
| Cer (d14:0/22:0) | C36 H73 N O3 |
| Cer (d14:0/23:0) | C37 H75 N O3 |
| Cer (d16:0/22:0) | C38 H77 N O3 |
| Cer (d16:0/23:0) | C39 H79 N O3 |
| Cer (d20:0/25:0) | C45 H91 N O3 |
| Cer (d20:0/27:0) | C47 H95 N O3 |
| Cer (d22:0/26:0) | C48 H97 N O3 |
| Cer (d24:0/26:0) | C50 H101 N O3 |
| Cer (d25:0/24:0) | C49 H99 N O3 |
| Cer (d22:0/25:0(OH)) | C47 H95 N O4 |
| Cer (t14:0/14:0) | C28 H57 N O4 |
| Cer (t18:0/17:1) | C35 H69 N O4 |
| Cer (t18:0/19:1) | C37 H73 N O4 |
| Cer (t18:0/21:1) | C39 H77 N O4 |
| Cer (t18:0/24:2) | C42 H81 N O4 |
| Cer (t18:0/24:5) | C42 H75 N O4 |
| Cer (t18:0/26:5) | C44 H79 N O4 |
| Cer (t20:0/26:1) | C46 H91 N O4 |
| Cer (t20:0/30:1) | C50 H99 N O4 |
| Cer (t20:0/31:1) | C51 H101 N O4 |
| Cer (t22:0/26:1) | C48 H95 N O4 |
| Cer (t16:0/12:0(OH)) | C28 H57 N O5 |
| Cer (t18:0/17:0(OH)) | C35 H71 N O5 |
| Cer (t18:0/17:4(OH)) | C35 H63 N O5 |
| Cer (d14:1/18:2) | C32 H59 N O3 |
| Cer (d14:1/20:4) | C34 H59 N O3 |
| Cer (d14:2/18:2) | C32 H57 N O3 |
| Cer (d14:2/20:4) | C34 H57 N O3 |
| Cer (d14:2/20:5) | C34 H55 N O3 |
| Cer (d14:2/20:6) | C34 H53 N O3 |
| Cer (d14:2/24:3) | C38 H67 N O3 |
| Cer (d14:2/25:3) | C39 H69 N O3 |
| Cer (d14:2/26:3) | C40 H71 N O3 |
| Cer (d15:1/22:1) | C37 H71 N O3 |

TABLE 5-continued more preferred ceramides in the ceramide portion

| Ceramide | Formula |
| --- | --- |
| Cer (d15:2/22:1) | C37 H69 N O3 |
| Cer (d16:1/22:2) | C38 H71 N O3 |
| Cer (d16:2/22:2) | C38 H69 N O3 |
| Cer (d16:2/23:1) | C39 H73 N O3 |
| Cer (d16:2/23:2) | C39 H71 N O3 |
| Cer (d16:2/24:2) | C40 H73 N O3 |
| Cer (d18:1/23:5) | C41 H71 N O3 |
| Cer (d18:1/25:2) | C43 H81 N O3 |
| Cer (d18:1/25:4) | C43 H77 N O3 |
| Cer (d18:1/26:4) | C44 H77 N O3 |
| Cer (d18:1/26:4) isomer | C44 H77 N O3 |
| Cer (d18:1/27:5) | C45 H79 N O3 |
| Cer (d18:1/28:5) | C46 H81 N O3 |
| Cer (d18:1/29:5) | C47 H83 N O3 |
| Cer (d18:1/32:4) | C50 H91 N O3 |
| Cer (d19:2/16:1) | C35 H65 N O3 |
| Cer (d19:2/16:2) | C35 H63 N O3 |
| Cer (d19:2/18:3) | C37 H65 N O3 |
| Cer (d19:2/18:4) | C37 H63 N O3 |
| Cer (d19:2/20:4) | C39 H67 N O5 |
| Cer (d19:2/21:5) | C40 H67 N O3 |
| Cer (d19:2/22:1) | C41 H77 N O3 |
| Cer (d19:2/24:1) | C43 H81 N O3 |
| Cer (d19:2/24:2) | C43 H79 N O3 |
| Cer (d19:3/17:4) | C36 H59 N O3 |
| Cer (d20:1/26:2) | C46 H87 N O3 |
| Cer (d20:2/28:0) | C48 H93 N O3 |
| Cer (d21:1/28:0) | C49 H97 N O3 |
| Cer (d22:1/26:2) | C48 H91 N O3 |
| Cer (d22:1/27:2) | C49 H93 N O3 |
| Cer (d14:1/18:3(OH)) | C32 H57 N O4 |
| Cer (d14:2/14:3(OH)) | C28 H47 N O4 |
| Cer (d18:1/26:2(OH)) | C44 H83 N O4 |
| Cer (d19:2/25:2(OH)) | C44 H81 N O4 |
| Cer (d19:3/16:1(OH)) | C35 H63 N O4 |
| Cer (d20:1/26:2(OH)) | C46 H87 N O4 |
| Cer (d20:1/28:2(OH)) | C48 H91 N O4 |
| Cer (t18:1/16:1) | C34 H65 N O4 |
| Cer (t18:1/17:0) | C35 H69 N O4 |
| Cer (t18:1/18:1) | C36 H69 N O4 |
| Cer (t18:1/18:2) | C36 H67 N O4 |
| Cer (t18:1/18:2) isomer | C36 H67 N O4 |
| Cer (t18:1/18:3) | C36 H65 N O4 |
| Cer (t18:1/18:4) | C36 H63 N O4 |
| Cer (t18:1/18:5) | C36 H61 N O4 |
| Cer (t18:1/19:0) | C37 H73 N O4 |
| Cer (t18:1/20:3) | C38 H69 N O4 |
| Cer (t18:1/22:2) | C40 H75 N O4 |
| Cer (t18:1/22:3) | C40 H73 N O4 |
| Cer (t18:1/22:4) | C40 H71 N O4 |
| Cer (t18:1/24:2) | C42 H79 N O4 |
| Cer (t18:1/25:2) | C43 H81 N O4 |
| Cer (t18:1/28:2) | C46 H87 N O4 |
| Cer (t19:1/18:2) | C37 H69 N O4 |
| Cer (t19:1/18:4) | C37 H65 N O4 |
| Cer (t19:1/24:3) | C43 H79 N O4 |
| Cer (t18:1/14:0(OH)) | C32 H63 N O5 |
| Cer (t18:1/17:1(OH)) | C35 H67 N O5 |
| Cer (t18:1/18:1(OH)) | C36 H69 N O5 |
| Cer (t18:1/18:2(OH)) | C36 H67 N O5 |
| Cer (t18:1/20:1(OH)) | C38 H73 N O5 |
| Cer (t18:1/22:2(OH)) | C40 H75 N O5 |
| Cer (t18:1/24:2(OH)) | C42 H79 N O5 |
| Cer (t18:1/25:2(OH)) | C43 H81 N O5 |
| Cer (t19:1/16:0(OH)) | C35 H69 N O5 |
| Cer (t19:1/18:0(OH)) | C37 H73 N O5 |
| Cer (t14:1/25:5(tOH)) | C39 H67 N O7 |
| Cer (t14:1/22:1(tOH)) | C36 H69 N O7 |
| Cer (t18:1/23:5(tOH)) | C41 H71 N O7 |
| Cer (t20:0/33:5(tOH)) | C53 H95 N O7 |
| Cer (d16:0/35:1(dOH)) | C51 H101 N O5 |
| Cer (t14:1/16:1(dOH)) | C30 H57 N O6 |
| Cer (t14:1/16:0(dOH)) | C30 H59 N O6 |
| Cer (t14:1/22:1(dOH)) | C36 H69 N O6 |
| Cer (t14:1/24:3(dOH)) | C38 H69 N O6 |
| Cer (t14:1/25:3(dOH)) | C39 H71 N O6 |
| Cer (t14:1/26:0(dOH)) | C40 H79 N O6 |
| Cer (t18:0/23:4(dOH)) | C41 H75 N O6 |
| Cer (t18:0/42:1(dOH)) | C60 H117 N O6 |
| Cer (t18:1/29:2(dOH)) | C47 H89 N O6 |
| Cer (t18:1/42:1(dOH)) | C60 H115 N O6 |
| Cer (d18:2/16:2) | C34 H61 N O3 |
| Cer (d18:2/16:3) | C34 H59 N O3 |
| Cer (d18:2/18:3) | C36 H63 N O3 |
| Cer (d18:2/18:4) | C36 H61 N O3 |
| Cer (d18:2/20:4) | C38 H65 N O3 |
| Cer (d18:2/20:5) | C38 H63 N O3 |
| Cer (d18:2/21:6) | C39 H63 N O3 |
| Cer (d18:2/22:2) | C40 H73 N O3 |
| Cer (d18:2/22:3) | C40 H71 N O3 |
| Cer (d18:2/22:5) | C40 H67 N O3 |
| Cer (d18:2/23:2) | C41 H75 N O3 |
| Cer (d18:2/23:3) | C41 H73 N O3 |
| Cer (d18:2/23:5) | C41 H69 N O3 |
| Cer (d18:2/23:5) isomer | C41 H69 N O3 |
| Cer (d18:2/23:6) | C41 H67 N O3 |
| Cer (d18:2/24:3) | C42 H75 N O3 |
| Cer (d18:2/24:5) | C42 H71 N O3 |
| Cer (d18:2/25:4) | C43 H75 N O3 |
| Cer (d18:2/25:5) | C43 H73 N O3 |
| Cer (d18:2/26:1) | C44 H83 N O3 |
| Cer (d18:2/27:5) | C45 H77 N O3 |
| Cer (d18:2/27:6) | C45 H75 N O3 |
| Cer (d18:2/28:5) | C46 H79 N O3 |
| Cer (d18:2/29:5) | C47 H81 N O3 |
| Cer (d18:2/29:6) | C47 H79 N O3 |
| Cer (d18:2/32:5) | C50 H87 N O3 |
| Cer (d18:2/32:6) | C50 H85 N O3 |

In particular, the ceramide portion comprises all of the following ceramides:

Cer(m14:2/18:2) having Formula (6) with x=2, y=0, z=0, x'=11 and y'=2:

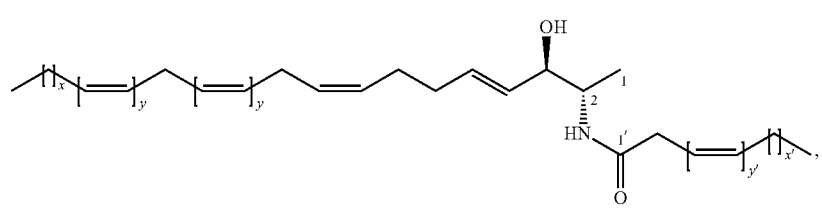

Formula (6)

Cer(m15:2/18:2) having Formula (6) as given above with x=3, y=0, z=0, x'=11 and y'=2,
Cer(m16:3/18:1) having Formula (6) as given above with x=2, y=0, z=1, x'=13 and y'=1,
Cer(m19:4/16:0) having Formula (6) as given above with x=3, y=1, z=1, x'=13 and y'=0,
Cer(d14:0/23:0) having Formula (7) with x=10 and x'=21:

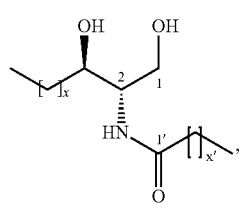

Formula (7)

Cer(d22:0/26:0) having Formula (7) given above with x=18 and x'=24,
Cer(d24:0/26:0) having Formula (7) given above with x=20 and x'=24,
Cer(d25:0/24:0) having Formula (7) given above with x=21 and x'=22,
Cer(t14:0/14:0) having Formula (8):

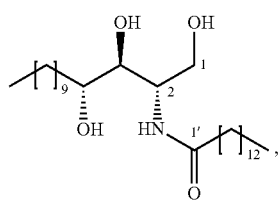

Formula (8)

Cer(d19:3/17:4) having Formula (9) with x=7, y=1, x'=5 and y'=4:

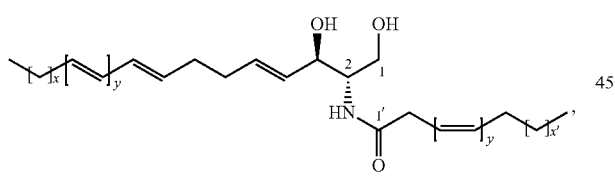

Formula (9)

Cer(d20:2/28:0) having Formula (9) given above with x=10, y=0, x'=24 and y'=0,
Cer(t14:1/22:1(tOH)) having Formula (10) with x=6, y=1, x'=14 and y'=1:

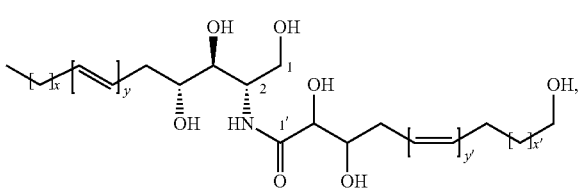

Formula (10)

Cer(t18:1/23:5(tOH)) having Formula (10) with x=10, y=1, x'=7 and y'=5,
Cer(t20:0/33:5(tOH)) having Formula (10) with x=14, y=0, x'=17 and y'=5, Cer(d16:0/35:1(dOH)) having Formula (11):

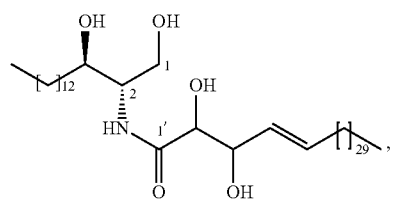

Formula (11)

Cer(t14:1/16:1(dOH)) having Formula (12) with x=6, y=1, x'=8 and y'=1:

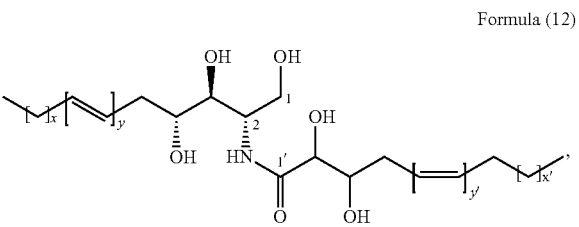

Formula (12)

Cer(t18:0/23:4(dOH)) having Formula (12) given above with x=12, y=0, x'=9 and y'=4,
Cer(t18:0/42:1(dOH)) having Formula (12) given above with x=12, y=0, x'=34 and y'=1,
Cer(t18:1/42:1(dOH)) having Formula (12) given above with x=10, y=1, x'=34 and y'=1, and
Cer(d18:2/32:6) having Formula (13):

Formula (13)

The third sphingolipid fraction preferably comprises the "glycosphingolipid portion", in particular it essentially consists of solvents and the glycosphingolipid portion, i.e. a portion with a high amount of glycosphingolipids, with preferably more than 50 wt.-%, in particular at least 70 wt.-% and more preferably more than 80 wt.-% of glycosphingolipids based on the weight of the glycosphingolipid portion. The glycosphingolipid portion preferably comprises one or more of the glycosphingolipids given in table 6:

TABLE 6

| preferred glycosphingolipids in the glycosphingolipid portion | |
|---|---|
| Glycosphingolipid | Formula |
| HexCer (d16:0/20:0) | C42 H83 N O8 |
| HexCer (d14:1/20:0) | C40 H77 N O8 |
| HexCer (d14:1/20:1) | C40 H75 N O8 |
| HexCer (d14:1/22:0) | C42 H81 N O8 |
| HexCer (d14:1/22:1) | C42 H79 N O8 |

TABLE 6-continued preferred glycosphingolipids in the glycosphingolipid portion

| Glycosphingolipid | Formula |
| --- | --- |
| HexCer (d14:2/20:1) | C40 H73 N O8 |
| HexCer (d14:2/22:1) | C42 H77 N O8 |
| HexCer (d14:2/23:1) | C43 H79 N O8 |
| HexCer (d14:2/24:1) | C44 H81 N O8 |
| HexCer (d16:1/20:0) | C42 H81 N O8 |
| HexCer (d16:1/20:1) | C42 H79 N O8 |
| HexCer (d16:2/20:1) | C42 H77 N O8 |
| HexCer (d16:2/22:1) | C44 H81 N O8 |
| HexCer (d18:1/16:0) | C40 H77 N O8 |
| HexCer (d18:2/16:0) | C40 H75 N O8 |
| HexCer (d18:2/16:1) | C40 H73 N O8 |
| HexCer (d18:2/24:1) | C48 H89 N O8 |
| HexCer (d19:2/16:0) | C41 H77 N O8 |
| HexCer (d19:2/18:1) | C43 H79 N O8 |
| HexCer (d19:2/18:2) | C43 H77 N O8 |
| HexCer (d19:2/24:1) | C49 H91 N O8 |
| HexCer (d19:3/16:0) | C41 H75 N O8 |
| HexCer (d14:1/22:0(OH)) | C42 H81 N O9 |
| HexCer (d16:1/20:0(OH)) | C42 H81 N O9 |
| HexCer (d16:1/22:0(OH)) | C44 H85 N O9 |
| HexCer (d16:1/22:3) | C44 H79 N O9 |
| HexCer (d16:1/23:4(OH)) | C45 H79 N O9 |
| HexCer (d16:2/22:3) | C44 H77 N O9 |
| HexCer (d16:2/24:3(OH)) | C46 H81 N O9 |
| HexCer (d18:2/15:1(OH)) | C39 H71 N O9 |
| HexCer (d18:2/16:1(OH)) | C40 H73 N O9 |
| HexCer (d18:2/24:0(OH)) | C48 H91 N O9 |
| HexCer (d19:2/16:0(OH)) | C41 H77 N O9 |
| HexCer (d19:2/16:1(OH)) | C41 H75 N O9 |
| HexCer (d19:2/16:1(OH)) Isomer | C41 H75 N O9 |
| HexCer (d19:2/17:0(OH)) | C42 H79 N O9 |
| HexCer (d19:2/17:1(OH)) | C42 H77 N O9 |
| HexCer (d19:2/17:3(OH)) | C42 H73 N O9 |
| HexCer (d19:2/18:0(OH)) | C43 H81 N O9 |
| HexCer (d19:2/18:1(OH)) | C43 H79 N O9 |
| HexCer (d19:2/18:3(OH)) | C43 H75 N O9 |
| HexCer (d19:2/19:2(OH)) | C44 H79 N O9 |
| HexCer (d19:2/19:3(OH)) | C44 H77 N O9 |
| HexCer (d19:2/22:0(OH)) | C47 H89 N O9 |
| HexCer (d19:2/24:0(OH)) | C49 H93 N O9 |
| HexCer (d19:2/24:1(OH)) | C49 H91 N O9 |
| HexCer (d19:3/16:1(OH)) | C41 H73 N O9 |
| HexCer (t18:0/24:0(OH)) | C48 H95 N O10 |
| HexCer (t18:1/20:1(OH)) | C44 H83 N O10 |
| HexCer (t18:1/23:0(OH)) | C47 H91 N O10 |
| HexCer (t18:1/24:0(OH)) | C48 H93 N O10 |
| HexCer (t18:1/25:0(OH)) | C49 H95 N O10 |
| HexCer (t19:1/16:1(OH)) | C41 H77 N O10 |
| HexCer (t19:1/19:3(OH)) | C44 H79 N O10 |
| HexCer (t19:2/16:1(OH)) | C41 H75 N O10 |
| Hex-HexCer (d14:1/20:0) | C46 H87 N O13 |
| Hex-HexCer (d14:1/22:0) | C48 H91 N O13 |
| Hex-HexCer (d14:2/20:1) | C46 H83 N O13 |
| Hex-HexCer (d14:2/22:1) | C48 H87 N O13 |
| Hex-HexCer (d14:2/24:3) | C50 H87 N O13 |
| Hex-HexCer (d14:1/22:0(OH)) | C48 H91 N O14 |
| Hex-HexCer (d14:1/22:0(OH)) isomer | C48 H91 N O14 |
| Hex-HexCer (d14:1/22:2(OH)) | C48 H85 N O14 |
| Hex-HexCer (d14:2/25:3(OH)) | C51 H89 N O14 |
| Hex-HexCer (d16:2/22:3(OH)) | C50 H87 N O14 |
| Hex-HexCer (t18:0/22:0(OH)) | C52 H101 N O15 |
| Hex-HexCer (t18:0/24:0(OH)) | C54 H105 N O15 |
| Hex-HexCer (t18:1/9:2(OH)) | C39 H69 N O15 |
| Hex-HexCer (t18:1/22:0(OH)) | C52 H99 N O15 |
| Hex-HexCer (t18:1/23:0(OH)) | C53 H101 N O15 |
| Hex-HexCer (t18:1/24:0(OH)) | C54 H103 N O15 |
| Hex-HexCer (d18:2/18:3(OH)) | C48 H83 N O14 |
| Hex-HexCer (d19:2/16:2) | C47 H83 N O13 |
| Hex-HexCer (d19:2/17:3) | C48 H83 N O13 |
| Fuc-Fuc-Hex-Cer (d14:0/20:0(OH)) | C52 H99 N O17 |
| Fuc-Fuc-Hex-Cer (d14:1/22:4(OH)) | C54 H93 N O17 |
| Hex-Fuc-Hex-Cer (d14:2/22:1) | C54 H97 N O17 |
| Fuc-Hex-Hex-Cer (d15:1/20:0(OH)) | C53 H99 N O18 |
| Fuc-Hex-Hex-Cer (d15:1/22:0(OH)) | C55 H103 N O18 |
| Fuc-Hex-Hex-Cer (d16:1/22:0(OH)) | C56 H105 N O18 |
| Hex-Hex-Fuc-Cer (d16:0/22:0) | C56 H107 N O17 |
| Fuc-Hex-Hex-Cer (d14:1/20:0) | C52 H97 N O17 |
| Fuc-Hex-Hex-Cer (d14:1/21:0) | C53 H99 N O17 |
| Fuc-Hex-Hex-Cer (d14:2/20:1) | C52 H93 N O17 |
| Fuc-Hex-Hex-Cer (d14:1/22:0) | C54 H101 N O17 |
| Fuc-Hex-Hex-Cer (d14:1/23:0) | C55 H103 N O17 |
| Fuc-Hex-Hex-Cer (d14:1/24:2) | C56 H101 N O17 |
| Fuc-Hex-Hex-Cer (d16:1/22:0) | C56 H105 N O17 |
| Fuc-Hex-Hex-Cer (d16:2/22:2) | C56 H99 N O17 |
| Fuc-Hex-Hex-Cer (d14:1/20:0(OH)) | C52 H97 N O18 |
| Fuc-Hex-Hex-Cer (d14:1/22:0(OH)) | C54 H101 N O18 |
| Fuc-Hex-Hex-Cer (d14:2/22:2(OH)) | C54 H95 N O18 |
| Fuc-Hex-Hex-Cer (d14:2/22:3(OH)) | C54 H93 N O18 |
| Fuc-Hex-Hex-Cer (d14:2/23:2(OH)) | C55 H97 N O18 |
| Fuc-Hex-Hex-Cer (d14:2/24:2(OH)) | C56 H99 N O18 |
| Fuc-Hex-Hex-Cer (d14:2/26:2(OH)) | C58 H103 N O18 |
| Fuc-Hex-Hex-Cer (d16:2/23:2(OH)) | C57 H101 N O18 |
| Fuc-Hex-Hex-Cer (d16:2/24:3(OH)) | C58 H101 N O18 |
| Fuc-Hex-GalNAc-Cer (t14:1/22:0) | C56 H104 N2 O18 |
| Hex-Hex-Hex-Cer (t18:1/22:0(OH)) | C58 H109 N O20 |
| HexCer (d15:1/20:0(OH)) | C41 H79 N O9 |
| Hex-HexCer (d14:1/20:0(OH)) | C46 H87 N O14 |
| Hex-HexCer (t18:1/24:1(OH)) | C54 H101 N O15 |

More preferably, the glycosphingolipid portion comprises one or more of the glycosphingolipids of table 7:

TABLE 7 more preferred glycosphingolipids in the glycosphingolipid portion

| Glycosphingolipid | Formula |
|---|---|
| HexCer (d16:0/20:0) | C42 H83 N O8 |
| HexCer (d14:1/20:1) | C40 H75 N O8 |
| HexCer (d14:1/22:1) | C42 H79 N O8 |
| HexCer (d14:2/20:1) | C40 H73 N O8 |
| HexCer (d14:2/22:1) | C42 H77 N O8 |
| HexCer (d14:2/23:1) | C43 H79 N O8 |
| HexCer (d14:2/24:1) | C44 H81 N O8 |
| HexCer (d16:2/20:1) | C42 H77 N O8 |
| HexCer (d16:2/22:1) | C44 H81 N O8 |
| HexCer (d18:2/16:1) | C40 H73 N O8 |
| HexCer (d19:2/18:2) | C43 H77 N O8 |
| HexCer (d19:2/24:1) | C49 H91 N O8 |
| HexCer (d16:2/22:3(OH)) | C44 H77 N O9 |
| HexCer (d16:2/24:3(OH)) | C46 H81 N O9 |
| HexCer (d18:2/15:1(OH)) | C39 H71 N O9 |
| HexCer (d19:2/17:1(OH)) | C42 H77 N O9 |
| HexCer (d19:2/17:3(OH)) | C42 H73 N O9 |
| HexCer (d19:2/18:3(OH)) | C43 H75 N O9 |
| HexCer (d19:2/19:2(OH)) | C44 H79 N O9 |
| HexCer (d19:2/19:3(OH)) | C44 H77 N O9 |
| HexCer (d19:3/16:1(OH)) | C41 H73 N O9 |
| HexCer (t19:1/16:1(OH)) | C41 H77 N O10 |
| HexCer (t19:1/19:3(OH)) | C44 H79 N O10 |
| HexCer (t19:2/16:1(OH)) | C41 H75 N O10 |
| Hex-HexCer (d14:1/20:0) | C46 H87 N O13 |
| Hex-HexCer (d14:2/20:1) | C46 H83 N O13 |
| Hex-HexCer (d14:2/22:1) | C48 H87 N O13 |
| Hex-HexCer (d14:1/22:0(OH)) | C48 H91 N O14 |
| Hex-HexCer (d14:1/22:0(OH)) isomer | C48 H91 N O14 |
| Hex-HexCer (d14:1/22:2(OH)) | C48 H85 N O14 |
| Hex-HexCer (d14:2/25:3(OH)) | C51 H89 N O14 |
| Hex-HexCer (d16:2/22:3(OH)) | C50 H87 N O14 |
| Hex-HexCer (t18:1/9:2(OH)) | C39 H69 N O15 |
| Hex-HexCer (d18:2/18:3(OH)) | C48 H83 N O14 |
| Hex-HexCer (d19:2/16:2) | C47 H83 N O13 |
| Hex-HexCer (d19:2/17:3) | C48 H83 N O13 |
| Fuc-Fuc-Hex-Cer (d14:0/20:0(OH)) | C52 H99 N O17 |
| Fuc-Fuc-Hex-Cer (d14:1/22:4(OH)) | C54 H93 N O17 |
| Hex-Fuc-Hex-Cer (d14:2/22:1) | C54 H97 N O17 |
| Fuc-Hex-Hex-Cer (d15:1/20:0(OH)) | C53 H99 N O18 |
| Fuc-Hex-Hex-Cer (d15:1/22:0(OH)) | C55 H103 N O18 |
| Fuc-Hex-Hex-Cer (d16:1/22:0(OH)) | C56 H105 N O18 |
| Hex-Hex-Fuc-Cer (d16:0/22:0) | C56 H107 N O17 |
| Fuc-Hex-Hex-Cer (d14:1/20:0) | C52 H97 N O17 |
| Fuc-Hex-Hex-Cer (d14:1/21:0) | C53 H99 N O17 |
| Fuc-Hex-Hex-Cer (d14:2/20:1) | C52 H93 N O17 |
| Fuc-Hex-Hex-Cer (d14:1/22:0) | C54 H101 N O17 |
| Fuc-Hex-Hex-Cer (d14:1/23:0) | C55 H103 N O17 |
| Fuc-Hex-Hex-Cer (d14:1/24:2) | C56 H101 N O17 |
| Fuc-Hex-Hex-Cer (d16:1/22:0) | C56 H105 N O17 |
| Fuc-Hex-Hex-Cer (d16:2/22:2) | C56 H99 N O17 |
| Fuc-Hex-Hex-Cer (d14:1/20:0(OH)) | C52 H97 N O18 |
| Fuc-Hex-Hex-Cer (d14:1/22:0(OH)) | C54 H101 N O18 |
| Fuc-Hex-Hex-Cer (d14:2/22:2(OH)) | C54 H95 N O18 |
| Fuc-Hex-Hex-Cer (d14:2/22:3(OH)) | C54 H93 N O18 |
| Fuc-Hex-Hex-Cer (d14:2/23:2(OH)) | C55 H97 N O18 |
| Fuc-Hex-Hex-Cer (d14:2/24:2(OH)) | C56 H99 N O18 |
| Fuc-Hex-Hex-Cer (d14:2/26:2(OH)) | C58 H103 N O18 |
| Fuc-Hex-Hex-Cer (d16:2/23:2(OH)) | C57 H101 N O18 |
| Fuc-Hex-Hex-Cer (d16:2/24:3(OH)) | C58 H101 N O18 |
| Fuc-Hex-GalNAc-Cer (t14:1/22:0) | C56 H104 N2 O18 |
| Hex-Hex-Hex-Cer (t18:1/22:0(OH)) | C58 H109 N O20 |
| HexCer (d15:1/20:0(OH)) | C41 H79 N O9 |
| Hex-HexCer (d14:1/20:0(OH)) | C46 H87 N O14 |
| Hex-HexCer (t18:1/24:1(OH)) | C54 H101 N O15 |

In particular, the glycosphingolipid portion comprises all of the following glycosphingolipids:

HexCer(t19:1/16:1(OH)) having Formula (14) with $x=11$ and $y=0$ and wherein R=-Hex group:

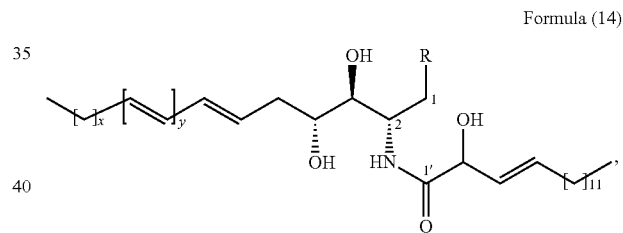

Formula (14)

HexCer(t19:2/16:1(OH)) having Formula (14) given above with $x=9$ and $y=1$ and wherein R=-Hex group, Hex-Hex-Cer(d14:2/20:1) having Formula (15) with $x=4$, $x'=14$, $y'=1$ and R'=H and wherein R=-Hex-Hex group:

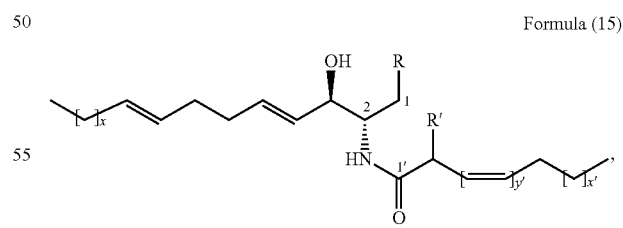

Formula (15)

Hex-Hex-Cer(d16:2/22:3(OH)) having Formula (15) given above with $x=6$, $x'=12$, $y'=3$ and R'=OH and wherein R=-Hex-Hex group, Hex-Hex-Cer(d19:2/16:2) having Formula (15) given above with $x=9$, $x'=8$, $y'=2$ and R'=H and wherein R=-Hex-Hex group, Fuc-Fuc-Hex-Cer(d14:0/20:0(OH)) having Formula (16) with R=-Hex-Fuc-Fuc group:

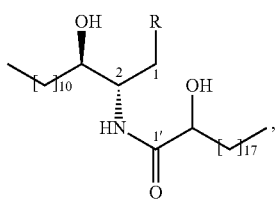

Fuc-Hex-Hex-Cer(d15:1/22:0(OH)) having Formula (17) with R=-Hex-Hex-Fuc group:

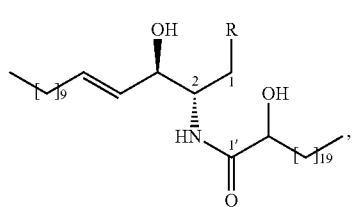

Hex-Hex-Hex-Cer(t18:1/22:0(OH)) having Formula (18) with R=-Hex-Hex-Hex group:

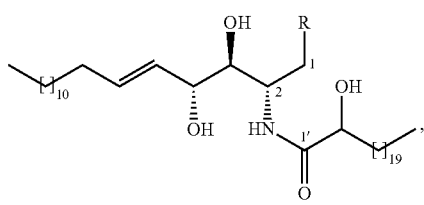

HexCer(d15:1/20:0(OH)) having Formula (19) and wherein R=-Hex group:

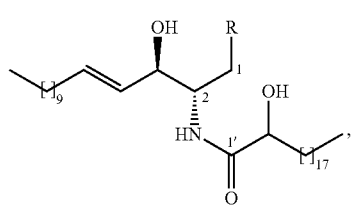

Hex-Hex-Fuc-Cer(d16:0/22:0) having Formula (20) with R=-Fuc-Hex-Hex group:

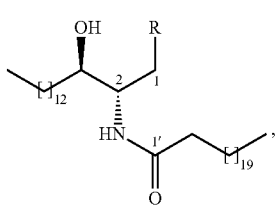

Hex-Hex-Cer(d14:1/20:0(OH) having Formula (21) with x=6, x'=16, y'=0 and R'=H and wherein R=-Hex-Hex group:

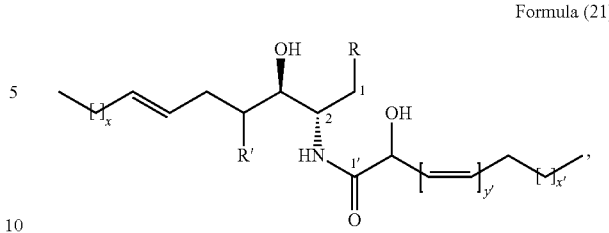

and

Hex-Hex-Cer(t18:1/24:1(OH)) having Formula (21) given above with x=10, x'=18, y'=1 and R'=OH and wherein R=-Hex-Hex group.

The fourth sphingolipid fraction preferably comprises the "phosphosphingolipid portion", in particular it essentially consists of solvents and the phosphosphingolipid portion, i.e. a portion with a high amount of phosphosphingolipids in particular of sphingomyelins, i.e. with preferably more than 50 wt.-%, in particular at least 70 wt.-% and more preferably more than 80 wt.-% of phosphosphingolipids based on the weight of the phosphosphingolipid portion, in particular with more than 50 wt.-%, in particular at least 70 wt.-% and more preferably more than 80 wt.-% of sphingomyelins (referenced as "sphingomyelin portion"). The phosphosphingolipid portion preferably comprises one or more of the phosphosphingolipids given in table 8:

TABLE 8 preferred phosphosphingolipids in the phosphosphingolipid portion

| Sphingomyelin | Formula |
|---|---|
| SM (d14:0/18:0) | C37 H77 N2 O6 P |
| SM (d14:0/20:0) | C39 H81 N2 O6 P |
| SM (d14:1/18:0) | C37 H75 N2 O6 P |
| SM (d14:1/19:0) | C38 H77 N2 O6 P |
| SM (d14:1/20:0) | C39 H79 N2 O6 P |
| SM (d14:1/21:0) | C40 H81 N2 O6 P |
| SM (d14:1/22:0) | C41 H83 N2 O6 P |
| SM (d14:1/23:0) | C42 H85 N2 O6 P |
| SM (d14:1/24:0) | C43 H87 N2 O6 P |
| SM (d14:1/26:0) | C45 H91 N2 O6 P |
| SM (d14:2/19:0) | C38 H75 N2 O6 P |
| SM (d14:2/22:0) | C41 H81 N2 O6 P |
| SM (d14:2/24:0) | C39 H77 N2 O6 P |
| SM (d15:1/8:0) | C28 H57 N2 O6 P |
| SM (d15:1/20:0) | C40 H81 N2 O6 P |
| SM (d15:1/22:0) | C42 H85 N2 O6 P |
| SM (d15:1/24:0) | C44 H89 N2 O6 P |
| SM (d15:1/27:1) | C47 H93 N2 O6 P |
| SM (d15:2/20:0) | C40 H79 N2 O6 P |
| SM (d15:2/22:0) | C42 H83 N2 O6 P |
| SM (d16:2/18:2) | C39 H73 N2 O6 P |
| SM (d16:2/22:0) | C43 H85 N2 O6 P |
| SM (d18:1/16:0) | C39 H79 N2 O6 P |
| SM (d18:1/18:0) | C41 H83 N2 O6 P |
| SM (d18:1/20:0) | C43 H87 N2 O6 P |
| SM (d18:1/22:0) | C45 H91 N2 O6 P |
| SM (d18:2/22:0) | C45 H89 N2 O6 P |
| SM (d18:2/23:0) | C46 H91 N2 O6 P |
| SM (d14:0/27:2(OH)) | C46 H91 N2 O7 P |
| SM (d14:1/21:0(OH)) | C40 H81 N2 O7 P |
| SM (d14:2/21:0(OH)) | C40 H79 N2 O7 P |
| SM (d14:2/22:0(OH)) | C41 H81 N2 O7 P |
| SM (d14:2/22:0(OH)) Isomer | C41 H81 N2 O7 P |
| SM (d16:2/22:0(OH)) | C43 H85 N2 O7 P |
| SM (d17:1/16:0(OH)) | C38 H77 N2 O7 P |
| SM (d18:1/16:0(OH)) | C39 H79 N2 O7 P |
| SM (d18:1/16:1(OH)) | C39 H77 N2 O7 P |
| SM (d18:2/16:0(OH)) | C39 H77 N2 O7 P |

TABLE 8-continued preferred phosphosphingolipids in the phosphosphingolipid portion

| Sphingomyelin | Formula |
|---|---|
| SM (d19:2/16:0(OH)) | C40 H79 N2 O7 P |
| SM (d19:2/16:1(OH)) | C40 H77 N2 O7 P |
| SM (t14:1/18:0) | C37 H75 N2 O7 P |
| SM (t16:0/18:0) | C39 H81 N2 O7 P |
| SM (t16:1/20:0) | C41 H83 N2 O7 P |
| SM (t14:0/25:3(OH)) | C44 H85 N2 O8 P |
| SM (t16:0/24:3(OH)) | C45 H87 N2 O8 P |
| SM (t14:1/23:0(OH)) | C42 H85 N2 O8 P |
| SM (t14:1/26:3(OH)) | C45 H85 N2 O8 P |
| SM (t14:1/27:3(OH)) | C46 H87 N2 O8 P |
| SM (t19:1/16:0(OH)) | C40 H81 N2 O8 P |
| SM (t18:0/24:1(OH)) | C47 H95 N2 O8 P |
| SM (d22:0) | C27 H57 N2 O6 P |
| SM (d30:0) | C35 H73 N2 O6 P |
| SM (d33:0) | C38 H79 N2 O6 P |
| SM (d36:0) | C41 H85 N2 O6 P |
| SM (d37:0) | C42 H87 N2 O6 P |
| SM (d38:0) | C43 H89 N2 O6 P |
| SM (d40:0) | C45 H93 N2 O6 P |
| SM (d41:1) | C46 H93 N2 O6 P |
| SM (d42:1) | C47 H95 N2 O6 P |
| SM (d44:3) | C49 H95 N2 O6 P |
| SM (d44:3) Isomer | C49 H95 N2 O6 P |
| SM (d46:3) | C51 H99 N2 O6 P |
| SM (t23:1) | C28 H57 N2 O7 P |
| SM (t25:1) | C30 H61 N2 O7 P |
| SM (t34:2) | C39 H77 N2 O7 P |
| SM (t38:0) | C43 H89 N2 O7 P |
| SM (t40:0) | C45 H93 N2 O7 P |
| SM (t41:0) | C46 H95 N2 O7 P |
| SM (t42:0) | C47 H97 N2 O7 P |
| SM (q26:2) | C31 H61 N2 O8 P |
| SM (q27:2) | C32 H63 N2 O8 P |
| SM (q27:1) | C32 H65 N2 O8 P |
| SM (q28:2) | C33 H65 N2 O8 P |
| SM (q29:2) | C34 H67 N2 O8 P |
| SM (q34:1) | C39 H79 N2 O8 P |
| SM (q34:1) isomer | C39 H79 N2 O8 P |
| SM (q41:3) | C46 H89 N2 O8 P |

More preferably, the phosphosphingolipid portion comprises one or more of the phosphosphingolipids of table 9:

TABLE 9 more preferred phosphosphingolipids in the phosphosphingolipid portion

| Sphingomyelin | Formula |
|---|---|
| SM (d14:0/18:0) | C37 H77 N2 O6 P |
| SM (d14:0/20:0) | C39 H81 N2 O6 P |
| SM (d14:1/18:0) | C37 H75 N2 O6 P |
| SM (d14:1/19:0) | C38 H77 N2 O6 P |
| SM (d14:1/20:0) | C39 H79 N2 O6 P |
| SM (d14:1/21:0) | C40 H81 N2 O6 P |
| SM (d14:1/23:0) | C42 H85 N2 O6 P |
| SM (d14:1/24:0) | C43 H87 N2 O6 P |
| SM (d14:1/26:0) | C45 H91 N2 O6 P |
| SM (d14:2/19:0) | C38 H75 N2 O6 P |
| SM (d14:2/22:0) | C41 H81 N2 O6 P |
| SM (d15:1/8:0) | C28 H57 N2 O6 P |
| SM (d15:1/20:0) | C40 H81 N2 O6 P |
| SM (d15:1/22:0) | C42 H85 N2 O6 P |
| SM (d15:1/24:0) | C44 H89 N2 O6 P |
| SM (d15:1/27:1) | C47 H93 N2 O6 P |
| SM (d15:2/20:0) | C40 H79 N2 O6 P |
| SM (d15:2/22:0) | C42 H83 N2 O6 P |
| SM (d16:2/18:2) | C39 H73 N2 O6 P |
| SM (d16:2/22:0) | C43 H85 N2 O6 P |
| SM (d14:0/27:2(OH)) | C46 H91 N2 O7 P |
| SM (d14:1/21:0(OH)) | C40 H81 N2 O7 P |
| SM (d14:2/21:0(OH)) | C40 H79 N2 O7 P |
| SM (d14:2/22:0(OH)) | C41 H81 N2 O7 P |

TABLE 9-continued more preferred phosphosphingolipids in the phosphosphingolipid portion

| Sphingomyelin | Formula |
|---|---|
| SM (d14:2/22:0(OH)) Isomer | C41 H81 N2 O7 P |
| SM (d17:1/16:0(OH)) | C38 H77 N2 O7 P |
| SM (d18:2/16:0(OH)) | C39 H77 N2 O7 P |
| SM (d19:2/16:0(OH)) | C40 H79 N2 O7 P |
| SM (d19:2/16:1(OH)) | C40 H77 N2 O7 P |
| SM (t14:1/18:0) | C37 H75 N2 O7 P |
| SM (t16:0/18:0) | C39 H81 N2 O7 P |
| SM (t16:1/20:0) | C41 H83 N2 O7 P |
| SM (t14:0/25:3(OH)) | C44 H85 N2 O8 P |
| SM (t16:0/24:3(OH)) | C45 H87 N2 O8 P |
| SM (t14:1/23:0(OH)) | C42 H85 N2 O8 P |
| SM (t14:1/26:3(OH)) | C45 H85 N2 O8 P |
| SM (t14:1/27:3(OH)) | C46 H87 N2 O8 P |
| SM (t19:1/16:0(OH)) | C40 H81 N2 O8 P |
| SM (t18:0/24:1(OH)) | C47 H95 N2 O8 P |

In particular, the phosphosphingolipid portion comprises all of the following sphingomyelins:

SM(d14:0/18:0) having Formula (22) with x=8, y=0, z=0, x'=15 and R'=H:

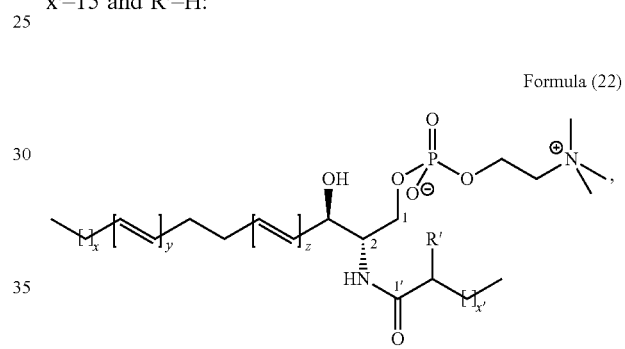

Formula (22)

SM(d14:1/18:0) having Formula (22) given above with x=6, y=0, z=1, x'=15 and R'=H, SM(d14:2/19:0) having Formula (22) given above with x=4, y=1, z=1, x'=16 and R'=H, SM(d15:1/20:0) having Formula (22) given above with x=7, y=0, z=1, x'=17 and R'=H, SM(d15:2/20:0) having Formula (22) given above with x=5, y=1, z=1, x'=17 and R'=H, SM(d19:2/16:0(OH)) having Formula (22) given above with x=9, y=1, z=1, x'=13 and R'=OH, SM(t14:1/18:0) having Formula (23) with x=6, y=1, x'=14, y'=0 and R'=H:

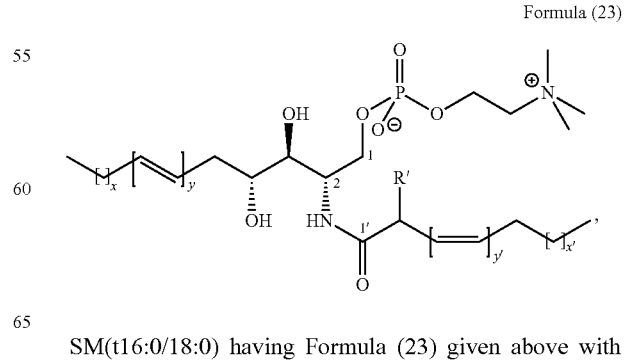

Formula (23)

SM(t16:0/18:0) having Formula (23) given above with x=10, y=0, x'=14, y'=0 and R'=H, SM(t16:1/20:0) having Formula (23) given above with x=8, y=1, x'=16, y'=0 and R'=H,
SM(t14:0/25:3(OH)) having Formula (23) given above with x=8, y=0, x'=15, y'=3 and R'=OH,
SM(t19:1/16:0(OH)) having Formula (23) given above with x=11, y=1, x'=12, y'=0 and R'=OH, and
SM(t18:0/24:1(OH)) having Formula (24):

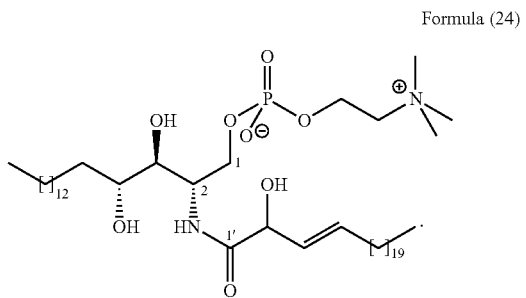

Formula (24)

In preferred embodiments of the present invention, one of
the ceramide portion,
the glycosphingolipid portion, or
the phosphosphingolipid portion
is isolated from *Cordyceps*, in particular from wild-type *Cordyceps*.

Step (ii) may further comprise a step of removing solvents from the first, second, third and/or fourth sphingolipid fraction in particular by drying with a stream of nitrogen and/or vacuum drying in particular with a centrifugal vacuum concentrator like SpeedVac™ to form the sphingolipid portion.

The method of isolating sphingolipids from *Cordyceps* preferably further comprises the following steps after step (ii):
(iii) subjecting the at least one sphingolipid portion to liquid chromatography, in particular ultrahigh pressure liquid chromatography; and optionally
(iv) performing a mass spectrometry following step (iii).
In particular, steps (iii) and (iv) comprise:
(iii) subjecting the at least one sphingolipid portion to liquid chromatography with a mobile phase comprising at least a first and a second eluting solvent, wherein the at least first and second eluting solvent comprise a mixture of at least one aliphatic alcohol, at least one carboxylic acid and at least one carboxylic acid salt and wherein the second eluting solvent has a higher total amount of aliphatic alcohol compared to the first eluting solvent; and optionally
(iv) performing a mass spectrometry following step (iii).

Steps (iii) and (iv) further allow for identifying the sphingolipids in the at least one sphingolipid portion.

Step (iii) may further include a step of reconstituting the sphingolipid portion in a reconstitution solvent before carrying out the liquid chromatography and optionally subsequently filtering the mixture, preferably with a filter having a pore size of at most 0.30 µm, further preferably at most 0.25 µm and in particular about 0.22 µm. The reconstitution solvent preferably comprises and most preferably consists of an aliphatic alcohol, in particular a monohydric aliphatic alcohol having 1 to 4 carbon atoms, most preferably methanol.

The liquid chromatography as used herein refers to a chromatography with a substance to be determined in the liquid, i.e. mobile phase, and an additional solid phase, usually a column. The skilled person is aware of this term and how to carry out a liquid chromatography. The liquid chromatography is preferably a high pressure liquid chromatography (HPLC), more preferably an ultrahigh pressure liquid chromatography (UHPLC, also known as UPLC, RRLC, RSLC or UFLC). The terms high pressure liquid chromatography and ultrahigh pressure liquid chromatography are used for specific subtypes of liquid column chromatography. The skilled person is aware of said terms and how to carry out such subtypes of chromatography.

In preferred embodiments, in step (iii) and step (iv) a liquid chromatography coupled to a mass spectrometer is used, i.e. LC-MS such as commercially available, in particular LC-ESI-MS or LC-ESI-MS/MS. Thus, LC for separating the sphingolipids in the sphingolipid portion is applied, wherein the separated sphingolipids are then automatically introduced in a mass spectrometer. Preferably, UHPLC, coupled to a mass spectrometer such as UHPLC-Q-TOF-MS and/or UHPLC-QQQ-MS is used in step (iii) and step (iv). Preferably, single MS mode or a MS/MS mode can be used in step (iv), preferably MS/MS mode and most preferably based on ESI. I.e. preferably coupled UHPLC-Q-TOF like UHPLC-iFunnel-Q-TOF and/or coupled UHPLC-QQQ is applied in step (iii) and step (iv).

Steps (iii) and (iv) can be carried out as described in Wang, J. R. et al., *Anal. Chem.* 2014, 86, 5688-5696 which is included herein by reference. Preferably, a $C_{18}$ column is used as stationary phase, i.e. a column comprising straight chain $C_{18}$ alkyl groups, i.e. the substances in the stationary phase contain 18 carbon atoms. Preferably, a $C_{18}$ column with dimensions of about 100 mm×2.1 mm and a particle size of about 1.8 µm is used, more preferably an Agilent Eclipse Plus $C_{18}$ column. Preferably, the UHPLC system is equipped with a binary solvent delivery system and a standard autosampler, more preferably the Agilent 1290 Infinity UHPLC system is used in step (iii).

The mobile phase in step (iii) comprises and preferably consists of the at least first and second eluting solvent. The first and the second eluting solvent independent from each other comprise at least one aliphatic alcohol, in particular a monohydric aliphatic alcohol having of 1 to 4 carbon atoms, preferably a straight chain or branched alkane in which one hydrogen atom is substituted with a hydroxyl group. The aliphatic alcohol of the first and second eluting solvent in step (iii) is more preferably independently selected from methanol, ethanol, propanol, isopropanol, n-butanol, isobutanol, sec-butyl alcohol or tert-butyl alcohol. Most preferably, the aliphatic alcohol of the first and second eluting solvent is independently selected from methanol or isopropanol. Most preferably, the first eluting solvent in step (iii) comprises methanol as aliphatic alcohol, preferably does not comprise a further aliphatic alcohol. Most preferably, the second eluting solvent comprises methanol as first aliphatic alcohol and isopropanol as second aliphatic alcohol.

The first and second eluting solvent in step (iii) independently from each other further comprise at least one carboxylic acid, in particular a hydrocarbon such as a branched or straight chain alkane, wherein at least one carbon atoms forms a carboxyl group. Preferably, the carboxylic acid is based on a straight chain alkane with 1 to 4 carbon atoms more preferably 1 to 2 carbon atoms, wherein at least one carbon atom forms a carboxyl group, preferably one carbon atom forms a carboxyl group. More preferably, the carboxylic acid in the first and second eluting solvent is formic acid.

The first and second eluting solvent in step (iii) preferably further comprise a carboxylic acid salt, namely a metal salt of a carboxylic acid, in particular an ammonium salt of a carboxylic acid of a branched or straight chain carboxylic acid with 1 to 4, more preferably 1 to 2 carbon atoms. Most preferably, the carboxylic acid salt is ammonium acetate.

More preferably, the first eluting solvent in step (iii) comprises methanol, $H_2O$, formic acid and ammonium acetate. The second eluting solvent most preferably comprises methanol, isopropanol, formic acid and ammonium acetate.

In particular embodiments, the first eluting solvent in step (iii) comprises and in particular consists of methanol, $H_2O$ and formic acid (60:40:0.2, v/v/v) and 10 mM ammonium acetate and the second eluting solvent comprises and in particular consists of methanol, isopropanol, and formic acid (60:40:0.2, v/v/v) and 10 mM ammonium acetate.

Preferably, a linear gradient is applied in step (iii) preferably with increasing amounts of the second eluting solvent. In most preferred embodiments, the linear gradient given in table 10 is applied:

TABLE 10 preferred linear gradient applied in step (iii)

| time (min) | amount of second eluting solvent in mobile phase |
|---|---|
| 0-3 | 0-10% |
| 3-5 | 10-40% |
| 5-5.3 | 40-55% |
| 5.3-8 | 55-60% |
| 8-8.5 | 60-80% |
| 8.5-10.5 | 80% |
| 10.5-16 | 80-90% |
| 16-19 | 90% |
| 19-22 | 90-100% |
| 22-26 | 100% |
| subsequently | equilibration with 0% |

The injection volume in step (iii) is in particular between 1 µL and 3 µL, preferably about 2 µL. The temperature is preferably 35° C. to 45° C., more preferably about 40° C. The run time is preferably at least 15 min, in particular about 26 min. The flow rate is preferably about 0.35 mL/min. The mass spectrometry in step (iv) preferably comprises a Q-TOF mass spectrometry, i.e. quadrupole time-of-flight mass spectrometry and/or QQQ mass spectrometry, i.e. triple-quadrupole mass spectrometry. In particular an MS/MS mode is used, also named tandem mass spectrometry mode, which is known to the skilled person. In especially preferred embodiments, mass spectrometry comprises the application of the jet stream technology known to the skilled person, in particular it comprises the application of an Agilent ultrahigh definition 6550 iFunnel-Q-TOF mass spectrometer. Preferably, a soft ionization method, in particular electrospray ionization (ESI) is used.

In preferred embodiments, the following conditions are applied for the Q-TOF mass spectrometry in step (iv):

as parameters for the jet stream a superheated ($N_2$) sheath gas temperature of 350° C. to 450°, preferably of about 400° C.; and/or preferably a flow rate of 8 L/min to 13 L/min, preferably of about 12 L/min; and/or as preferred electrospray ionization conditions in particular a positive ion mode, a capillary voltage of 3500 V to 4500 V, preferably of about 4000 V, a nozzle voltage of 100 to 500 V, preferably of about 300 V, a nebulizer pressure of 25 psi to 45 psi, preferably of about 40 psi (0.27579 MPa), a drying gas flow of about 5 L/min to 11 L/min, preferably of about 6 L/min, a drying gas temperature of 250° C. to 350° C., preferably of about 300° C.; and preferably a skimmer voltage of about 55 V to 75 V, preferably of about 65 V, an octapole RF peak voltage of 450 V to 550 V, preferably of about 500 V and a fragmentor voltage of about 100 V to 200 V, in particular of about 150 V.

Targeted MS/MS collision energies (CE) are preferably from 10-60 eV. The mass spectra are preferably recorded at the range m/z 200-1700, MS/MS spectra preferably across the range of m/z 40-1700. Preferably, full-scan and MS/MS data are processed with suitable software such as Agilent Mass Hunter Workstation Software and the results are compared with respective sphingolipid databases and/or with the data in table 11 or alternatively by comparing the results with respective standards. Preferred conditions for UHPLC-Q-TOF-MS are given in table 11 further below.

Optionally, the method comprises a further step of (v) verifying the identification of the sphingolipids in the at least one sphingolipid portion by means of lipid chromatography, in particular UHPLC and preferably comparing the obtained retention time with reference values like standards.

In another aspect, the present invention refers to a sphingolipid selected from one of the sphingolipids of tables 3, 5, 7 or 9.

Further in accordance with the present invention is a composition, preferably a pharmaceutical composition comprising and in particular essentially consisting of:

at least one sphingolipid portion, in particular one sphingolipid portion, in particular as pharmaceutically effective ingredient, isolated from *Cordyceps* according to the method described above, and at least one pharmaceutically tolerable excipient such as one or more of a diluent, a filler, a binder, a disintegrant, a lubricant, a coloring agent, a surfactant and a preservative.

Preferably, the *Cordyceps* is wild-type *Cordyceps*. The sphingolipid portion comprised in the composition is in particular one of the sphingoid base portion, the ceramide portion, the glycosphingolipid portion or the phosphosphingolipid portion isolated with the method as described above. More preferably, the sphingolipid portion comprised in the composition is selected from the sphingoid base portion, the ceramide portion or the glycosphingolipid portion. Most preferably, the sphingolipid portion comprised in the composition is selected from the sphingoid base portion or the ceramide portion, in particular it is the sphingoid base portion.

I.e. most preferably, the sphingolipid portion is the sphingoid base portion comprising:

So (d18:5) having the following Formula (3) with x=1 and y=2:

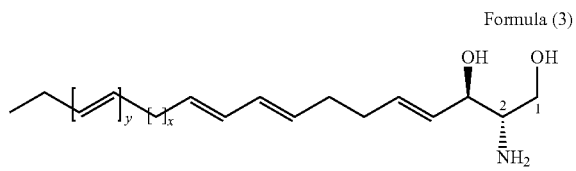

Formula (3)

So(d20:3) having Formula (3) as given above with x=7 and y=0,

So(d22:5) having Formula (3) as given above with x=5 and y=2,

So(t15:2) having Formula (4) with x=4 and y=0:

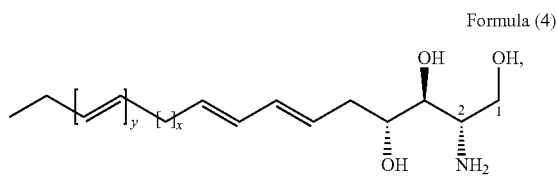

Formula (4)

So(t15:3) having Formula (4) as given above with x=2 and y=1,
So(t19:2) having Formula (4) as given above with x=8 and y=0,
So(t21:3) having Formula (4) as given above with x=8 and y=1,
So(t21:4) having Formula (4) as given above with x=6 and y=2,
So(m22:1) having Formula (5) with x=12, y=0 and z=0:

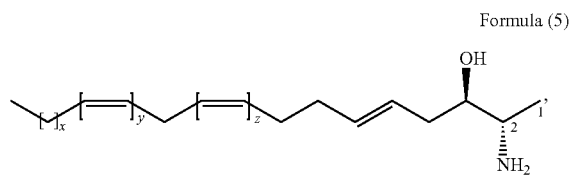

Formula (5)

So(m22:2) having Formula (5) as given above with x=10, y=0 and z=1, and
So(m22:3) having Formula (5) as given above with x=8, y=1 and z=1.

The sphingolipid portion is contained in the composition, in particular the pharmaceutical composition, preferably in an effective amount, i.e. an amount suitable to treat or prevent a disease in a subject, in particular a human, which also depends on the frequency and number of compositions to be administered.

The skilled person is able to select suitable pharmaceutically tolerable excipients depending on the form of the pharmaceutical composition and is aware of methods for manufacturing pharmaceutical compositions as well as able to select a suitable method for preparing the pharmaceutical composition depending on the kind of pharmaceutically tolerable excipients and the form of the pharmaceutical composition.

The pharmaceutical composition according to the invention can be present in solid, semisolid or liquid form to be administered by an oral, rectal, topical, parenteral or transdermal or inhalative route to a subject, preferably a human.

The pharmaceutical composition may comprise further pharmaceutical effective ingredients such as therapeutic compounds used for treating inflammatory diseases.

Further in accordance with the present invention is a method of treating a subject suffering from an inflammatory disease comprising administering an effective amount of at least one sphingolipid portion isolated from *Cordyceps*, in particular from wild-type *Cordyceps*, according to the method described above to the subject.

In particular, the method comprises administering an effective amount of one of the sphingoid base portion, the ceramide portion, the glycosphingolipid portion or the phosphosphingolipid portion isolated with the method as described above. More preferably, the method comprises administering an effective amount of one of the sphingoid base portion, the ceramide portion or the glycosphingolipid portion. Most preferably, the method comprises administering an effective amount of the sphingoid base portion or the ceramide portion, in particular of the sphingoid base portion isolated with the method as described above.

I.e. most preferably, the method comprises administering an effective amount of the sphingoid base portion comprising:

So (d18:5) having the following Formula (3) with x=1 and y=2:

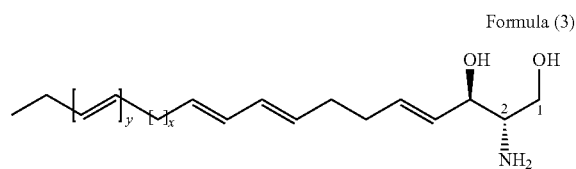

Formula (3)

So(d20:3) having Formula (3) as given above with x=7 and y=0,
So(d22:5) having Formula (3) as given above with x=5 and y=2,
So(t15:2) having Formula (4) with x=4 and y=0:

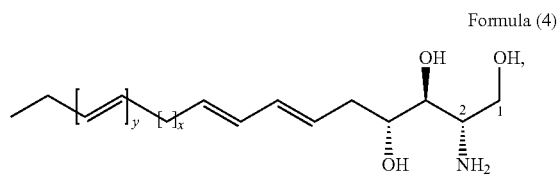

Formula (4)

So(t15:3) having Formula (4) as given above with x=2 and y=1,
So(t19:2) having Formula (4) as given above with x=8 and y=0,
So(t21:3) having Formula (4) as given above with x=8 and y=1,
So(t21:4) having Formula (4) as given above with x=6 and y=2,
So(m22:1) having Formula (5) with x=12, y=0 and z=0:

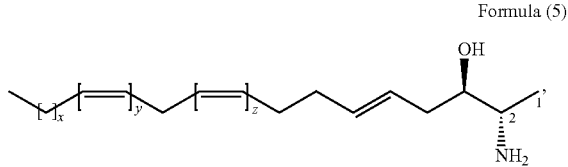

Formula (5)

So(m22:2) having Formula (5) as given above with x=10, y=0 and z=1, and
So(m22:3) having Formula (5) as given above with x=8, y=1 and z=1.

The subject is an animal or human, preferably it is a mammal and most preferably a human. The expression "effective amount" generally denotes an amount sufficient to produce therapeutically desirable results, wherein the exact nature of the result varies depending on the specific disorder which is treated. When the disorder is an inflammatory disease, the result is usually an inhibition or suppression of the immune response and/or an amelioration of accompanying symptoms.

The effective amount of the sphingolipid portion isolated from *Cordyceps* may depend on the $IC_{50}$, the species, body weight, age and individual conditions of the subject and can be determined by standard procedures such as with cell cultures or experimental animals. The concentration of the sphingolipid portion from *Cordyceps* administered may be between 0.001 µM and 10 µM or up to 600 µg/mL, for example, up to 100 µg/mL like 1 µg/mL to 50 µg/mL.

The inflammatory disease can be selected from an autoimmune disease or an allergic disease. Alternatively, the at least one sphingolipid portion may be used for preventing or reducing organ transplant rejection. Hence, the present invention alternatively refers to a method of preventing and/or reducing organ transplant rejection in a subject, in particular a human, comprising administering at least one sphingolipid portion isolated from *Cordyceps*, in particular from wild-type *Cordyceps*, as described above to the subject before the subject undergoes an organ transplant and/or immediately after the organ transplantation.

The present invention also refers to a method of treating a subject suffering from an inflammatory disease comprising administering an effective amount of sphingoid bases in particular sphingoid bases comprising:

So (d18:5) having the following Formula (3) with x=1 and y=2:

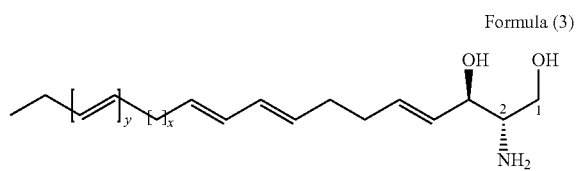

Formula (3)

So(d20:3) having Formula (3) as given above with x=7 and y=0,
So(d22:5) having Formula (3) as given above with x=5 and y=2,
So(t15:2) having Formula (4) with x=4 and y=0:

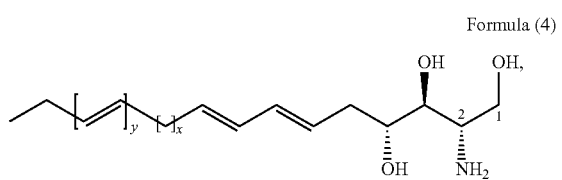

Formula (4)

So(t15:3) having Formula (4) as given above with x=2 and y=1,
So(t19:2) having Formula (4) as given above with x=8 and y=0,
So(t21:3) having Formula (4) as given above with x=8 and y=1,
So(t21:4) having Formula (4) as given above with x=6 and y=2,
So(m22:1) having Formula (5) with x=12, y=0 and z=0:

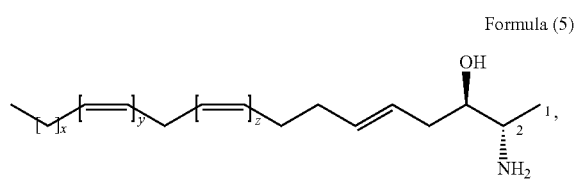

Formula (5)

So(m22:2) having Formula (5) as given above with x=10, y=0 and z=1, and
So(m22:3) having Formula (5) as given above with x=8, y=1 and z=1.

More preferably, the sphingoid bases administered comprise the sphingoid bases of table 2, i.e.:

| Sphingoid base | Formula |
|---|---|
| Sa (d14:0) | C14 H31 N O2 |
| So (d14:1) | C14 H29 N O2 |
| So (d14:2) | C14 H27 N O2 |
| So (d14:3) | C14 H25 N O2 |
| So (d15:1) | C15 H31 N O2 |
| So (d16:1) | C16 H33 N O2 |
| Sa (d17:0) | C17 H37 N O2 |
| Sa (d18:0) | C18 H39 N O2 |
| So (d18:1) | C18 H37 N O2 |
| So (d18:5) * | C18 H29 N O2 |
| So (d19:1) | C19 H39 N O2 |
| So (d19:2) | C19 H37 N O2 |
| So (d20:2) | C20 H39 N O2 |
| So (d20:3) | C20 H37 N O2 |
| So (d22:1) | C22 H45 N O2 |
| So (d22:1) isomer | C22 H45 N O2 |
| So (d22:2) | C22 H43 N O2 |
| So (d22:3) | C22 H41 N O2 |
| So (d22:5) | C22 H37 N O2 |
| So (t15:2) | C15 H29 N O3 |
| So (t15:3) | C15 H27 N O3 |
| Sa (t16:0) | C16 H35 N O3 |
| Sa (t18:0) | C18 H39 N O3 |
| So (t18:1) | C18 H37 N O3 |
| So (t18:2) | C18 H35 N O3 |
| So (t19:1) | C19 H39 N O3 |
| So (t19:2) | C19 H37 N O3 |
| So (t20:1) | C20 H41 N O3 |
| So (t21:3) | C21 H39 N O3 |
| So (t21:4) | C21 H37 N O3 |
| Sa (t22:0) | C22 H47 N O3 |
| So (t22:1) | C22 H45 N O3 |
| So (t22:2) | C22 H43 N O3 |
| So (t23:4) | C23 H41 N O3 |
| So (m14:3) | C14 H25 N O |
| Sa (m17:0) | C17 H37 N O |
| Sa (m18:0) | C18 H39 N O |
| So (m18:1) | C18 H37 N O |
| So (m22:1) | C22 H45 N O |
| So (m22:2) | C22 H43 N O |
| So (m22:3) | C22 H41 N O |
| So (m22:3) isomer | C22 H41 N O |
| Sphingofungin A | C21 H41 N3 O6 |

The sphingoid bases are administered as monotherapy or alternatively in combination with further pharmaceutically effective compounds for treating inflammatory diseases.

The subject is preferably a mammal and most preferably a human. The concentration of the sphingoid bases administered may be between 0.001 and 10 µM or up to 600 µg/mL, for example, up to 100 µg/mL like 1 µg/mL to 50 µg/mL.

The inflammatory disease can be selected from an autoimmune disease or an allergic disease.

Another aspect relates to a method of treating an inflammatory disease comprising:
isolating at least one sphingolipid portion from *Cordyceps* by the method described above, in particular a sphingoid base portion, a ceramide portion or a glycosphingolipid portion, further preferably a sphingoid base portion; and
formulating the sphingolipid portion into a pharmaceutically composition; and
administering said pharmaceutical composition to a subject suffering from an inflammatory disease. The subject is preferably a human.

The sphingolipid portion is most preferably a sphingoid base portion in particular comprising the sphingoid bases:

So (d18:5) having the following Formula (3) with x=1 and y=2:

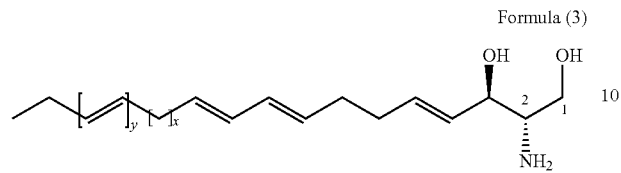

Formula (3)

So(d20:3) having Formula (3) as given above with x=7 and y=0,
So(d22:5) having Formula (3) as given above with x=5 and y=2,
So(t15:2) having Formula (4) with x=4 and y=0:

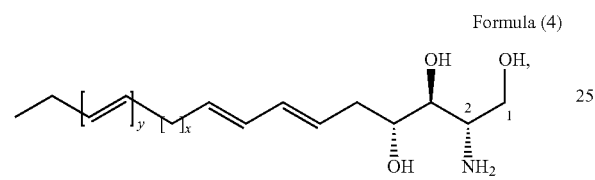

Formula (4)

So(t15:3) having Formula (4) as given above with x=2 and y=1,
So(t19:2) having Formula (4) as given above with x=8 and y=0,
So(t21:3) having Formula (4) as given above with x=8 and y=1,
So(t21:4) having Formula (4) as given above with x=6 and y=2,
So(m22:1) having Formula (5) with x=12, y=0 and z=0:

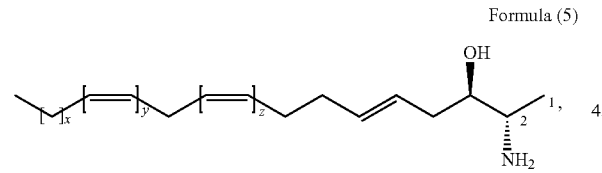

Formula (5)

So(m22:2) having Formula (5) as given above with x=10, y=0 and z=1, and
So(m22:3) having Formula (5) as given above with x=8, y=1 and z=1.
More preferably, the sphingoid base portion comprises the sphingoid bases of table 2, i.e.:

| Sphingoid base | Formula |
| --- | --- |
| Sa (d14:0) | C14 H31 N O2 |
| So (d14:1) | C14 H29 N O2 |
| So (d14:2) | C14 H27 N O2 |
| So (d14:3) | C14 H25 N O2 |
| So (d15:1) | C15 H31 N O2 |
| So (d16:1) | C16 H33 N O2 |
| Sa (d17:0) | C17 H37 N O2 |
| Sa (d18:0) | C18 H39 N O2 |
| So (d18:1) | C18 H37 N O2 |
| So (d18:5) * | C18 H29 N O2 |

-continued

| Sphingoid base | Formula |
| --- | --- |
| So (d19:1) | C19 H39 N O2 |
| So (d19:2) | C19 H37 N O2 |
| So (d20:2) | C20 H39 N O2 |
| So (d20:3) | C20 H37 N O2 |
| So (d22:1) | C22 H45 N O2 |
| So (d22:1) isomer | C22 H45 N O2 |
| So (d22:2) | C22 H43 N O2 |
| So (d22:3) | C22 H41 N O2 |
| So (d22:5) | C22 H37 N O2 |
| So (t15:2) | C15 H29 N O3 |
| So (t15:3) | C15 H27 N O3 |
| Sa (t16:0) | C16 H35 N O3 |
| Sa (t18:0) | C18 H39 N O3 |
| So (t18:1) | C18 H37 N O3 |
| So (t18:2) | C18 H35 N O3 |
| So (t19:1) | C19 H39 N O3 |
| So (t19:2) | C19 H37 N O3 |
| So (t20:1) | C20 H41 N O3 |
| So (t21:3) | C21 H39 N O3 |
| So (t21:4) | C21 H37 N O3 |
| Sa (t22:0) | C22 H47 N O3 |
| So (t22:1) | C22 H45 N O3 |
| So (t22:2) | C22 H43 N O3 |
| So (t23:4) | C23 H41 N O3 |
| So (m14:3) | C14 H25 N O |
| Sa (m17:0) | C17 H37 N O |
| Sa (m18:0) | C18 H39 N O |
| So (m18:1) | C18 H37 N O |
| So (m22:1) | C22 H45 N O |
| So (m22:2) | C22 H43 N O |
| So (m22:3) | C22 H41 N O |
| So (m22:3) isomer | C22 H41 N O |
| Sphingofungin A | C21 H41 N3 O6 |

The skilled person is able to select suitable pharmaceutically tolerable excipients for formulating the sphingolipid portion into a pharmaceutically composition depending on the form of the pharmaceutical composition and is aware of methods for manufacturing pharmaceutical compositions as well as able to select a suitable method for preparing the pharmaceutical composition depending on the kind of pharmaceutically tolerable excipients and the form of the pharmaceutical composition.

The pharmaceutical composition according to the invention can be present in solid, semisolid or liquid form to be administered by an oral, rectal, topical, parenteral or transdermal or inhalative route to a subject, preferably a human.

The pharmaceutical composition may comprise further pharmaceutical effective ingredients such as therapeutic compounds used for treating inflammatory diseases.

EXAMPLES

Materials and Animals

Methanol (MeOH, LC-MS grade), isopropanol (IPA, LC-MS grade), chloroform (CHCl₃, HPLC grade), acetone (HPLC grade), hexane (HPLC grade), ethyl acetate (EtOAc, HPLC grade) were purchased from Avantor Performance Materials, Lnc. (Center Valley, Pa., USA). Formic acid (LC-MS grade), acetic acid (LC-MS grade), ammonium acetate (purity ≥98%), potassium hydroxide (KOH, purity ≥85%) and dimethyl sulfoxide (DMSO, purity ≥99%) were purchased from Sigma-Aldrich (St. Louis, Mo., USA). Distilled water was prepared using a Milli-Q system (Millipore, Billerica, Mass.). Davisil® silica media (GRACE 710 NW, Particle size 10-14 μm) and Davisil® amino silica media (GRACE 633 NNH₂, Particle size 35-70 μm) were purchased from Grace (Columbia, Md., USA). Lipopolysaccharide (LPS) and concanavalin A (Con A) were purchased from Sigma (St. Louis, Mo., USA), 3-(4, 5-dimethylthiazol-2-yl)-2,5-diphenyltetrazolium bromide (MTT) was purchased from Amersco LLC. (Cochran Road Solon, Ohio, USA). RPMI 1640 was purchased from Gibco (Invitrogen, Carlsbad, N. Mex., USA). Fetal Bovine Serum (FBS) was purchased from Zhejiang Tian Hang Biological technology stock Co., Ltd. (Zhejiang, China). Sphingolipid standards including So (m18:1), Sa (m18:0), So (d18:1), Sa (t18:0), Cer (d18:1/16:0), Cer (d18:0/16:0), Cer (18:1/18:0), Cer (18:0/18:1), Cer (18:0/18:0), Cer (18:1/22:0), Cer (18:1/24:1), Cer (18:1/24:0), Cer (18:0/24:1), Cer (d18:0/24:0), Cer (d18:0/24:0(OH)), Cer (t18:0/24:0), Cer (t18:0/24:0(OH)), SM (d18:1/12:0), SM (d18:0/12:0), SM (d18:1/16:0), SM (d18:1/17:0), SM (d18:1/18:0) and SM (d18:1/24:0) were obtained from Avanti Polar Lipids (Alabaster, Ala., USA). So (d14:1), SM (d18:1/20:0), SM (d18:1/22:0) and Hex-Hex-Hex-Cer (18:1/24:0) were obtained from Matreya LLC (Pleasant Gap, Pa., USA). FTY720 (purity >98%) was purchased from Santa Cruz Biotechnology, Inc. (Finnell Street Dallas, Tex., USA). Eight standards including Sa (d14:0), Cer (d18:0/22:0), SM (d18:0/16:0), SM (d18:0/17:0), SM (18:0/18:0), SM (d18:0/20:0), SM (d18:0/22:0) and SM (d18:0/24:0) were synthesized by reduction of the backbone double bond using hydrogen gas and 10% Pd on charcoal (Aldrich-Sigma, St. Louis, Mo.) (Fig. S9) and the conversion was verified by UHPLC-iFunnel-Q-TOF-MS/MS.

Male ICR mice (Weight, 10 to 22 g) were provided by the Comparative Medicine Center of Yangzhou University. The animal studies were approved by the Animal Ethics Committee of China Pharmaceutical University. The animals were cared for according to the regulations of the Animal Committee.

Example 1A

Isolation of Sphingolipid Portions from *Cordyceps*

The sphingolipid (SPL) crude extract was prepared by weighting 65 g of powdered wild-type *Cordyceps* into a glass bottle, in which 1 L of the first extracting solvent [CHCl$_3$/MeOH (1:2, v/v)] was added. The mixture was incubated at 48° C. for 12 h. After pressure filtration, the filtrate was collected and the residue was ultrasound-assisted extracted with 1 L of the first extracting solvent for 30 min. After pressure filtration, the filtrate was collected and the residue was ultrasound-assisted extracted two times with 1 L of the second extracting solvent [CHCl$_3$/MeOH (2:1, v/v)] for 30 min each time. After pressure filtration, all filtrates were combined and concentrated to 400 mL by using a rotary evaporator. Then, 40 mL of KOH in methanol (1 M) was added and the mixture was incubated at 37° C. with shaking for 2 h. The resultant extract was then neutralized with 0.7 mL acetic acid and centrifuged. The supernatant was evaporated to the SPL crude extract at 40° C. The resulting SPL crude extract was fractionated by silica gel column chromatography (4.2 cm I.D.×29 cm) with 5 bed volume (BV) CHCl$_3$, 3.5 BV acetone/methanol (9:1, v:v) and finally with 7.5 BV methanol to give three SPL enriched fractions. Then, these SPL enriched fractions were further purified respectively to give a sphingoid base portion (49.6 mg), a ceramide portion (68.1 mg), a glycosphingolipid portion (299.1 mg) and a phosphosphingolipid, namely a sphingomyelin portion (35.1 mg) by NH$_2$ silica gel column chromatography (4.2 cm I.D.×25 cm) with 2 BV hexane, 6 BV hexane/ethyl acetate (85:15, v:v), 5 BV CHCl$_3$/methanol (23:1, v:v), 5 BV acetone/methanol (9:1.35, v:v) and 5 BV CHCl$_3$/methanol (2:1, v:v).

Example 2

Identification of the Sphingolipids in the Sphingolipid Portions

Figure 1B:
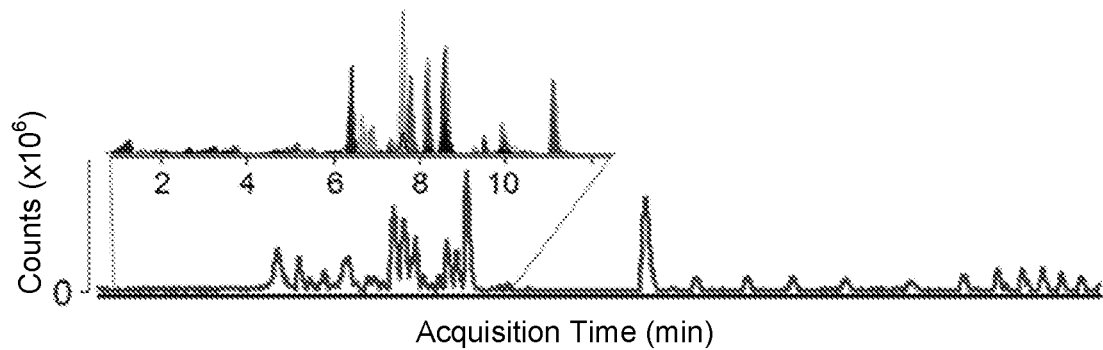
FIG. 1B shows a base peak chromatogram of the sphingoid base portion of the wild-type *Cordyceps* material obtained with UHPLC-UHD iFunnel-Q-TOF MS after chromatographic separation.
Figure 1C:
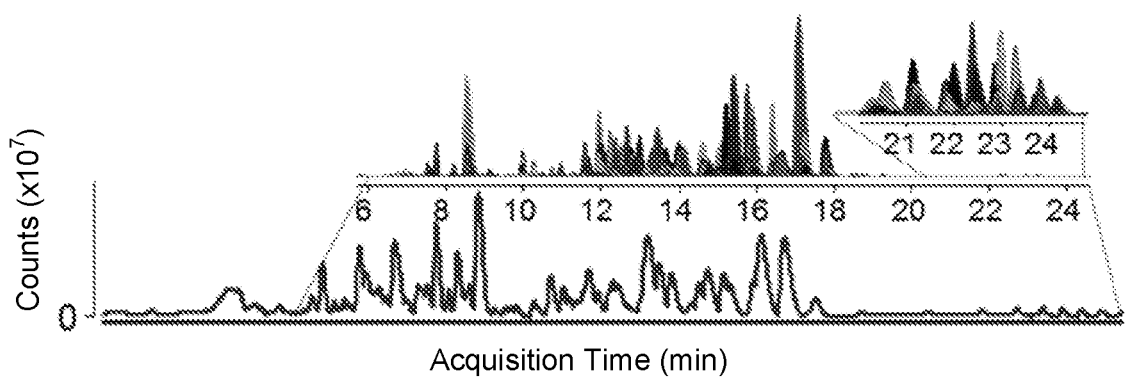
FIG. 1C shows a base peak chromatogram of the ceramide portion of the wild-type *Cordyceps* material obtained with UHPLC-UHD iFunnel-Q-TOF MS after chromatographic separation.
Figure 1D:
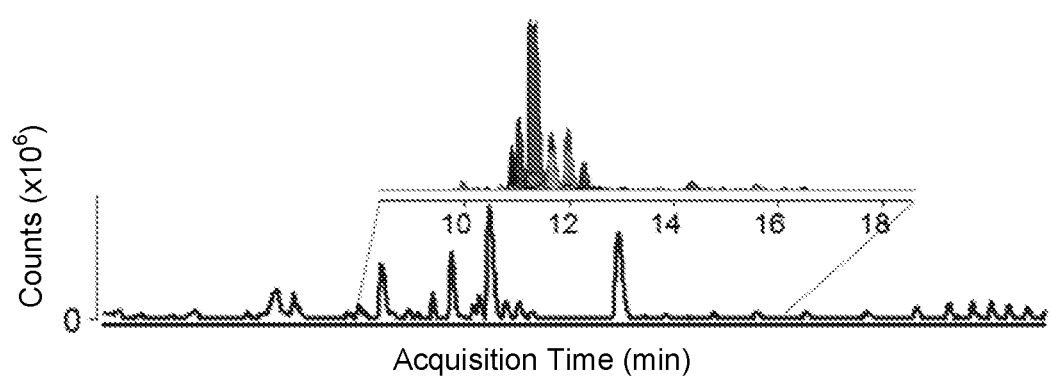
FIG. 1D shows a base peak chromatogram of the glycosphingolipid portion of the wild-type *Cordyceps* material obtained with UHPLC-UHD iFunnel-Q-TOF MS after chromatographic separation.
Figure 1E:
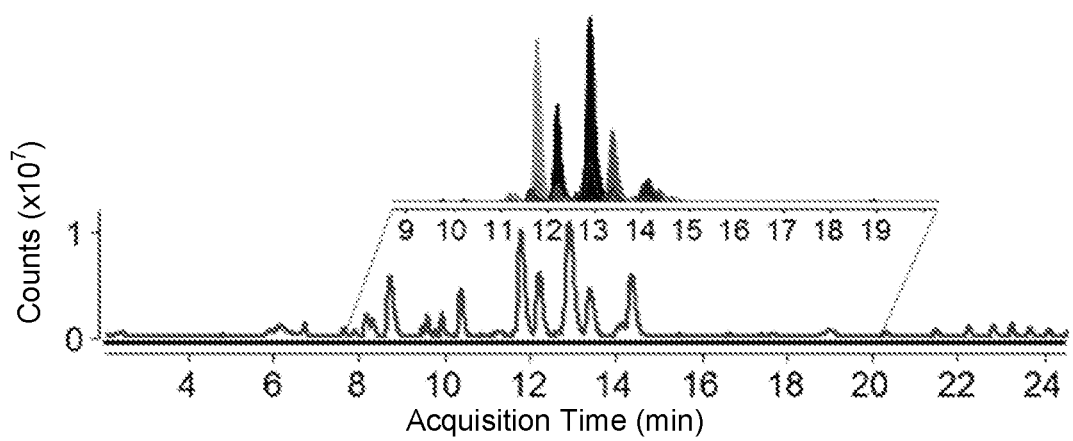
FIG. 1E shows a base peak chromatogram of the sphingomyelin portion of the wild-type *Cordyceps* material obtained with UHPLC-UHD iFunnel-Q-TOF MS after chromatographic separation.

For detection of SPLs, an optimized UHPLC-ultrahigh definition (UHD) iFunnel-Q-TOF MS approach as described in Wang J. R. et al., Anal. Chem. 2014, 86, 5688 and Mi J. N. et al., Sci. Rep. 2016, 6, 20870. doi: 10.1038/srep20870 was used. For chromatographic separation, an Agilent 1290 Infinity UHPLC system (Santa Clara, Calif., USA) was used equipped with a binary solvent delivery system, a standard autosampler, and an Agilent Eclipse Plus C18 column (100× 2.1 mm, 1.8 µm). methanol/H$_2$O/formic acid (60:40:0.2, v/v/v) (A) and methanol/isopropyl alcohol/formic acid (60:40:0.2, v/v/v) (B), both of which contained 10 mM ammonium acetate were used as eluents at a flow rate was 0.35 mL/min. MS and MS/MS analysis were carried out on an Agilent UHD 6550 iFunnel-Q-TOF mass spectrometer (Santa Clara, Calif., USA) with a Jet Stream electrospray ionization source in the positive ion mode. Mass spectra were recorded across the range of m/z 200-1700; MS/MS spectra were recorded across the range of m/z 40-1700. Targeted MS/MS collision energies were from 10 to 60 eV. Base peak chromatograms are shown in FIG. 1A (blank sample), FIG. 1B (sphingoid base portion), FIG. 1C (ceramide portion), FIG. 1D (glycosphingolipid portion) and FIG. 1E (sphingomyelin portion).

Example 2A

Elimination of Ion-Source Cleavage Interferences

Figure 2:
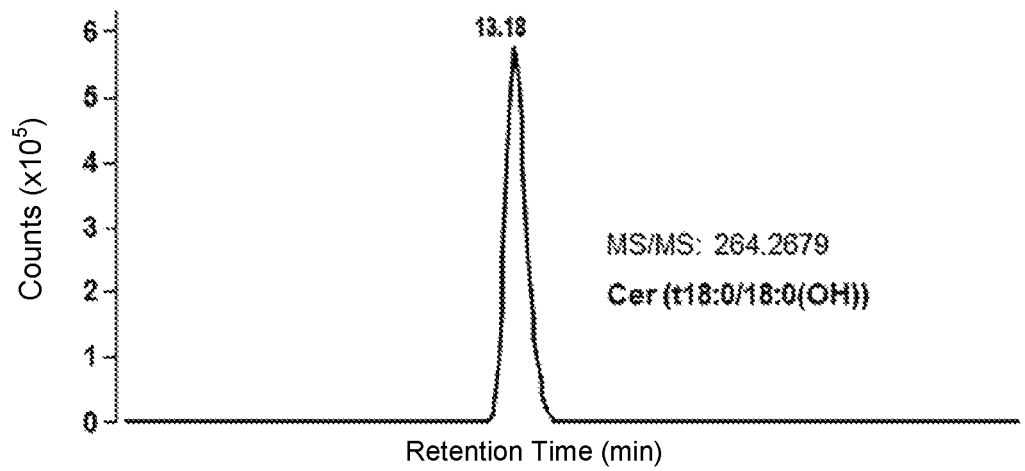
FIG. 2 shows an extracted compound chromatogram (ECC) of a compound of formula $C_{36}H_{73}NO_5$ in 10 ppm of masses tolerance.
Figure 3:
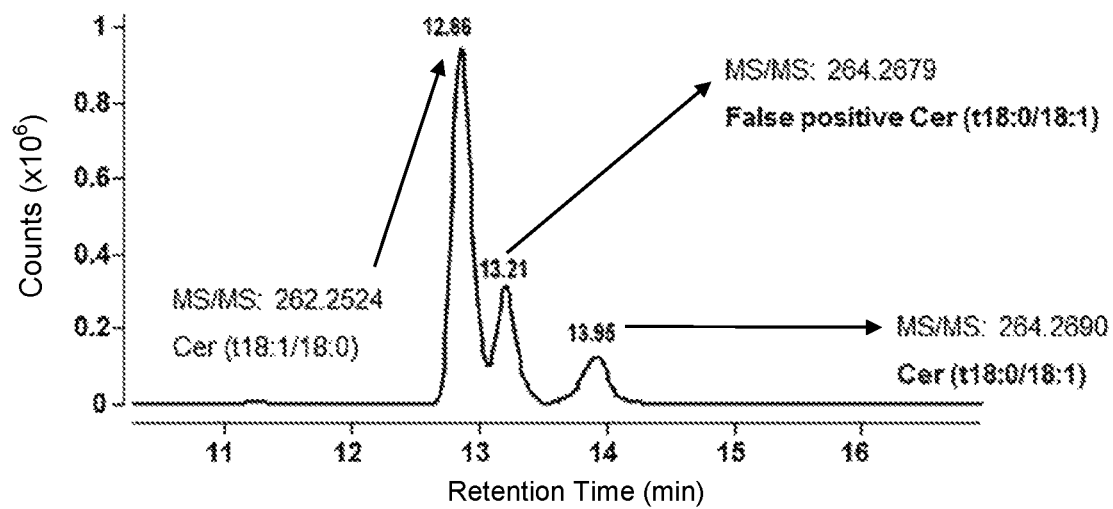
FIG. 3 shows an extracted compound chromatogram (ECC) of a compound of formula $C_{36}H_{71}NO_4$ in 10 ppm of masses tolerance.

Polyhydroxyl SPLs are prone to fragment into dehydration products partially during ionization in source, and these dehydration products always are identified as false positive SPLs. As shown in FIG. 2, a chromatographic peak is detected in the extract compound chromatography (ECC) of the formula with $C_{36}H_{73}NO_5$. From the MS spectrum, the accurate mass of [M+H]$^+$ (m/z 600.5568) and [M−H$_2$O+H]$^+$ (m/z 582.5454) are obtained, which indicate that the compound has been fragmented into dehydration products partially during ionization in source. From the targeted MS/MS spectrum, the characterized fragment of m/z 264 indicates that the compound is Cer (t18:0/18:0(OH)). Three chromatographic peaks are detected in the ECC of the formula with $C_{36}H_{71}NO_4$ under optimized chromatographic separation condition (FIG. 3). From the MS spectrum, the accurate mass of [M+H]$^+$ (m/z 582.5462), [M+H]$^+$ (m/z 582.5462), [M+H]$^+$ (m/z 582.5456) are obtained from compounds of retention time (RT) 12.86 min, RT 13.21 min and RT 13.95 min, respectively. Based on the targeted MS/MS spectrum, the compound of RT 12.86 min is arranged as Cer (t18:1/18:0) (fragment of m/z 262), two compounds of RT 13.21 min and RT 13.95 min both are arranged as Cer (t18:0/18:1) (fragment of m/z 264). But by comparison of the accurate mass and RT of the compound of RT 13.21 min and Cer (t18:0/18:0(OH)), the former is arranged as the dehydration product of Cer (t18:0/18:0(OH)).

Example 2B

Proposed LC-MS Fragmentation Pathways of Sphingolipids

The feature ions representative of sphingoid backbone, fatty acid chain and headgroup summarized from the fragmentation pathways of SPLs are applied in the identification of SPLs. The neutral loss information indicated in the fragmentation pathways of SPLs permit the identification of SPLs class and sphingoid backbone subclass. In positive ion mode, SPLs yield abundant protonated molecular species ([M+H]$^+$) by electrospray ionization.

Figure 4A:
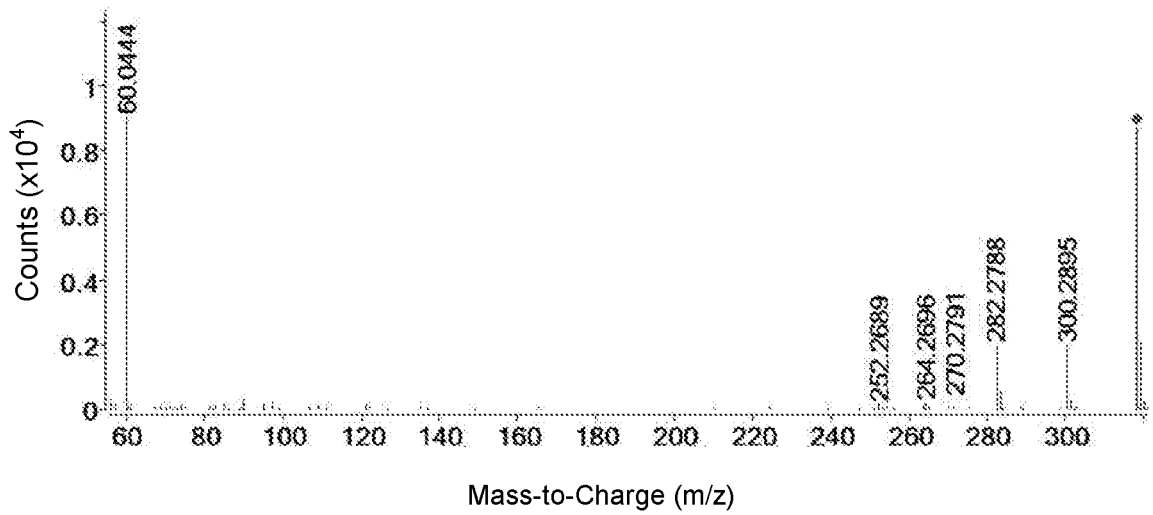
FIG. 4A shows the MS/MS spectra of protonated Sa (t18:0).
Figure 4B:
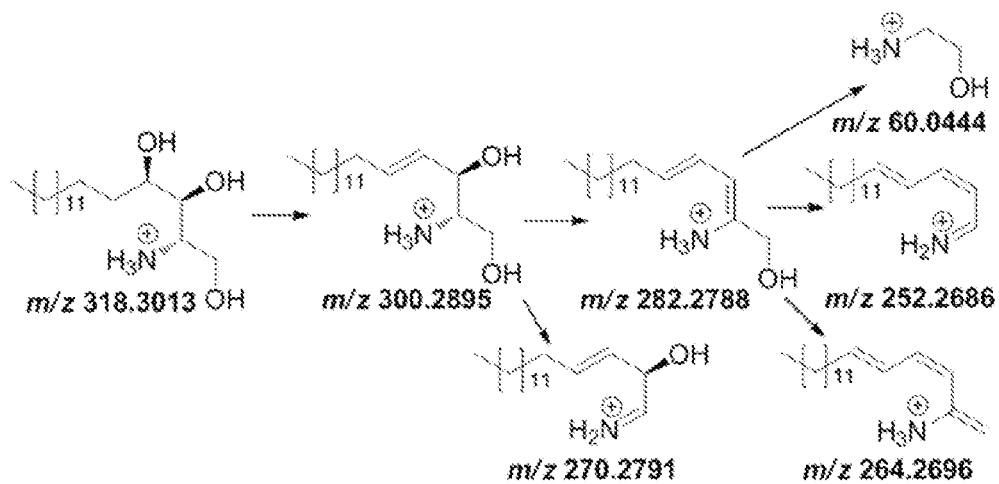
FIG. 4B shows the proposed fragmentation pathways of protonated Sa (t18:0) for ion formation.

For the identification of sphingoid bases, in the MS/MS spectrum (FIGS. 4A and 4B) the [M+H]$^+$ ion of Sa (t18:0) at m/z 318 yields three feature ions at m/z 300, m/z 282 and m/z 264 by loss of H$_2$O, which reveal that there are three hydroxyl groups in Sa (t18:0). The precursor ion and the product ion by loss of a H$_2$O are used in identification of sphingoid bases.

Figure 5A:
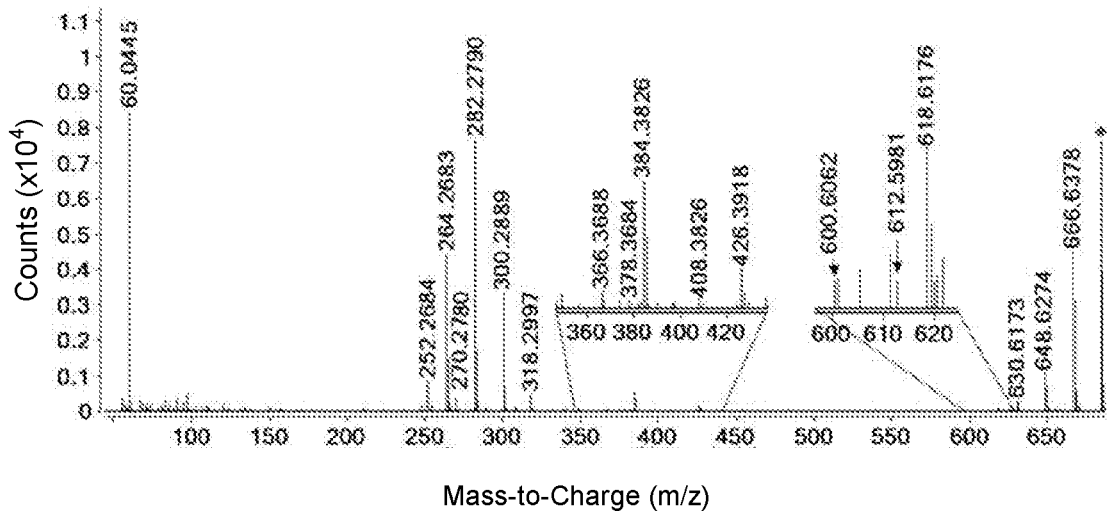
FIG. 5A shows the MS/MS spectra of protonated Cer (t18:0/24:0(2OH)).
Figure 5B:
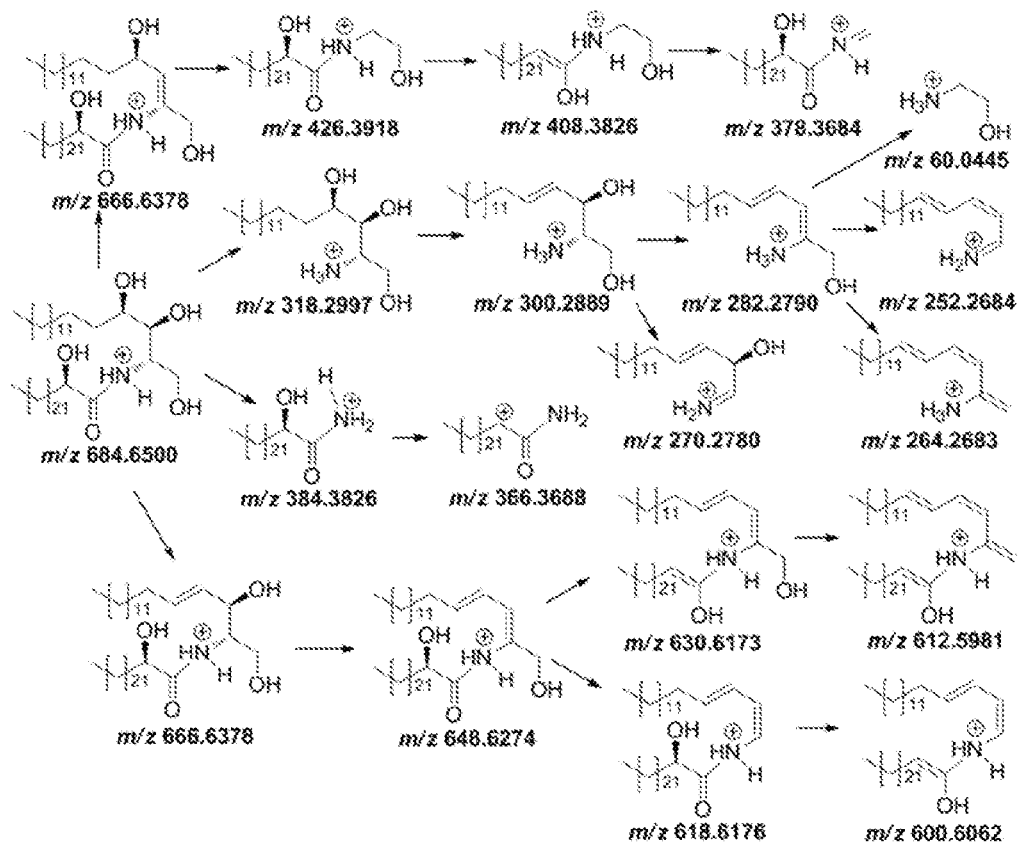
FIG. 5B shows the proposed fragmentation pathways of protonated Cer (t18:0/24:0(2OH)) for ion formation.

For the identification of ceramides, in the MS/MS spectrum (FIGS. 5A and 5B) the [M+H]$^+$ ion of Cer (t18:0/24:0(2OH)) at m/z 684 undergoes vigorous fragmentation when subjected to collision-induced dissociation (CID). The ions at m/z 666, m/z 648, m/z 630 and m/z 612 are yielded by loss of different quantity of H$_2$O. However, the m/z 618 ion and m/z 600 ion are yielded by further loss of HCHO from ions at m/z 648 and m/z 630, respectively. This information indicates that there are four hydroxyl groups in Cer (t18:0/24:0(2OH)). The cleavage of the C2-C3 bond of the sphingoid backbone results in an ion at m/z 426, which leads to an ion at m/z 408 by loss of H$_2$O. The ion at m/z 378 is yielded by further loss of HCHO from m/z 408 ion. The direct cleavage of the C2-N bond gives rise to the m/z 384 ion, along with m/z 366 which is yielded by loss of H$_2$O from m/z 384 ion, indicating that there is a hydroxyl group in fatty acid chain of ceramide. The elimination of the fatty acid chain as a ketene from the m/z 684 ion results in a low-abundance ion of m/z 318, which is a protonated phytosphingosine and the precursor ion leading to the m/z 300 ion by a H$_2$O loss. The m/z 300 ion yields the ion species of m/z 282 and 270 via further loss of H$_2$O and HCHO, respectively. The ions of m/z 264 and 252 arise from m/z 282 by loss of H$_2$O and HCHO, respectively. Since the ions at m/z 264 and 366 respectively reflect the sphingoid backbone and fatty acid chain of ceramides, the structure of ceramides can be easily identified.

Figure 6A:
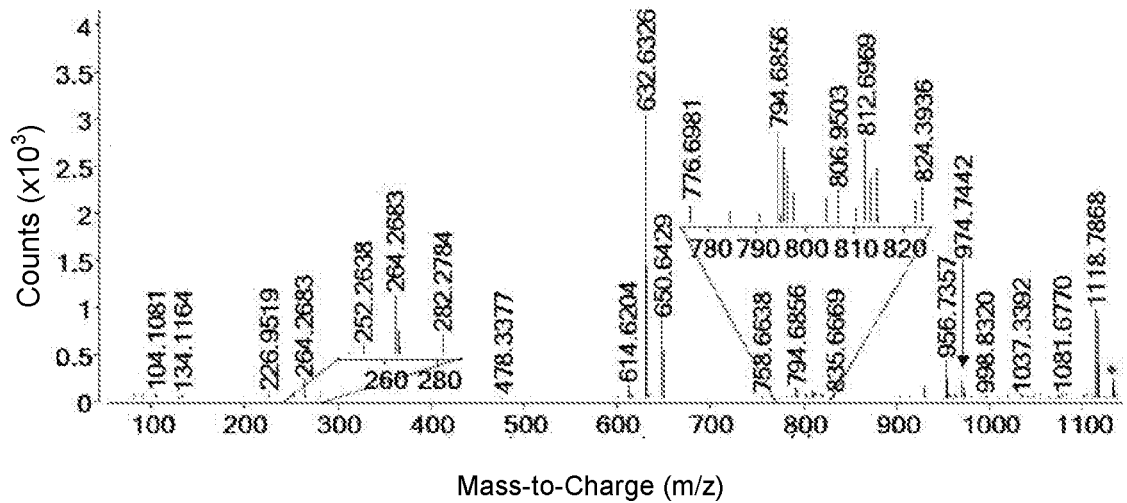
FIG. 6A shows the MS/MS spectra of protonated Hex-Hex-Hex-Cer (d18:1/24:0).
Figure 6B:
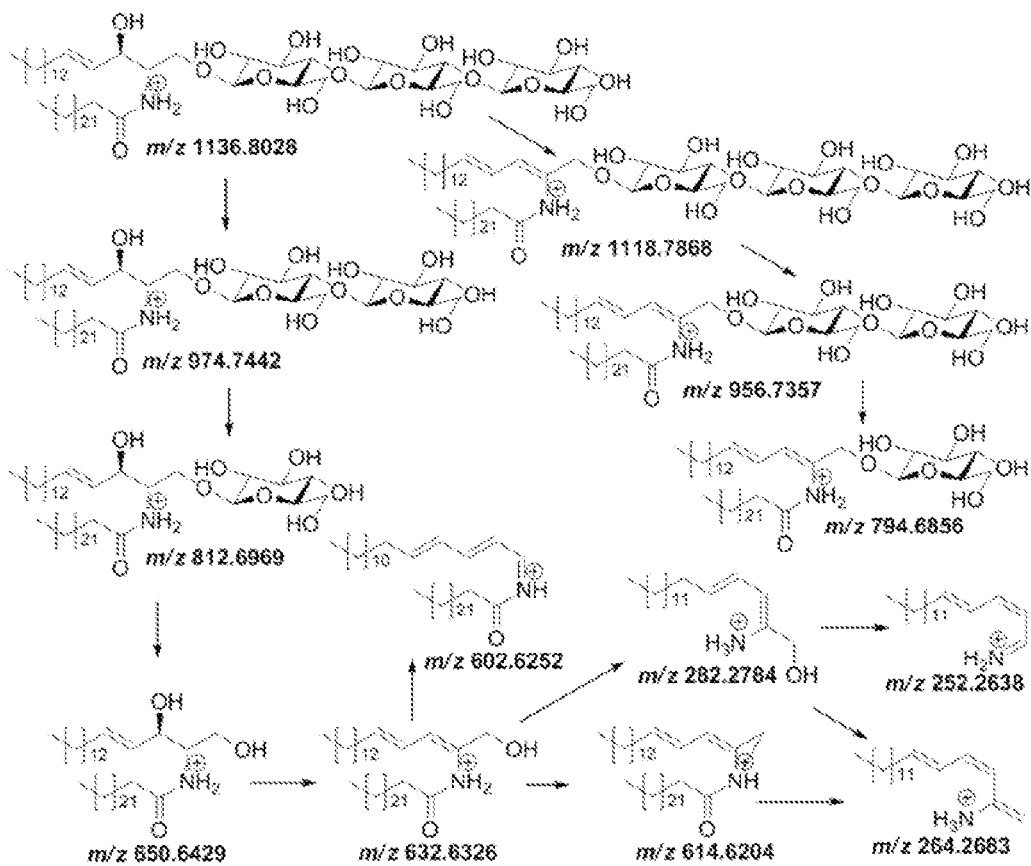
FIG. 6B shows the proposed fragmentation pathways of protonated Hex-Hex-Hex-Cer (d18:1/24:0) for ion formation.

For the identification of glycosphingolipids, as illustrated in FIGS. 6A and 6B the product-ion spectrum of the protonated Hex-Hex-Hex-Cer (d18:1/24:0) at m/z 1136 contains ceramide moiety ions at m/z 650 ([M−Hex-Hex-Hex+H]$^+$), m/z 632 ([M−Hex-Hex-Hex-H$_2$O+H]$^+$), m/z 614 ([M−Hex-Hex-Hex-2H$_2$O+H]$^+$) and m/z 602 ([M−Hex-Hex-Hex-H$_2$O—HCHO+H]$^+$); and sphingoid backbone ions at m/z 282, m/z 264 and m/z 252. However, ions that are characteristic to glycosphingolipids arise from the cleavages of glycan chain. The ion at m/z 1136 yields the ion at m/z 1118 by loss of H$_2$O, which leads to an ion at m/z 956 by loss of an hexosyl group followed by the ion at m/z 794 arises from m/z 956 ion by further loss of hexosyl group. The direct elimination of the hexosyl groups from the precursor yields a weak peak of m/z 974 ion. This is followed by further loss of second hexosyl group to give rise to ion at m/z 812. The observation of the ions is consistent with loss of glycan group from precursor ion, which is diagnostic to the glycan chain of glycosphingolipids.

Figure 7A:
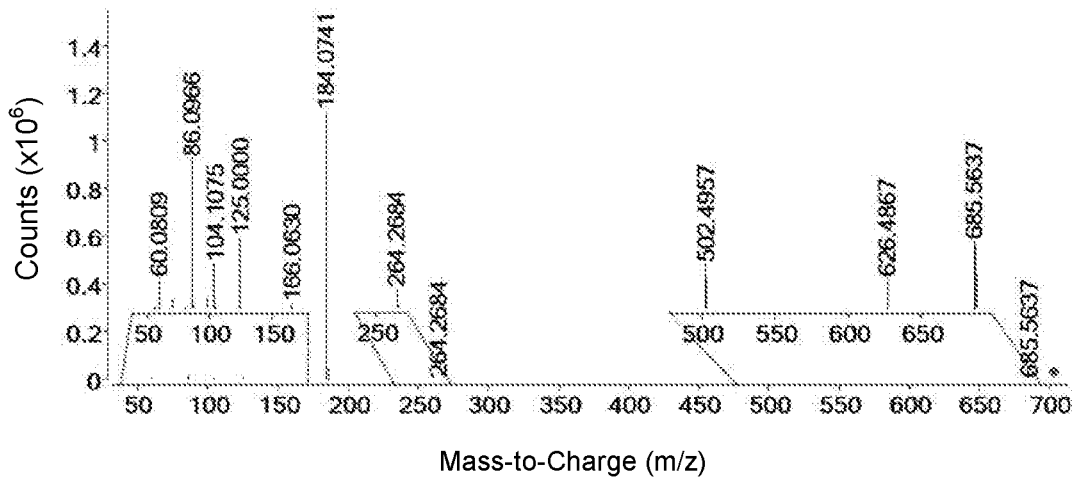
FIG. 7A shows the MS/MS spectra of protonated SM (d18:1/16:0).
Figure 7B:
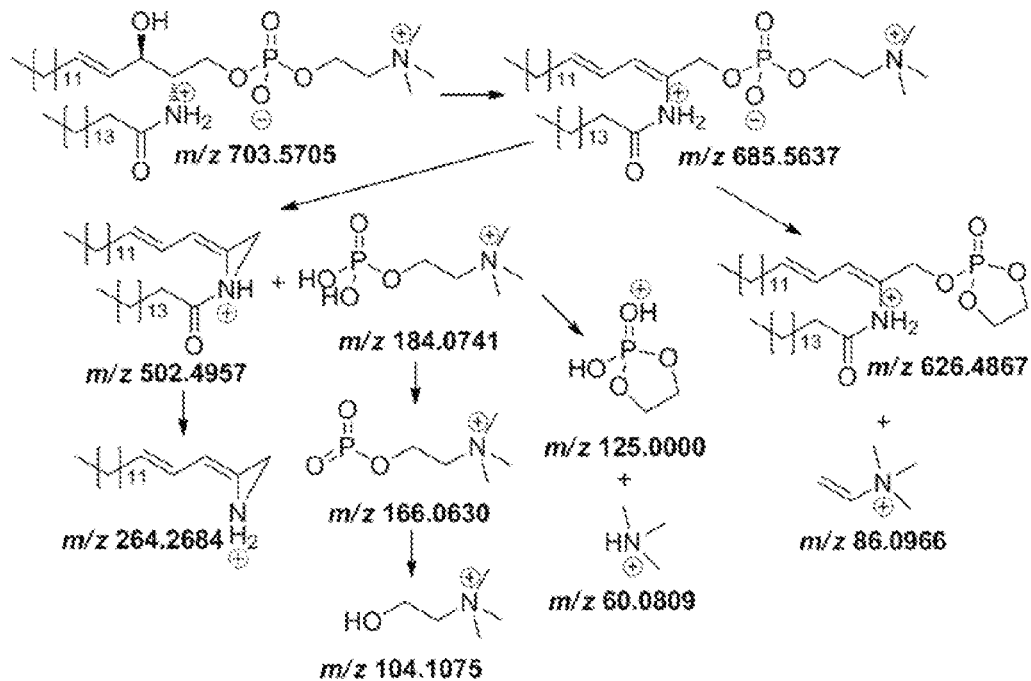
FIG. 7B shows the proposed fragmentation pathways of protonated SM (d18:1/16:0) for ion formation.

For identification of sphingomyelins, the MS/MS spectra of the [M+H]$^+$ ion arising from sphingomyelins yield one major fragment ion at m/z 184, corresponding to protonated phosphocholine. Ions reflecting the fatty acid constituents are not observed (FIGS. 7A and 7B). Because a weak peak of m/z 264 ion reflects the sphingoid backbone in sphingomyelin molecule, the structure of sphingomyelins can be easily determined.

Example 2C

Applications of the Retention Time During Identification of Sphingolipids

Figure 8:
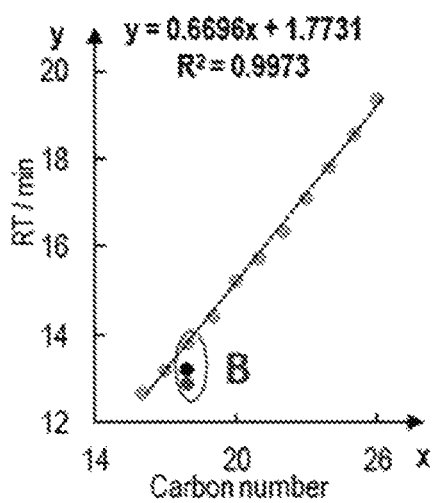
FIG. 8 is a linear regression model showing the relationship between the carbon number and the retention time for Cer (t18:0/x:1), in which the portion related to Cer (t18:0/18:1) is circled and denoted with "B".
Figure 9A:
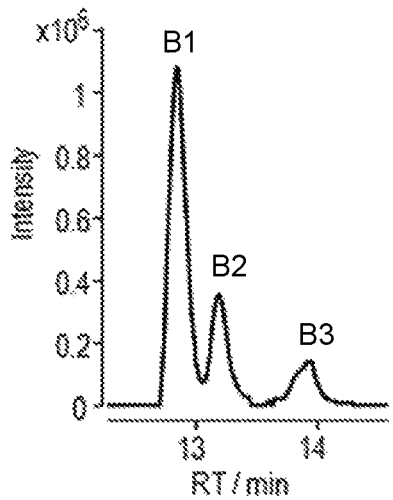
FIG. 9A shows a chromatogram of Cer (t18:0/18:1) having the formula $C_{36}H_{71}NO_4$ and three chromatographic peaks which are denoted with B1, B2 and B3 respectively.
Figure 9B:
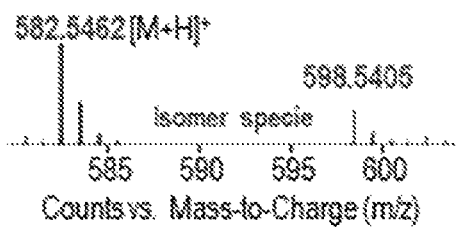
FIG. 9B shows the MS/MS spectrum relating to the peak B1 as shown in FIG. 9A.
Figure 9C:
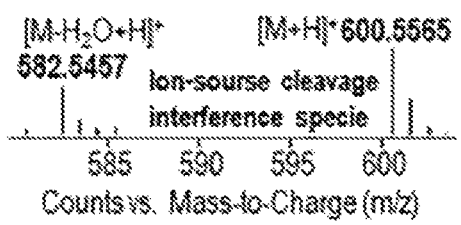
FIG. 9C shows the MS/MS spectrum relating to the peak B2 as shown in FIG. 9A.
Figure 9D:
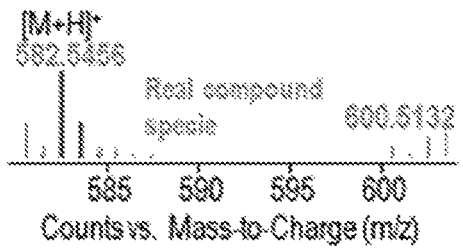
FIG. 9D shows the MS/MS spectrum relating to the peak B3 as shown in FIG. 9A.
Figure 10:
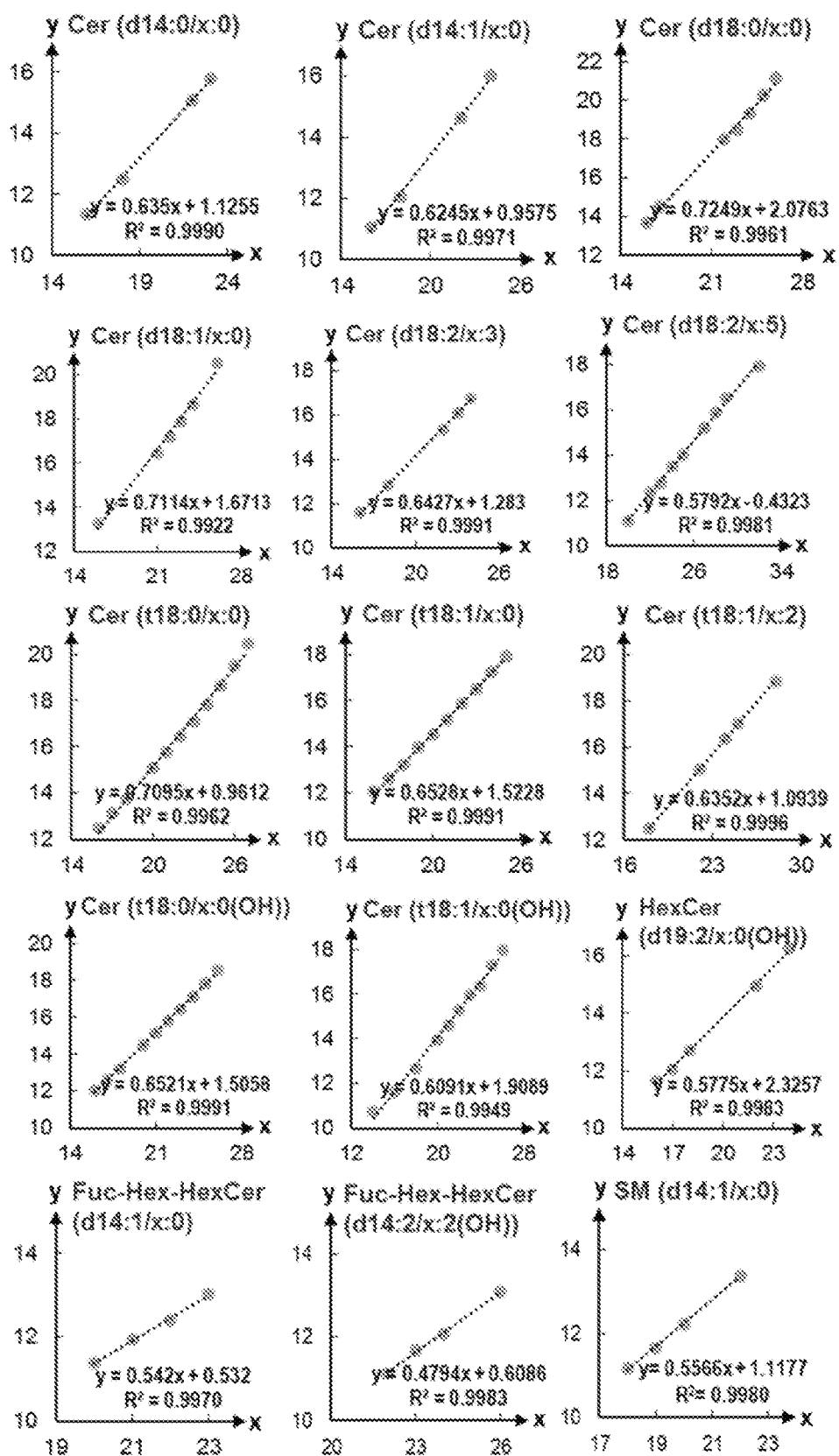
FIG. 10 shows the linear relationship between the number of carbon atoms and the retention time on C18 column of various sphingolipids, while the x-axis represents the number of carbon atoms of sphingolipids and the y-axis represents the retention time (min).

Based on the identification of SPLs, a linear regression model is constructed by plotting carbon number v.s. RT of species sharing the same sphingoid backbone and unsaturated degree (Fig. S7-S8), Goodness of fit ($r^2$>0.997) implied its capability for prediction of chromatographic retention of some species given its chain composition, as well as for aiding in identification. When it appears that one SPL has more than one RT, it means that RT of this SPL may not be suitable for the linear regression model (see FIG. 8). However, the results are helpful for re-identification of compounds. As shown in FIG. 9A to 9D, compounds are identified as ion-source cleavage interference species of Cer (t18:0/18:0(OH)) and Cer (t18:1/18:0) which are the isomer species of Cer (t18:0/18:1), respectively. The relationships between the structure and the RT on C18 chromatography column of SPLs are presented in FIG. 10.

Example 2D

Confirmation of Sphingolipids by Using Commercial and Synthetic Standards

Figure 11:
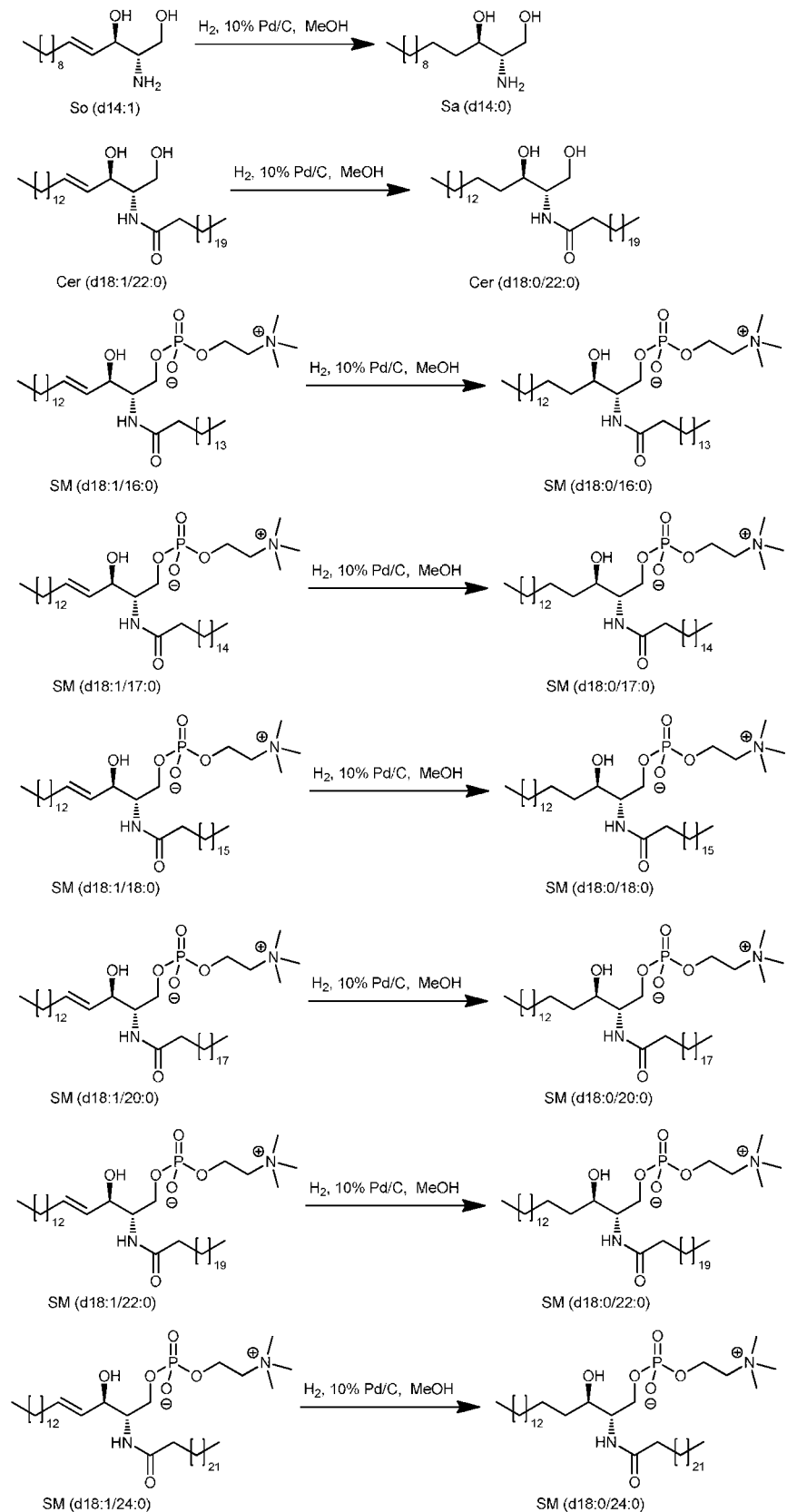
FIG. 11 shows the synthetic preparation of 8 sphingolipids. Hydrogenation ($H_2$, 10% Pd/C, methanol) of the unsaturated sphingolipid standards afforded saturated sphingolipids that were identified by UHPLC-UHD iFunnel Q-TOF MS.
Figure 12:
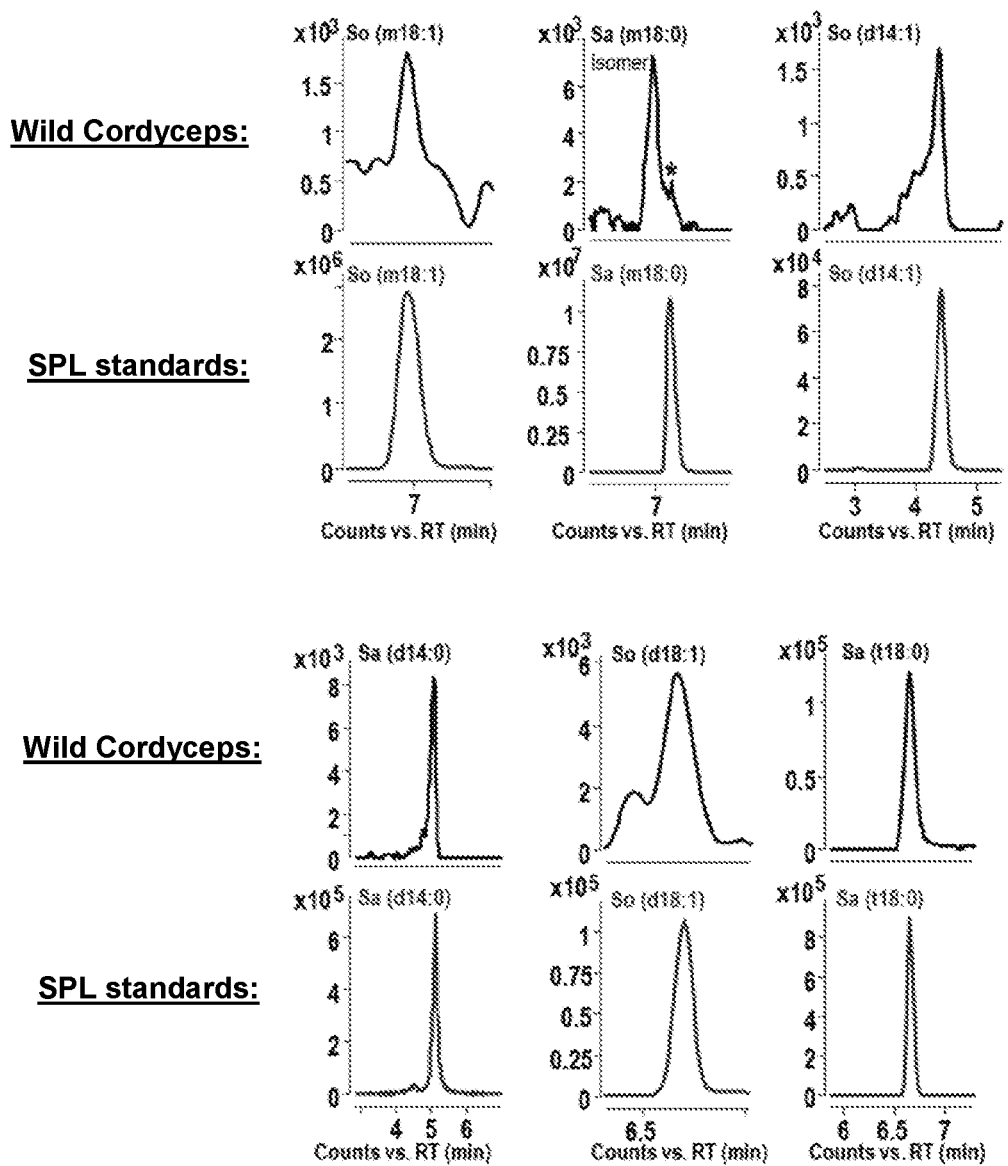
FIG. 12 shows MS/MS spectra of sphingoid bases isolated from wild-type *Cordyceps* material and the corresponding sphingolipid standards, wherein the sphingoid bases isolated from wild-type *Cordyceps* material include So (m18:1), Sa (m18:0), So (d14:1), Sa (d14:0), So (d18:1) and Sa (t18:0).
Figure 13A:
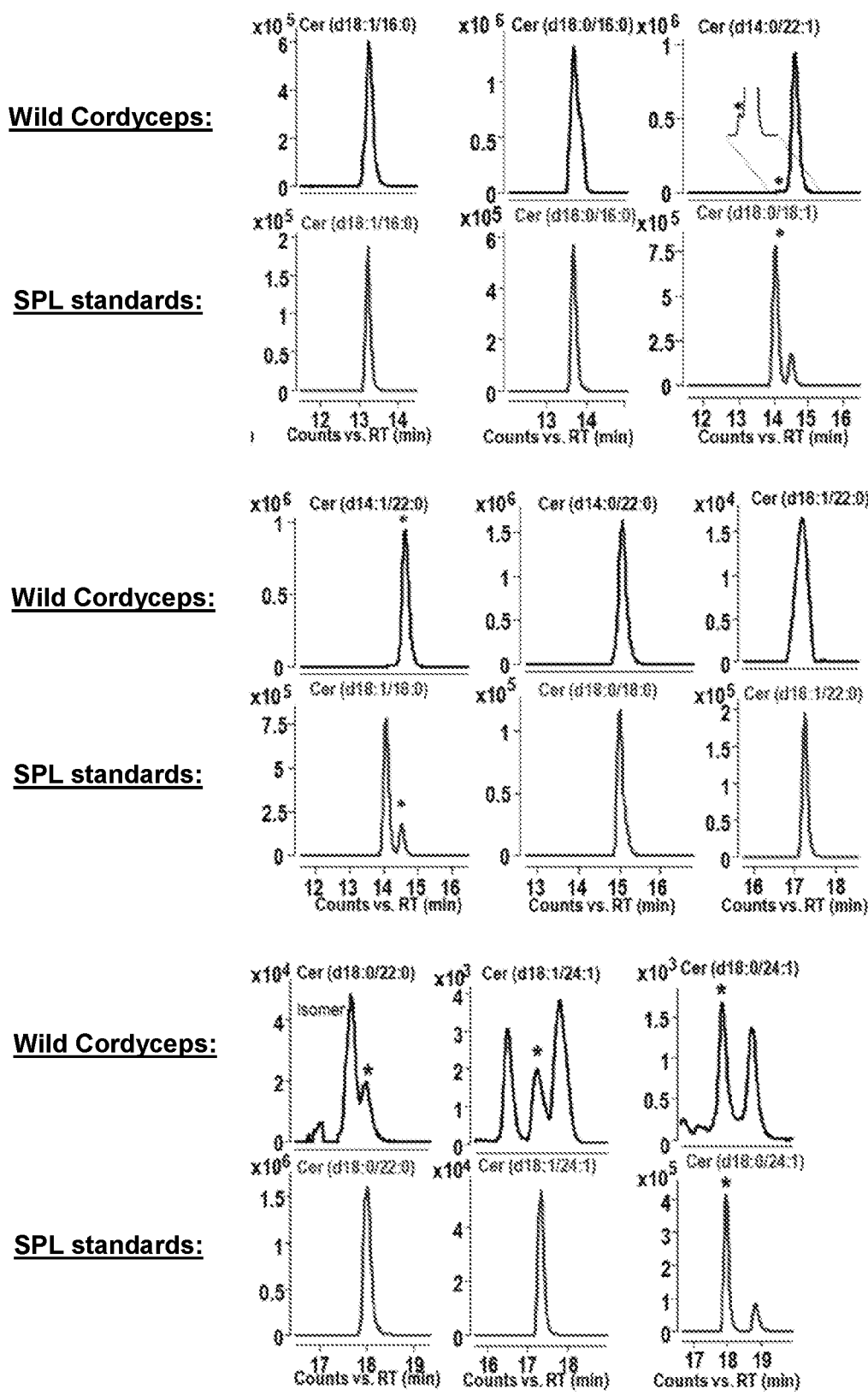
Figure 13B:
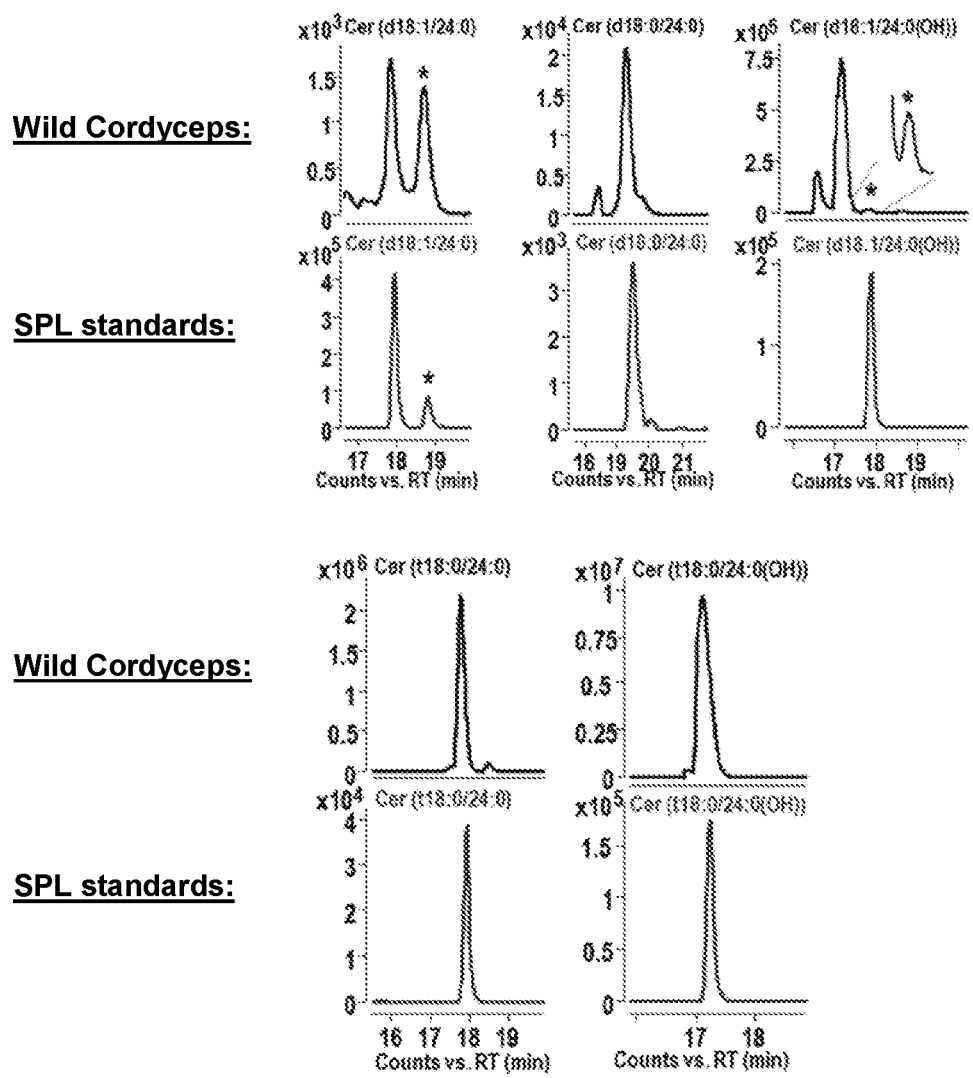
Figure 14A:
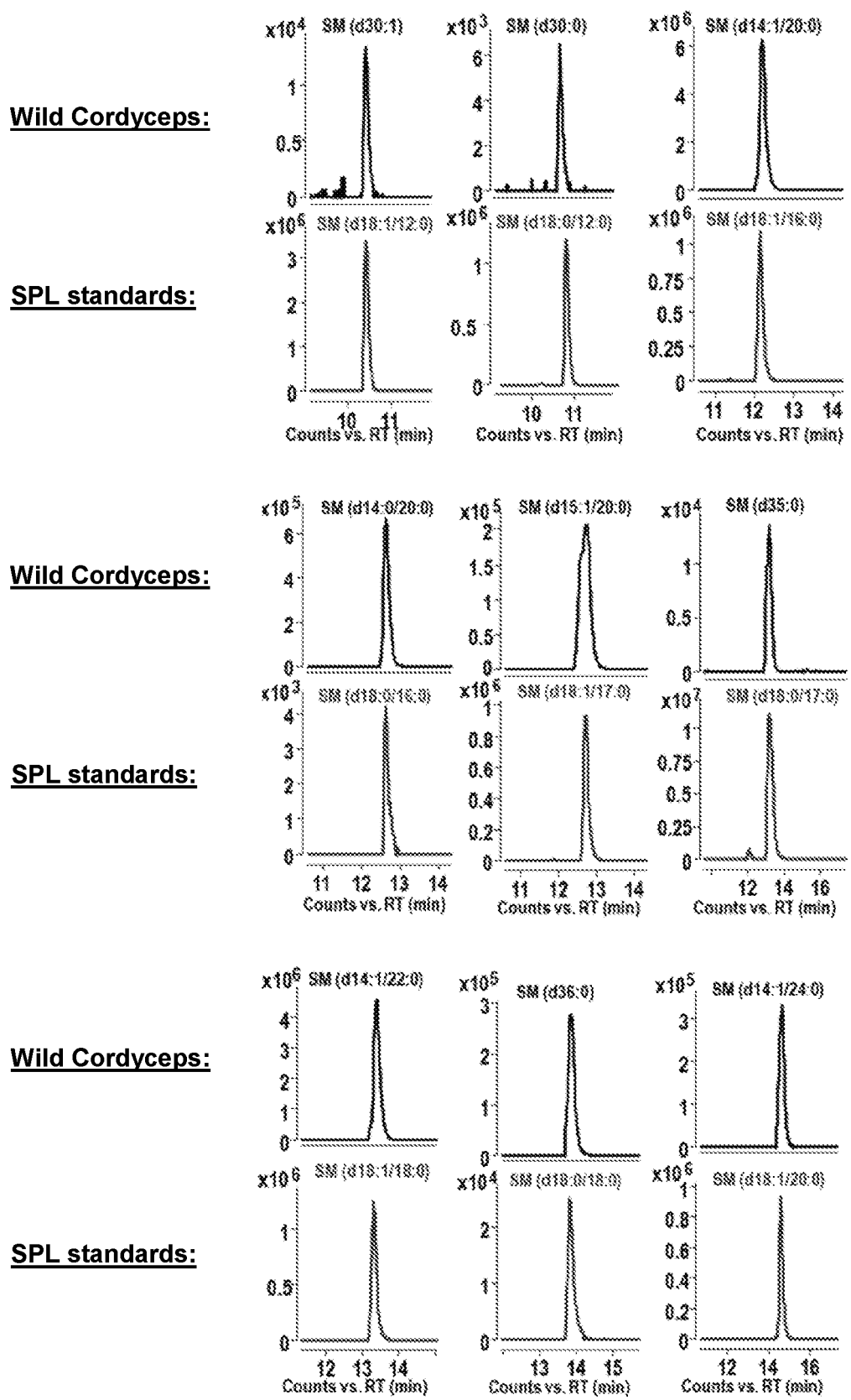
Figure 14B:
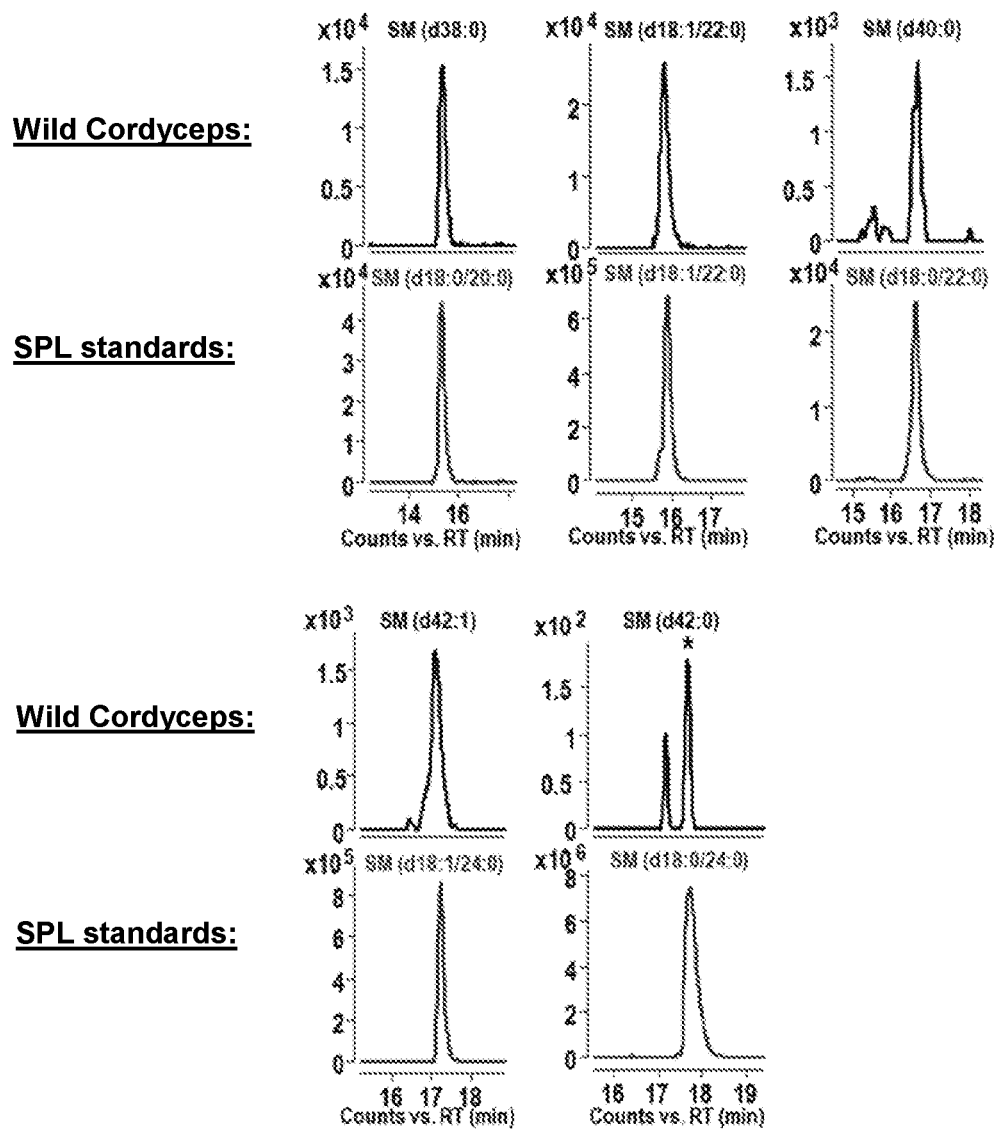
Figure 15A:
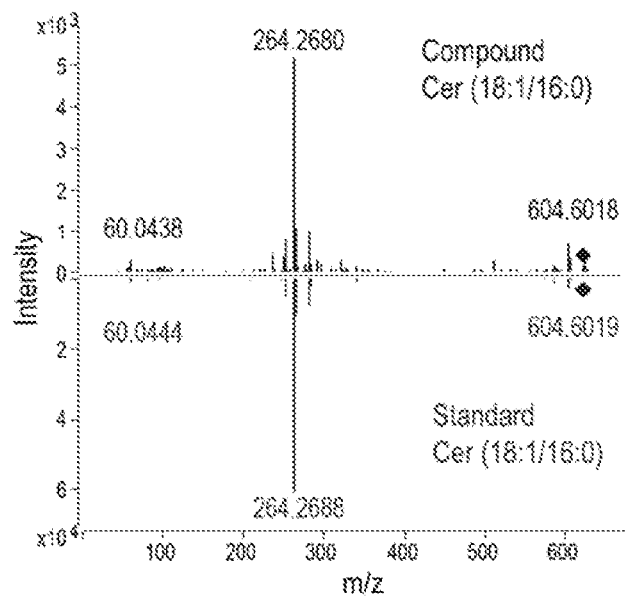
FIG. 15A shows the comparison of the MS/MS spectra of Cer (18:1/16:0) isolated from wild-type *Cordyceps* material and of the corresponding sphingolipid standard.
Figure 15B:
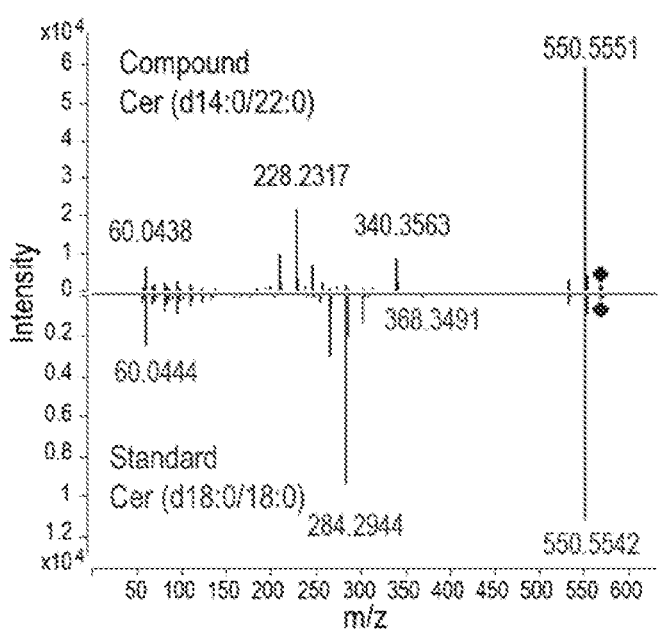
FIG. 15B shows the comparison of the MS/MS spectra of Cer (d14:0/22:0) isolated from wild-type *Cordyceps* material and of the corresponding sphingolipid standard.
Figure 15C:
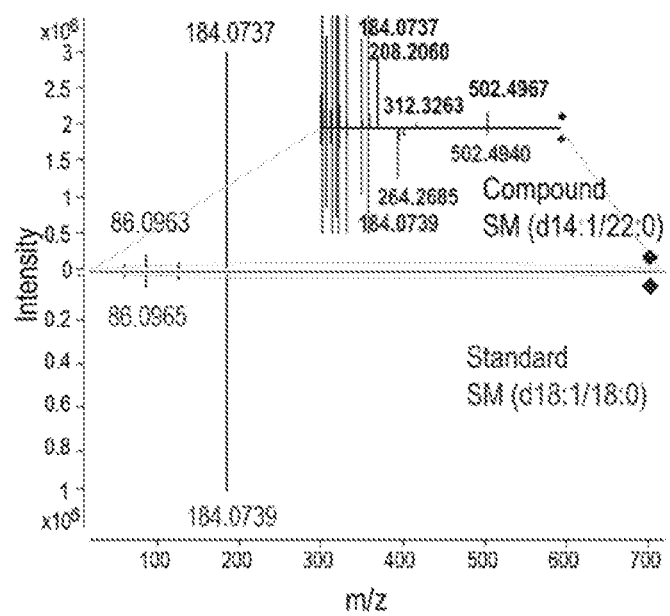
FIG. 15C shows the comparison of the MS/MS spectra of SM (d14:1/22:0) isolated from wild-type *Cordyceps* material and of the corresponding sphingolipid standard.
Figure 15D:
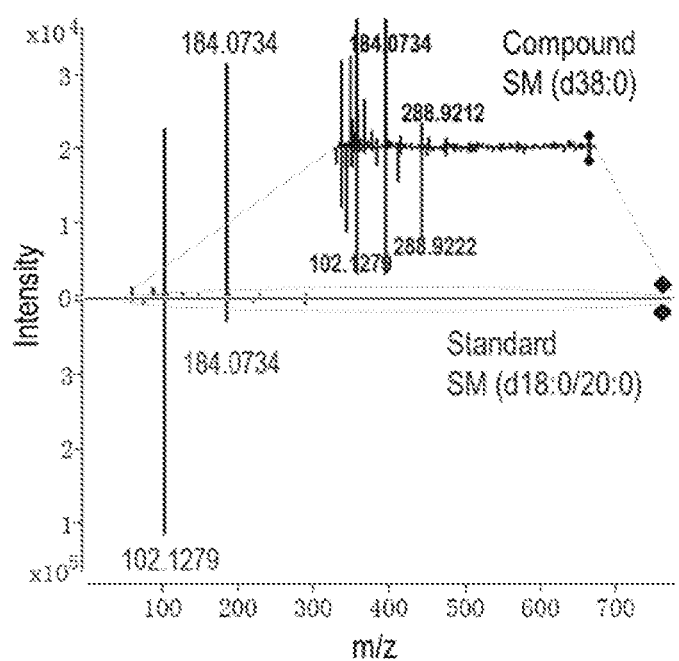
FIG. 15D shows the comparison of the MS/MS spectra of SM (d38:0) isolated from wild-type *Cordyceps* material and of the corresponding sphingolipid standard.
Figure 16A:
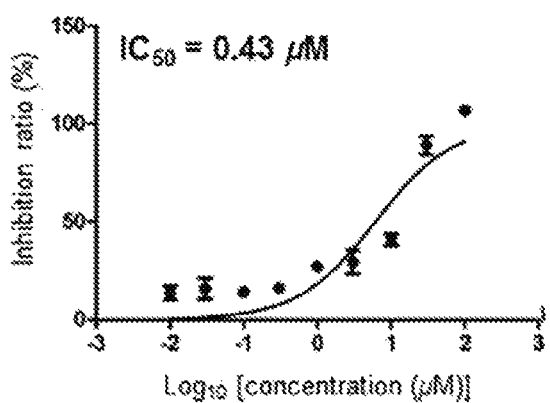
FIGS. 16A, 16B, 16C, 16D, and 16E provide diagrams showing the immunosuppressive effect of FTY720 and sphingolipid portions isolated from wild-type *Cordyceps* namely the sphingoid base portion, the ceramide portion, the glycosphingolipid portion and the sphingomyelin portion on a LPS-induced primary splenocyte proliferation model. Data are presented as the mean+/−SD of five independent experiments.
Figure 16B:
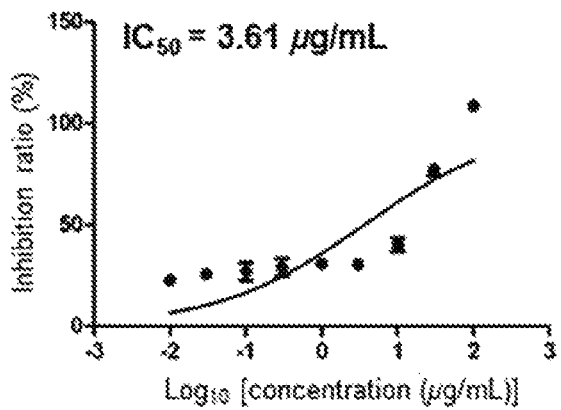
Figure 16C:
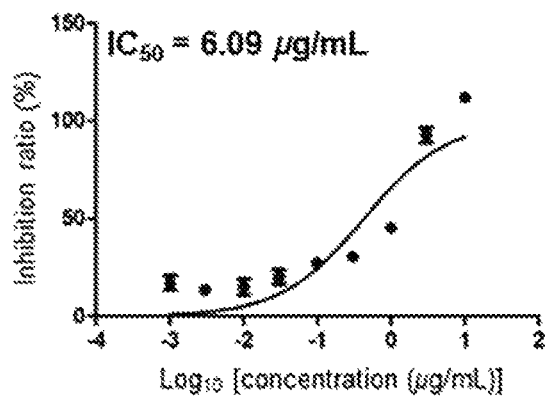
Figure 16D:
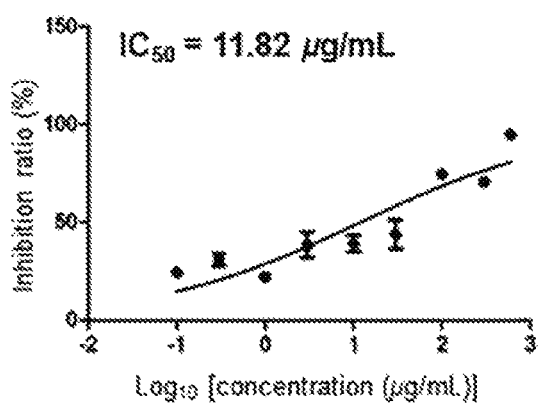
Figure 16E:
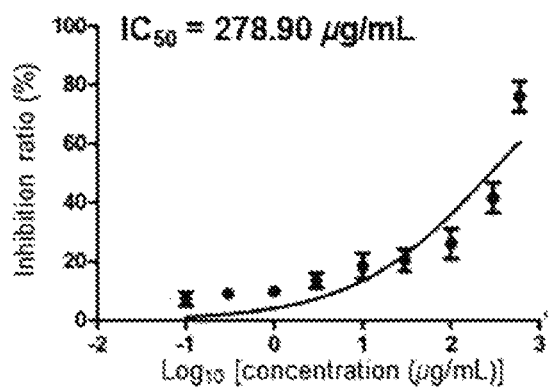
Figure 17A:
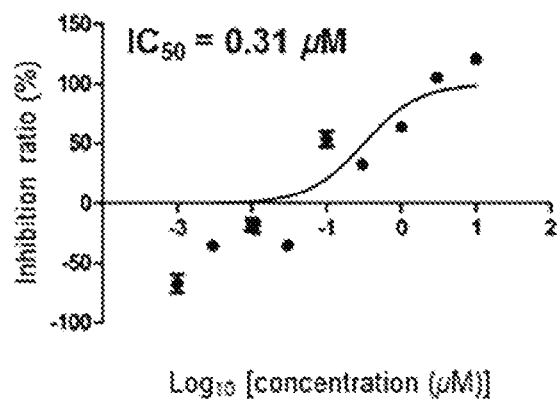
FIGS. 17A, 17B, 17C, 17D, and 17E show the immunosuppressive effect of FTY720 and sphingolipid portions isolated from wild-type *Cordyceps* namely the sphingoid base portion, the ceramide portion, the glycosphingolipid portion and the sphingomyelin portion on Con A-induced splenic lymphocytes. Data are presented as the mean+/−SD of five independent experiments.
Figure 17B:
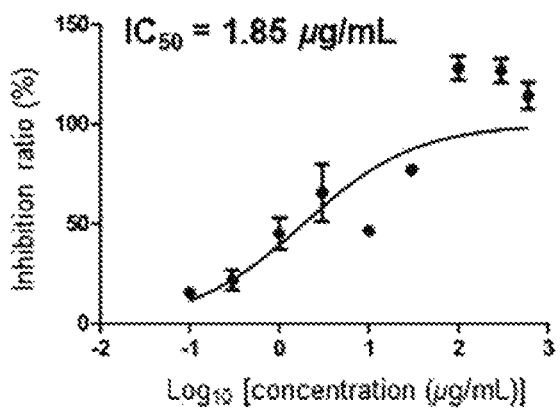
Figure 17C:
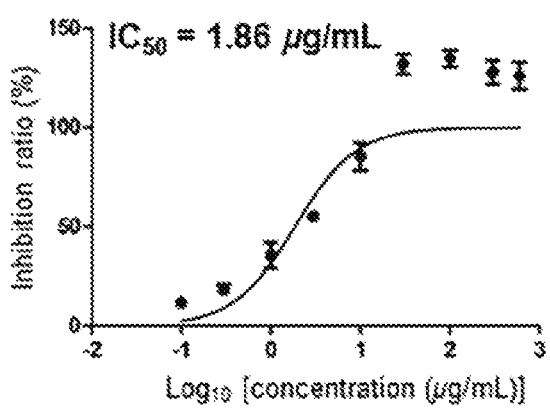
Figure 17D:
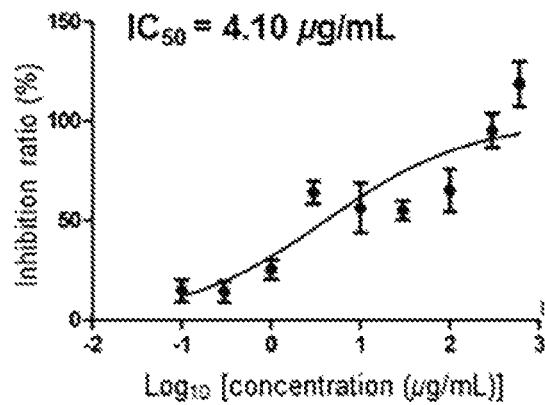
Figure 17E:
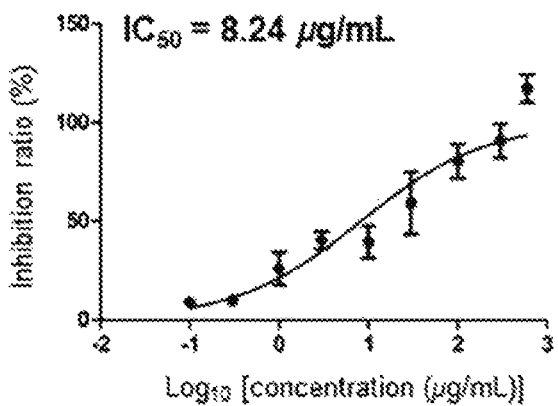

In order to give additional proof for the identification of SPLs, 34 SPL standards including 8 synthesized authentic SPLs (FIG. 11) were applied to confirm the mass spectrum and RT of SPLs in wild-type *Cordyceps*. FIG. 12, 13A to 13B and 14A to 14B show that comparison of the RT between SPL standards and SPLs identified from wild-type *Cordyceps*. As shown in FIG. 15A, the MS/MS spectrum of the protonated Cer (18:1/16:0) identified in wild *Cordyceps* at m/z 538 contains all the characteristic ions which arise from protonated Cer (d18:1/16:0) standard at m/z 538. Comparison of the MS/MS spectrum between Cer (d14:0/22:0) in wild *Cordyceps* and Cer (d18:0/18:0) standard indicates that the fragmentation pattern is similar except for the ions (e.g., m/z 228 and 210 for d14:0; m/z 284 and 266 for d18:0) reflecting the sphingoid backbone (FIG. 15B). As shown in FIG. 15C, the product ions pattern of SM (d14:1/22:0) is very similar with the standard SM (d18:1/18:0), but the minor difference contains different diagnostic ions for different sphingoid backbones. The feature ions are not observed for sphingoid backbone of dihydrosphingomyelins in the similar MS/MS spectrum of SM (d38:0) in wild-type *Cordyceps* and SM (d18:0/22:0) standard (FIG. 15D).

CONCLUSION

A total of 524 SPLs were identified from wild *Cordyceps* by means of UHPLC-UHD iFunnel Q-TOF MS, including 43 sphingoid bases, 301 ceramides, 103 glycosphingolipids and 77 sphingomyelins (Table 11), in which, 275 SPLs (bolded) including 12 sphingoid bases, 159 ceramides, 65 glycosphingolipids and 39 sphingomyelins were reported for the first time.

The LC-MS-based sphingolipidomics approach for identifying the isolated sphingolipid portions enabled the elimination of isotopic, adduct ion and ion-source cleavage interferences, and the discrimination of isobaric and isomeric species. To increase the number of identified SPLs, a comprehensive personal SPLs database has been introduced in the strategy. By improving both the detecting method and the screening library, the possibility of discovering SPLs could be improved. Simultaneously, 34 SPL standards including 8 synthesized authentic SPLs were used to confirm the identification of SPLs in wild-type *Cordyceps*. The third step is to verify identification of SPLs by UHPLC retention time. Based on assignments of SPLs, the linear regression model that is constructed by plotting carbon number v.s. retention time of SPLs shares common sphingoid backbone and the same unsaturated degree was used to verify identification of SPLs.

The feature ions, which are specific to the sphingoid backbone, the fatty acid chain and the headgroup, are decisive for the identification of SPLs, e.g. m/z 210 and m/z 364 for the assignation of C14 and C25 sphingoid backbones, respectively; m/z 400 and m/z 358 (diagnostic ions for C24 fatty acid chain with five double bonds) for the discovery of SPLs with polyunsaturated fatty acid chain; m/z 44 for the diagnosis of SPLs with 1-deoxyl sphingoid backbone. Additionally, the neutral loss information aids in the identification of polyhydroxyl SPLs, e.g. the ion at m/z 318 produces three ions at m/z 300, m/z 282 and m/z 264 by loss of H2O, which reveal that C18 sphingoid backbone possesses three hydroxyl groups.

Based on the structural elucidation of SPLs, newly characterized SPLs significantly enlarged structural diversification of four major classes of natural SPLs. The newly characterized sphingoid bases in *Cordyceps* represented three novel structural features. The first one is the high unsaturation degree (3 to 5) on C18 to C22 alkyl chain, as shown by compounds 10, 14 and 19 (see table 11). The second one is the multiple unsaturation degree occurs on odd-numbered sphingoid bases, as evidenced by compounds 20, 21, 27, 29 and 30. The third one is the as long as 22 carbon chain length of 1-deoxysphingosines, as can be seen from compounds 39-41. Since the maximum carbon chain length of the previously reported 1-deoxysphingosines is 20, our result provided the first example of the enlarged carbon chain length for this group of structures. Upon the comprehensive identification, the structural variations of sphingoid bases in *Cordyceps* can be summarized as 1) chain length varied from C14 to C23, 2) degree of unsaturation from 0 to 5 and 3) the number of hydroxyls varied from 1 to 3.

Ceramides are the most structurally diversified species in *Cordyceps*. A total of 301 ceramides were characterized from *Cordyceps* and 159 are novel ceramides. Ceramides are structurally formed via acylation of sphingoid backbone by long-chain fatty acids. Therefore, structural diversity of ceramides can be derived from either sphingoid backbone or fatty acids. In *Cordyceps*, a large number of novel ceramides are derived from sphingoid backbones that are not previously reported in ceramides, showing high variability of the sphingoid backbones for ceramides. The sphingoid bases in the new ceramides include: 1) C14, C15, C16 and C19 1-deoxysphingosine backbones (44, 49, 51 and 58), which represent the first example of 1-deoxysphingosine backbones with chain length other than C17 and C18 as backbones of ceramides; 2) sphingoid backbones with very short chain (C14) and long chain (C22, C24 and C25) (65, 85-87, 93); 3) new polyunsaturated sphingoid backbones, e.g. d19:3 and d20:2 ceramides (224, 230), which have two or more double bonds.

Novel ceramides arising from the alteration of fatty acids includes: 1) ceramides with polyhydroxyl fatty acid chains, as exemplified by ceramides 298-300 whose fatty acid chains were trihydroxylated; Similarly, dihydroxylated fatty acids linked to rare d16:0 and t14:1 sphingoid backbones instead of known t18:1 and t18:0 sphingoid backbone were identified for the first time (ceramides 301 and 302); 2) ceramides with extremely-long fatty acid chains, as represented by Cer (t18:0/42:1(dOH)) (309), Cer (t18:1/42:1 (dOH)) (312) and Cer (d16:0/35:1(dOH)) (301), indicating that chain length of fatty acid can be increased from C32 to C42; 3) ceramides with polyunsaturated fatty acids (with unsaturation degree of 4-6), as exemplified by compounds 308, 344, suggesting a largely increased unsaturation degree of fatty acid chain.

Novel glycosphingolipids can be represented by: 1) monohexosylceramides with t19:1 and t19:2 backbones (397, 399); 2) dihexosylceramides with new sphingoid backbones, such as d14:2, d16:2 and d19:2 (402, 409 and 417); 3) glycosphingolipids with three sugar moieties with new sphingoid backbones, e.g. C14, C15 and C16 sphingoid backbones (419, 423 and 425); t18:1 backbone (444); 4) glycosphingolipids with α-hydroxyl fatty acid chain, e.g. HexCer (d15:1/20:0(OH)) (445), Hex-Hex-Cer (d14:1/20:0 (OH)) and Hex-Hex-Cer (t18:1/24:1(OH)) (446, 447). The discovery of new sphingoid backbones in dihexosylceramides and glycosphingolipids with three sugar moieties, significantly increased the diversity of sphingoid backbones in glycosphingolipids (only C18 sphingoid backbone is reported in glycosphingolipids with three sugar moieties).

The features of novel sphingomyelins are predominantly those: 1) with new short sphingoid backbones; 2) with new long odd-numbered carbon sphingoid backbones including d19:2 (486) and t19:1 (496) backbones; 3) polyhydroxylated. The results illustrate that lots of novel sphingomyelins with very short sphingoid backbones are found in wild *Cordyceps*, e.g. d14:0, d14:1, d14:2 and d15:2 sphingomyelins (448, 450, 458, 462 and 466); t14:0, t14:1, t16:0 and t16:1 sphingomyelins (488-491). Additionally, the identification of polyhydroxylated sphingomyelins, e.g. SM (t14:0/25:3(OH)) (491), SM 018:0/24:1(OH)) (497), SM (t19:1/16:0(OH)) (496), indicate that the number of hydroxyls of sphingomyelins is increased from 3 to 4.

Example 3

Immunosuppressive Activity Assay

ICR mice were killed by cervical dislocation, and the spleens were removed aseptically. Mononuclear cell suspensions were prepared and re-suspended in RPMI 1640 medium (containing 10% FBS). The resulting splenic lymphocytes suspensions ($4 \times 10^6$ cells/mL) were cultured in 96-well plate (100 μL suspensions each well). In the control group, 100 μL 10% FBS in RPMI1640 was added into each well (five replicates of wells). In the LPS or Con A model group, 100 μL LPS or Con A (2.5 mg/L of final concentration) was added into each well (five replicates of wells). For the positive drug treatment group, 50 μL of LPS or Con A (2.5 mg/L of final concentration) and 50 μL of FTY720 with a set of final concentrations (0.001, 0.003, 0.01, 0.03, 0.1, 0.3, 1, 3 and 10 μM) were added into each well. In the test group, 50 μL of LPS or Con A (2.5 mg/L of final concentration) and 50 μL of the four SPL fractions with a set of final concentrations were added into each well. The final concentrations of the SPL portions were below: 0.01, 0.03, 0.1, 0.3, 1, 3, 10, 30 and 100 μg/mL for sphingoid bases and ceramides; 0.1, 0.3, 1, 3, 10, 30, 100, 300 and 600 μg/mL for sphingomyelins and glycosphingolipids. Five replicates of wells each concentration in the positive drug treatment group and test group. All splenic lymphocytes in different groups were cultured for 48 h. After the culture, 20 μL of MTT was pulsed each well for a 4 h of incubation. After that, the mixture was centrifuged and the supernatant was removed. 150 μL of DMSO was added into each well for 10 min shaking. Then the $OD_{490}$ readings were taken with a microplate reader (Bio Tek, Tigan Street Winooski, Vt., USA). The inhibitory concentration of the compound that reduced cell proliferation by 50% ($IC_{50}$ values) were determined by using the GraghPad Prism 5 software. Student's t-test was used to analyze data and compare the groups.

Immunosuppressive activity assays of the four SPL portions showed inhibition on LPS and Con A induced proliferation of primary splenic lymphocyte in a dose-dependent manner (FIG. 16A to 17E). As shown in FIG. 16A to 16E, in LPS-induced primary splenocyte proliferation model, the $IC_{50}$ values of the sphingoid base, ceramide, glycosphingolipid, sphingomyelin portions and positive drug FTY720 were 3.61, 6.09, 11.82, 278.90 and 0.15 µg/mL (0.43 µM), respectively. In Con A-induced primary splenocyte proliferation model, the $IC_{50}$ values of the sphingoid base, ceramide, glycosphingolipid, sphingomyelin portions and positive drug FTY720 were 1.85, 1.86, 8.24, 4.18 and 0.11 µg/mL (0.31 µM) (FIG. 17A to 17E), respectively. The results revealed that in particular the sphingoid base portion isolated from wild-type *Cordyceps* had the most potent immunosuppressive activity.

TABLE 11

524 SPLs identified including 275 new SPLs (bolded) from wild *Cordyceps* by using UHPLC-UHD iFunnel Q-TOF MS/MS

| No. | Name | Formula | RT | Score | Diff (ppm) | Theoretical [M + H]+ m/z | [M + H]+ m/z | MS/MS fragment m/z |
|---|---|---|---|---|---|---|---|---|
| 1 | Sa (d14:0) | C14 H31 N O2 | 4.99 | 82.86 | 0.02 | 246.2428 | 246.2430 | 228.2321, 60.0443 |
| 2 | So (d14:1) | C14 H29 N O2 | 4.40 | 80.77 | -2.03 | 244.2271 | 244.2275 | 226.1296, 60.0436 |
| 3 | So (d14:2) | C14 H27 N O2 | 3.25 | 85.66 | -1.93 | 242.2115 | 242.2115 | 224.2015, 206.1881, 60.0440 |
| 4 | So (d14:3) | C14 H25 N O2 | 2.10 | 65.07 | -0.18 | 240.1958 | 240.1958 | 222.1917, 60.0445 |
| 5 | So (d15:1) | C15 H31 N O2 | 6.70 | 68.91 | -1.77 | 258.2428 | 258.2429 | 240.2321, 222.1492 |
| 6 | So (d16:1) | C16 H33 N O2 | 7.05 | 64.91 | -2.12 | 272.2584 | 272.2585 | 254.2504, 60.0420 |
| 7 | Sa (d17:0) | C17 H37 N O2 | 5.15 | 99.28 | 0.80 | 288.2897 | 288.2900 | 270.2799 |
| 8 | Sa (d18:0) | C18 H39 N O2 | 6.97 | 79.10 | -2.56 | 302.3054 | 302.3052 | 284.2957, 266.2838, 254.278, 60.0445 |
| 9 | So (d18:1) | C18 H37 N O2 | 6.60 | 90.13 | -3.23 | 300.2897 | 300.2890 | 282.2510, 264.2360, 60.0441 |
| 10 | So (d18:5) \* | C18 H29 N O2 | 2.67 | 97.56 | -0.36 | 292.2271 | 292.2272 | 274.2159 |
| 11 | So (d19:1) | C19 H39 N O2 | 8.25 | 74.08 | -1.60 | 314.3054 | 314.3049 | 296.2948, 60.0438 |
| 12 | So (d19:2) | C19 H37 N O2 | 6.64 | 97.44 | 0.76 | 312.2899 | 312.2899 | 294.2788, 276.2700, 264.2691, 60.0445 |
| 13 | So (d20:2) | C20 H39 N O2 | 7.52 | 76.00 | -1.98 | 326.3054 | 326.3052 | 308.2914, 290.2954, 60.0443 |
| 14 | So (d20:3) | C20 H37 N O2 | 7.79 | 97.21 | 0.44 | 324.2899 | 324.2899 | 306.2820, 60.0418 |
| 15 | So (d22:1) | C22 H45 N O2 | 10.64 | 86.20 | -3.88 | 356.3523 | 356.3515 | 338.3456 |
| 16 | So (d22:1) isomer | C22 H45 N O2 | 10.17 | 82.52 | -2.07 | 356.3523 | 356.3517 | 338.3203 |
| 17 | So (d22:2) | C22 H43 N O2 | 8.60 | 96.71 | 0.03 | 354.3367 | 354.3366 | 336.3258 |
| 18 | So (d22:3) | C22 H41 N O2 | 7.67 | 91.82 | 0.24 | 352.3209 | 352.3209 | 334.3107, 316.3009, 60.0445 |
| 19 | So (d22:5) | C22 H37 N O2 | 6.92 | 63.69 | -4.81 | 348.2878 | 348.2878 | 330.2419, 60.0445 |
| 20 | So (t15:2) | C15 H29 N O3 | 3.59 | 98.64 | -0.37 | 272.2220 | 272.2220 | 254.1670, 60.0445 |
| 21 | So (t15:3) | C15 H27 N O3 | 2.97 | 72.86 | -0.61 | 270.2064 | 270.2065 | 252.1951 |
| 22 | Sa (t16:0) | C16 H35 N O3 | 5.12 | 85.55 | -0.02 | 290.2691 | 272.2527 | 254.2401, 236.1139, 242.2471, 60.0438 |
| 23 | Sa (t18:0) | C18 H39 N O3 | 6.67 | 97.40 | 0.92 | 318.3003 | 318.3006 | 300.2891, 282.2786, 264.2682, 60.0444 |
| 24 | So (t18:1) | C18 H37 N O3 | 6.40 | 97.11 | 0.52 | 316.2846 | 316.2848 | 298.2741, 280.2635, 262.2529, 250.2535, 60.0445 |
| 25 | So (t18:2) | C18 H35 N O3 | 6.87 | 84.21 | 1.80 | 314.2690 | 314.2697 | 296.2599, 278.2532, 60.0443 |
| 26 | So (t19:1) | C19 H39 N O3 | 7.32 | 98.97 | 0.06 | 330.3003 | 330.3004 | 312.2897, 294.2783, 60.0446 |
| 27 | So (t19:2) | C19 H37 N O3 | 6.90 | 98.38 | -0.29 | 328.2846 | 328.2845 | 310.2738, 292.2637, 274.2572, 262.2534, 60.0444 |
| 28 | So (t20:1) | C20 H41 N O3 | 7.29 | 69.92 | -2.16 | 344.3159 | 344.3154 | 326.2834, 308.2549, 60.0445 |
| 29 | So (t21:3) | C21 H39 N O3 | 9.25 | 88.05 | -2.07 | 354.3003 | 354.3002 | 336.2901 |
| 30 | So (t21:4) | C21 H37 N O3 | 7.94 | 72.60 | 1.27 | 352.2853 | 352.2853 | 334.2744, 316.2596 |
| 31 | Sa (t22:0) | C22 H47 N O3 | 8.02 | 98.41 | -1.43 | 374.3629 | 374.3624 | 356.3153, 338.3074, 320.2462 |
| 32 | So (t22:1) | C22 H45 N O3 | 8.10 | 75.99 | -2.15 | 372.3472 | 372.3466 | 354.3018, 336.3284 |
| 33 | So (t22:2) | C22 H43 N O3 | 7.59 | 63.48 | -2.94 | 370.3316 | 370.3312 | 352.2858, 334.2853, 316.2329, 60.0444 |
| 34 | So (t23:4) | C23 H41 N O3 | 9.50 | 74.92 | 1.12 | 380.3159 | 380.3161 | 362.3060 |
| 35 | So (m14:3) | C14 H25 N O | 3.72 | 84.63 | -0.95 | 224.2009 | 224.2014 | 206.1902, 194.1919 |
| 36 | Sa (m17:0) | C17 H37 N O | 6.74 | 86.06 | 1.37 | 272.2948 | 272.2952 | 254.2502 |
| 37 | Sa (m18:0) | C18 H39 N O | 7.20 | 98.31 | -1.73 | 286.3104 | 286.3110 | 268.2989 |
| 38 | So (m18:1) | C18 H37 N O | 6.95 | 83.22 | 0.68 | 284.2948 | 284.2948 | 266.2868 |
| 39 | So (m22:1) | C22 H45 N O | 11.12 | 96.58 | 0.53 | 340.3577 | 340.3577 | 322.3447 |
| 40 | So (m22:2) | C22 H43 N O | 9.47 | 99.21 | -0.76 | 338.3417 | 338.3416 | 320.3321 |
| 41 | So (m22:3) | C22 H41 N O | 7.60 | 98.61 | 0.64 | 336.3261 | 336.3263 | 318.3153 |
| 42 | So (m22:3) isomer | C22 H41 N O | 9.92 | 84.94 | 0.03 | 336.3261 | 336.3261 | 318.3134 |
| 43 | Sphingofungin A | C21 H41 N3 O6 | 9.34 | 89.37 | -1.50 | 432.3068 | 432.3064 | 414.3447, 396.3327, 378.3281 |
| 44 | Cer (m14:2/18:2) | C32 H57 N O2 | 10.78 | 88.80 | -3.12 | 488.4462 | 488.4452 | 470.3669, 226.2164, 208.2063, 196.2068, 44.0482 |
| 45 | Cer (m14:3/18:2) | C32 H55 N O2 | 10.52 | 95.97 | -0.47 | 486.4306 | 486.4305 | 468.4108, 224.2015, 206.1907, 194.1904, 44.0483 |

TABLE 11-continued

524 SPLs identified including 275 new SPLs (bolded) from wild *Cordyceps* by using UHPLC-UHD iFunnel Q-TOF MS/MS

| No. | Name | Formula | RT | Score | Diff (ppm) | Theoretical [M + H]+ m/z | [M + H]+ m/z | MS/MS fragment m/z |
|---|---|---|---|---|---|---|---|---|
| 46 | Cer (m14:3/18:2) isomer | C32 H55 N O2 | 9.27 | 79.44 | −5.25 | 486.4306 | 486.4282 | 468.3868, 206.1906 |
| 47 | Cer (m14:3/24:1) | C38 H69 N O2 | 14.27 | 96.33 | −1.41 | 572.5401 | 572.5395 | 554.5282, 224.2013, 206.1909, 194.1909, 44.0484 |
| 48 | Cer (m151/5:0) | C20 H39 N O2 | 8.55 | 99.05 | 1.22 | 326.3054 | 326.3058 | 308.2948, 224.2011 |
| 49 | Cer (m15:2/18:2) | C33 H59 N O2 | 11.68 | 98.70 | 1.10 | 502.4619 | 502.4613 | 484.4546, 240.2323, 222.2219, 210.2215, 44.0483 |
| 50 | Cer (m15:3/18:1) | C33 H59 N O2 | 11.40 | 90.67 | −1.07 | 502.4619 | 502.4617 | 484.4170, 238.2164, 220.2065, 208.2060, 44.0482 |
| 51 | Cer (m16:3/18:1) | C34 H61 N O2 | 11.88 | 86.43 | −3.35 | 516.4775 | 516.4757 | 498.4709, 252.2318, 234.2216, 222.2223, 44.0483 |
| 52 | Cer (m16:3/22:1) | C38 H69 N O2 | 14.68 | 76.67 | 1.40 | 572.5401 | 572.5403 | 554.5358, 252.2135, 234.2220, 222.2222, 44.0483 |
| 53 | Cer (m18:2/3:0) | C21 H39 N O2 | 7.82 | 99.01 | −0.02 | 338.3054 | 338.3050 | 264.2679 |
| 54 | Cer (m18:2/19:0) | C37 H71 N O2 | 15.28 | 95.01 | −0.75 | 562.5558 | 562.5555 | 544.5445, 282.2789, 264.2681, 252.2704, 44.0484 |
| 55 | Cer (m18:3/18:1) | C36 H65 N O2 | 12.98 | 97.15 | −0.21 | 544.5088 | 544.5088 | 526.4965, 280.2627, 262.2525, 250.2529, 44.0483 |
| 56 | Cer (m18:3/18:2) | C36 H63 N O2 | 12.22 | 94.15 | −0.39 | 542.4932 | 542.4931 | 524.4831, 280.2628, 262.2521, 250.2531, 44.0483 |
| 57 | Cer (m18:5/5:0) | C23 H37 N O2 | 7.53 | 99.45 | 0.87 | 360.2897 | 360.2900 | 276.2616, 258.2229 |
| 58 | Cer (m19:4/16:0) | C35 H63 N O2 | 10.78 | 97.11 | −1.79 | 512.4932 | 512.4923 | 512.4818, 292.2627, 274.2528, 262.2527, 44.0482 |
| 59 | Cer (m19:3/17:0) | C35 H65 N O2 | 13.43 | 95.84 | −0.78 | 532.5088 | 532.5093 | 514.4972, 294.2784, 276.2681, 264.2681, 44.0483 |
| 60 | Cer (d14:0/16:0) | C30 H61 N O3 | 11.35 | 93.31 | 1.77 | 484.4724 | 484.4710 | 466.4612, 448.4499, 246.2411, 228.2317, 210.2203, 198.2203 |
| 61 | Cer (d14:0/18:0) | C32 H65 N O3 | 12.47 | 96.42 | −1.61 | 512.5037 | 512.5031 | 494.4912, 476.4834, 246.2453, 228.2326, 210.2220, 198.2216, 60.0445 |
| 62 | Cer (d14:0/18:1) | C32 H63 N O3 | 11.67 | 84.13 | −3.03 | 510.4881 | 510.4865 | 492.4745, 474.4684, 462.3501, 246.2431, 228.2322, 210.2218, 198.2218, 60.0444 |
| 63 | Cer (d14:0/20:0) | C34 H69 N O3 | 13.68 | 98.35 | −0.79 | 540.535 | 540.5453 | 522.5236, 504.5230, 246.2427, 228.2325, 210.2221, 198.2220, 60.0445 |
| 64 | Cer (d14:0/22:0) | C36 H73 N O3 | 15.08 | 99.04 | −0.34 | 568.5663 | 568.5661 | 550.5549, 532.5438, 246.2438, 228.2325, 210.2220, 198.2221, 60.0444 |
| 65 | Cer (d14:0/23:0) | C37 H75 N O3 | 15.77 | 95.74 | −1.36 | 582.5820 | 582.5813 | 564.5697, 546.5581, 246.2430, 228.2430, 228.2223, 210.2217, 198.2223, 60.0444 |
| 66 | Cer (d14:0/24:0) | C38 H77 N O3 | 16.38 | 96.05 | −0.79 | 596.5976 | 596.5982 | 578.5862, 560.5761, 246.2435, 228.2324, 210.2222, 198.2221, 60.0444 |
| 67 | Cer (d16:0/20:0) | C36 H73 N O3 | 15.06 | 98.41 | −1.11 | 568.5663 | 568.5669 | 550.5550, 532.5435, 520.5305, 274.2729, 256.2626, 238.2517, 226.2522, 60.0439 |
| 68 | Cer (d16:0/22:0) | C38 H77 N O3 | 16.40 | 97.75 | −0.80 | 596.5976 | 596.5973 | 578.5862, 560.5761, 274.2731, 256.2637, 238.2533, 226.253, 60.0444 |
| 69 | Cer (d16:0/23:0) | C39 H79 N O3 | 17.02 | 89.50 | −2.81 | 610.6133 | 610.6120 | 592.6018, 574.5929, 274.2718, 256.2638, 238.2528, 226.2522, 60.0444 |
| 70 | Cer (d18:0/16:0) | C34 H69 N O3 | 13.70 | 98.72 | −0.27 | 540.5350 | 540.5349 | 522.5236, 504.5130, 302.3046, 284.2944, 266.2841, 254.2839, 60.0445 |
| 71 | Cer (d18:0/17:0) | C35 H71 N O3 | 14.51 | 63.16 | 7.99 | 554.5507 | 554.5472 | 536.5386, 518.5276, 302.3016, 284.2929, 266.2833, 60.0438 |
| 72 | Cer (d18:0/18:0) | C36 H73 N O3 | 15.17 | 98.27 | −1.19 | 568.5663 | 568.5669 | 550.5544, 532.5438, 302.3084, 284.2946, 266.2841, 254.2842, 60.0444 |
| 73 | Cer (d18:0/18:1) | C36 H71 N O3 | 14.85 | 95.87 | −0.83 | 566.5507 | 566.5511 | 550.5550, 532.5434, 520.5240, 502.5314, 302.3084, 284.2948, 266.2843, 254.2844, 60.0445 |
| 74 | Cer (d18:0/18:2) | C36 H69 N O3 | 13.98 | 65.50 | −2.34 | 564.5320 | 564.5348 | 546.5240, 528.5161, 516.5123, 284.2871, 254.2837, 60.0444 |
| 75 | Cer (d18:0/20:0) | C38 H77 N O3 | 16.40 | 96.69 | −0.81 | 596.5976 | 596.5982 | 578.5863, 560.5765, 302.3031, 284.2945, 266.2836, 60.0437 |
| 76 | Cer (d18:0/22:0) | C40 H81 N O3 | 17.72 | 95.99 | −2.10 | 624.6289 | 624.6277 | 606.6163, 588.6055, 302.3052, 284.2949, 266.2838, 254.2844, 60.0444 |
| 77 | Cer (d18:0/22:0) isomer | C40 H81 N O3 | 17.97 | 89.99 | −3.09 | 624.6289 | 624.6275 | 606.6174, 588.6058, 302.3078, 284.2948, 266.2840, 254.2833, 60.0444 |
| 78 | Cer (d18:0/23:0) | C41 H83 N O3 | 18.47 | 85.94 | −3.16 | 638.6446 | 638.6433 | 620.6329, 602.6228, 302.3032, 284.2955, 266.2831, 254.2871, 60.0445 |
| 79 | Cer (d18:0/24:0) | C42 H85 N O3 | 19.32 | 92.59 | −2.90 | 652.6602 | 652.6588 | 634.6487, 616.6352, 302.3084, 284.2948, 266.2841, 254.2843, 60.0445 |
| 80 | Cer (d18:0/25:0) | C43 H87 N O3 | 20.30 | 88.62 | −3.50 | 666.6759 | 666.6737 | 648.6634, 630.6514, 302.3073, 284.2943, 266.2824, 254.2831, 60.0445 |
| 81 | Cer (d18:0/26:0) | C44 H89 N O3 | 21.17 | 90.71 | −2.91 | 680.6915 | 680.6901 | 662.6796, 644.6697, 302.3083, 284.2947, 266.2844, 254.2847, 60.0445 |
| 82 | Cer (d20:0/25:0) | C45 H91 N O3 | 21.84 | 82.72 | −3.64 | 694.7072 | 694.7056 | 676.6960, 658.6845, 330.3371, 312.3255, 294.3154, 282.3139, 60.0445 |
| 83 | Cer (d20:0/26:0) | C46 H93 N O3 | 22.40 | 91.72 | −2.57 | 708.7228 | 708.7216 | 690.7108, 672.6992, 660.6947, 330.3376, 312.3259, 294.3168, 282.3158, 60.0445 |
| 84 | Cer (d20:0/27:0) | C47 H95 N O3 | 22.90 | 87.17 | −3.46 | 722.7385 | 722.7365 | 704.7256, 686.7147, 358.3704, 340.3566, 322.3473, 310.3485, 60.0445 |
| 85 | Cer (d22:0/26:0) | C48 H97 N O3 | 23.29 | 94.06 | −2.63 | 736.7541 | 736.7526 | 718.7423, 700.7305, 358.3706, 340.3573, 322.3466, 60.0444 |
| 86 | Cer (d24:0/26:0) | C50 H101 N O3 | 24.22 | 83.57 | −1.74 | 764.7854 | 764.7829 | 746.7729, 728.7612, 386.4028, 368.3890, 350.3746 338.3770, 60.0444 |
| 87 | Cer (d25:0/24:0) | C49 H99 N O3 | 23.75 | 88.87 | −3.37 | 750.7698 | 750.7671 | 732.7573, 714.7453, 382.4034, 364.3927, 352.3752, 60.0442 |
| 88 | Cer (d18:0/16:0(OH)) | C34 H69 N O4 | 13.17 | 70.07 | −2.68 | 556.5299 | 556.529 | 538.5192, 520.5085, 502.4947, 490.4969, 302.3046, 284.2952, 266.2845, 254.2844, 60.0444 |
| 89 | Cer (d18:0/20:0(OH)) | C38 H77 N O4 | 15.70 | 64.18 | −4.15 | 612.5925 | 612.5923 | 594.5814, 576.5713, 558.5542, 302.3026, 284.2956, 266.2837, 254.2809, 60.0444 |
| 90 | Cer (d18:0/24:0(OH)) | C42 H85 N O4 | 18.57 | 93.69 | −1.60 | 668.6551 | 668.6543 | 650.6424, 632.6333, 614.6246, 602.6232, 302.3037, 284.2948, 266.2842, 254.284, 60.0444 |
| 91 | Cer (d20:0/26:0(OH)) | C46 H93 N O4 | 21.87 | 86.66 | −2.04 | 724.7177 | 724.7167 | 706.7041, 688.6884, 312.3260, 294.3125, 60.0446 |

TABLE 11-continued

524 SPLs identified including 275 new SPLs (bolded) from wild *Cordyceps* by using UHPLC-UHD iFunnel Q-TOF MS/MS

| No. | Name | Formula | RT | Score | Diff (ppm) | Theoretical [M + H]$^+$ m/z | [M + H]$^+$ m/z | MS/MS fragment m/z |
|---|---|---|---|---|---|---|---|---|
| 92 | Cer (d22:0/25:0(OH)) | C47 H95 N O4 | 22.40 | 81.20 | −3.67 | 738.7334 | 738.7309 | 720.7174, 702.7103, 684.5929, 340.3558, 322.3416, 310.3420, 60.044 |
| 93 | Cer (t14:0/14:0) | C28 H57 N O4 | 9.32 | 97.85 | −1.34 | 472.4360 | 472.4356 | 454.2674, 436.3568, 208.2068, 60.0443 |
| 94 | Cer (t18:0/16:0) | C34 H69 N O4 | 12.48 | 96.83 | 2.11 | 556.5299 | 556.5288 | 538.5185, 520.5069, 318.2989, 300.2874, 282.2780, 264.2680, 252.2713, 60.0438 |
| 95 | Cer (t18:0/16:1) | C34 H67 N O4 | 12.66 | 74.58 | −1.17 | 554.5143 | 554.5137 | 536.5047, 518.4890, 318.3003, 300.2896, 282.2795, 264.2687, 252.2690, 60.0445 |
| 96 | Cer (t18:0/17:0) | C35 H71 N O4 | 13.11 | 73.70 | 1.17 | 570.5456 | 570.5451 | 552.5263, 534.5221, 518.6171, 334.5061, 318.3001, 300.2903, 282.2794, 264.2681, 252.2698, 60.0445 |
| 97 | Cer (t18:0/17:1) | C35 H69 N O4 | 13.20 | 72.43 | 1.82 | 568.5300 | 568.5295 | 550.5195, 532.5077, 514.4987, 502.4990, 318.2974, 318.3004, 300.2895, 282.2794, 264.2682, 252.2678, 60.0444 |
| 98 | Cer (t18:0/18:0) | C36 H73 N O4 | 13.75 | 98.04 | −0.38 | 584.5612 | 584.5611 | 566.5493, 548.5379, 530.5316, 518.5301, 318.3004, 300.2895, 282.2794, 264.2686, 252.2691, 60.0445 |
| 99 | Cer (t18:0/18:1) | C36 H71 N O4 | 13.94 | 80.22 | 0.11 | 582.5456 | 582.5456 | 564.5340, 546.5215, 528.5087, 318.3002, 300.2893, 282.2791, 264.2687, 252.2687, 60.0444 |
| 100 | Cer (t18:0/18:2) | C36 H69 N O4 | 12.15 | 96.38 | 2.16 | 580.5287 | 580.5287 | 562.5163, 544.5061, 526.4970, 318.2998, 300.2886, 282.2788, 264.2679, 252.2683, 60.0439 |
| 101 | Cer (t18:0/19:1) | C37 H73 N O4 | 13.46 | 72.71 | −1.24 | 596.5607 | 596.5607 | 578.5343, 560.5363, 542.4854, 318.3007, 318.3011, 300.2898, 282.2921, 264.2686, 252.2690, 60.0446 |
| 102 | Cer (t18:0/20:0) | C38 H77 N O4 | 15.10 | 95.07 | −0.50 | 612.5923 | 612.5925 | 594.5811, 576.5722, 558.5618, 318.2991, 300.2888, 282.2785, 264.2679, 252.2689, 60.0445 |
| 103 | Cer (t18:0/20:1) | C38 H75 N O4 | 15.20 | 80.53 | −3.03 | 610.5751 | 610.5769 | 592.5672, 574.5573, 318.2991, 300.2892, 282.2791, 264.2686, 252.2692, 60.0438 |
| 104 | Cer (t18:0/21:0) | C39 H79 N O4 | 15.77 | 95.31 | −1.10 | 626.6077 | 626.6082 | 608.5954, 590.5868, 572.5736, 560.5743, 318.3002, 300.2892, 282.2791, 264.2684, 252.2689, 60.0444 |
| 105 | Cer (t18:0/21:1) | C39 H77 N O4 | 15.73 | 75.08 | −1.99 | 624.5925 | 624.5938 | 606.5831, 588.5529, 570.4213, 318.3005, 300.2898, 282.2791, 264.2687, 252.2690, 60.0445 |
| 106 | Cer (t18:0/22:0) | C40 H81 N O4 | 16.43 | 99.02 | 0.03 | 640.6238 | 640.6238 | 622.6119, 604.6010, 586.5907, 574.5893, 318.3004, 300.2897, 282.2795, 264.2687, 252.2691, 60.0445 |
| 107 | Cer (t18:0/22:1) | C40 H79 N O4 | 16.34 | 87.99 | 0.88 | 638.6082 | 638.6060 | 620.5993, 602.5904, 318.3001, 300.2894, 282.2794, 264.2686, 252.2690, 60.0445 |
| 108 | Cer (t18:0/23:0) | C41 H83 N O4 | 17.20 | 98.64 | −0.15 | 654.6395 | 654.6395 | 636.6284, 618.6171, 600.6059, 318.3009, 300.2895, 282.2797, 264.2688, 252.2691, 60.0445 |
| 109 | Cer (t18:0/23:1) | C41 H81 N O4 | 17.00 | 80.56 | 1.78 | 652.6238 | 652.6233 | 634.6136, 616.5993, 598.5534, 318.2999, 300.2890, 282.2793, 264.2685, 252.2680, 60.0439 |
| 110 | Cer (t18:0/24:0) | C42 H85 N O4 | 17.83 | 98.59 | −0.31 | 668.6551 | 668.6549 | 650.6435, 632.6327, 614.6206, 602.6235, 318.3003, 300.2894, 282.2796, 264.2688, 252.2688, 60.0445 |
| 111 | Cer (t18:0/24:1) | C42 H83 N O4 | 17.22 | 70.87 | 1.23 | 666.6395 | 666.6383 | 648.6237, 630.6147, 318.2999, 300.2893, 282.2791, 264.2683, 252.2688, 60.0444 |
| 112 | Cer (t18:0/24:2) | C42 H81 N O4 | 15.68 | 90.97 | 2.65 | 664.6238 | 664.6221 | 646.5980, 628.5949, 610.5137, 406.3669, 364.3572, 318.2947, 300.2905, 282.2787, 264.2682, 252.2680, 60.0438 |
| 113 | Cer (t18:0/24:5) | C42 H75 N O4 | 16.05 | 80.65 | −1.08 | 658.5769 | 658.5750 | 640.5572, 622.4898, 604.5243, 400.3674, 358.3593, 318.3116, 300.2900, 282.2790, 264.2683, 252.2692, 60.0438 |
| 114 | Cer (t18:0/25:0) | C43 H87 N O4 | 18.62 | 93.89 | −1.80 | 682.6708 | 682.6698 | 664.6592, 646.6489, 628.6402, 318.3007, 300.2895, 282.2792, 264.2688, 252.2687, 60.0445 |
| 115 | Cer (t18:0/26:0) | C44 H89 N O4 | 18.77 | 96.22 | −2.20 | 696.6864 | 696.6850 | 678.6762, 660.6663, 642.6543, 318.3009, 300.2903, 282.2795, 264.2686, 252.2674, 60.0444 |
| 116 | Cer (t18:0/27:0) | C45 H91 N O4 | 19.33 | 91.39 | 1.28 | 710.7021 | 710.7045 | 692.6832, 674.6883, 300.2912, 282.2786, 264.2683, 60.0444 |
| 117 | Cer (t18:0/26:0) isomer | C44 H89 N O4 | 19.48 | 96.19 | −2.22 | 696.6864 | 696.6850 | 678.6746, 660.6626, 318.3009, 300.2890, 282.2792, 264.2694, 252.2681, 60.0444 |
| 118 | Cer (t18:0/27:0) isomer | C45 H91 N O4 | 20.47 | 86.91 | −3.12 | 710.7021 | 710.7004 | 692.6925, 674.6793, 656.6145, 318.3012, 300.2883, 282.2791, 264.2674, 60.0446 |
| 119 | Cer (t18:0/25:1) | C43 H85 N O4 | 18.58 | 80.66 | 1.88 | 680.6551 | 680.6541 | 662.6531, 644.6406, 318.2999, 300.2890, 282.2793, 264.2682, 252.2694, 60.0444 |
| 120 | Cer (t18:0/26:1) | C44 H87 N O4 | 18.08 | 76.77 | −4.31 | 694.6708 | 694.6677 | 676.6412, 658.6339, 640.6337, 318.2991, 300.2894, 282.2789, 264.2680, 252.2414, 60.0439 |
| 121 | Cer (t18:0/26:5) | C44 H79 N O4 | 16.05 | 61.51 | 7.15 | 686.6082 | 686.6039 | 668.6174, 650.6051, 632.5979, 318.2995, 300.2918, 282.2780, 264.2683, 60.0438 |
| 122 | Cer (t19:0/18:1) | C37 H73 N O4 | 14.50 | 70.45 | 3.42 | 596.5612 | 596.5602 | 578.5495, 560.5412, 548.5348, 332.3153, 314.3049, 296.2946, 278.2842, 266.2574, 60.0438 |
| 123 | Cer (t19:0/18:2) | C37 H71 N O4 | 13.60 | 72.83 | 1.21 | 594.5451 | 594.5451 | 576.5337, 558.5162, 332.3162, 314.3056, 296.2948, 278.2834, 266.2282, 60.0440 |
| 124 | Cer (t20:0/26:0) | C46 H93 N O4 | 21.24 | 96.16 | −2.32 | 724.7177 | 724.7161 | 706.7055, 688.6957, 346.3329, 328.3209, 310.3114, 292.2996, 280.2978, 60.0444 |
| 125 | Cer (t20:0/26:1) | C46 H91 N O4 | 21.24 | 63.46 | −1.85 | 722.7009 | 722.7022 | 704.7011, 686.6849, 346.3299, 328.3222, 310.3095, 292.2997, 280.3009, 60.0445 |
| 126 | Cer (t20:0/30:1) | C50 H99 N O4 | 18.40 | 83.42 | −3.29 | 778.7627 | 778.7647 | 760.7500, 742.7370, 310.3111, 292.2998, 280.2998 |
| 127 | Cer (t20:0/31:1) | C51 H101 N O4 | 19.27 | 75.18 | −4.77 | 792.7782 | 792.7803 | 774.7702, 756.7553, 738.7353, 310.3082, 292.2988, 280.3001, 60.0444 |
| 128 | Cer (t22:0/25:0) | C47 H95 N O4 | 21.90 | 94.15 | −2.71 | 738.7316 | 738.7345 | 720.7216, 702.7125, 374.3682, 356.3524, 338.3409, 320.3314, 308.3336, 60.0444 |
| 129 | Cer (t22:0/26:0) | C48 H97 N O4 | 22.44 | 95.47 | −2.37 | 752.749 | 752.7474 | 734.7371, 716.7219, 698.7067, 374.3607, 356.3535, 338.3418, 320.3323, 308.3328, 60.0445 |
| 130 | Cer (t22:0/26:1) | C48 H95 N O4 | 22.47 | 61.42 | 0.05 | 750.7334 | 750.7345 | 732.7208, 714.7138, 374.3637, 356.3513, 338.3410, 320.3314, 308.3287, 60.0444 |
| 131 | Cer (t22:0/27:0) | C49 H99 N O4 | 22.92 | 93.63 | −2.63 | 766.7647 | 766.7630 | 748.7530, 730.7428, 374.3635, 356.3529, 338.3420, 320.3311, 308.3214, 60.0443 |
| 132 | Cer (t22:0/28:0) | C50 H101 N O4 | 23.35 | 95.82 | −1.75 | 780.7803 | 780.7786 | 762.7694, 744.7563, 726.7574, 374.3592, 356.3517, 338.3406, 320.3308, 308.3273, 60.0445 |
| 133 | Cer (t16:0/12:0(OH)) | C28 H57 N O5 | 7.67 | 80.92 | −5.28 | 488.4310 | 488.4285 | 470.3743, 236.2407, 60.0443 |
| 134 | Cer (t18:0/16:0(OH)) | C34 H69 N O5 | 12.05 | 91.03 | −2.65 | 572.5249 | 572.5237 | 554.4728, 542.4728, 536.5024, 518.4919, 500.4885, 318.2993, 300.2893, 282.2792, 264.2683, 252.2691, 60.0440 |
| 135 | Cer (t18:0/17:0(OH)) | C35 H71 N O5 | 12.61 | 65.94 | 3.03 | 586.5405 | 586.5392 | 568.5296, 550.5165, 532.5129, 512.4825, 318.2998, 300.2871, 282.2783, 264.2678, 60.0438 |

TABLE 11-continued

524 SPLs identified including 275 new SPLs (bolded) from wild *Cordyceps* by using UHPLC-UHD iFunnel Q-TOF MS/MS

| No. Name | Formula | RT | Score | Diff (ppm) | Theoretical $[M + H]^+$ m/z | $[M + H]^+$ m/z | MS/MS fragment m/z |
|---|---|---|---|---|---|---|---|
| 136 Cer (t18:0/17:4(OH)) | C35 H63 N O5 | 10.20 | 85.77 | −0.49 | 578.4774 | 578.4774 | 560.4948, 300.2878, 282.2789, 264.2681, 252.2725, 60.0444 |
| 137 Cer (t18:0/18:0(OH)) | C36 H63 N O5 | 13.20 | 96.03 | −0.08 | 600.5562 | 600.5565 | 582.5444, 564.5341, 546.5231, 528.5074, 318.2988, 300.2889, 282.2986, 264.2679, 252.2680, 60.0444 |
| 138 Cer (t18:0/20:0(OH)) | C38 H77 N O5 | 14.50 | 82.50 | −3.27 | 628.5875 | 628.5857 | 610.5772, 592.5657, 574.5547, 318.2995, 300.2892, 282.2792, 264.2683, 252.2689, 60.0444 |
| 139 Cer (t18:0/21:0(OH)) | C39 H79 N O5 | 15.15 | 93.93 | 0.48 | 642.6031 | 642.6031 | 624.5913, 606.5805, 588.5660, 570.4251, 318.3165, 300.2898, 282.2783, 264.2678, 252.2670, 60.0438 |
| 140 Cer (t18:0/22:0(OH)) | C40 H81 N O5 | 15.80 | 99.55 | −0.17 | 656.6188 | 656.6186 | 638.6073, 620.5966, 602.5860, 584.5751, 318.3005, 300.2900, 282.2798, 264.2691, 252.2691, 60.0445 |
| 141 Cer (t18:0/23:0(OH)) | C41 H83 N O5 | 16.45 | 99.00 | 0.13 | 670.6344 | 670.6345 | 652.6223, 634.6119, 616.6004, 598.5930, 318.3001, 300.2897, 282.2796, 264.2688, 252.2690, 60.0445 |
| 142 Cer (t18:0/23:1(OH)) | C41 H81 N O5 | 15.32 | 94.48 | −0.67 | 668.6188 | 668.6185 | 650.6076, 632.5961, 614.5852, 596.5374, 318.3008, 300.2895, 282.2794, 264.2685, 252.2694, 60.0444 |
| 143 Cer (t18:0/24:0(OH)) | C42 H85 N O5 | 17.13 | 98.90 | −0.24 | 684.6497 | 684.6497 | 666.6391, 648.6288, 630.6174, 612.6071, 318.3006, 300.2902, 282.2798, 264.2692, 252.2693, 60.0445 |
| 144 Cer (t18:0/24:1(OH)) | C42 H83 N O5 | 16.02 | 97.11 | −1.56 | 682.6344 | 682.6333 | 664.6214, 646.6117, 628.6013, 610.5933, 318.3001, 300.2894, 282.2796, 264.2688, 252.2686, 60.0445 |
| 145 Cer (t18:0/25:0(OH)) | C43 H87 N O5 | 17.83 | 98.68 | −0.38 | 698.6657 | 698.6653 | 680.6533, 662.6426, 644.6315, 626.6226, 614.6232, 318.3002, 300.2894, 282.2795, 264.2686, 252.2687, 60.0444 |
| 146 Cer (t18:0/26:0(OH)) | C44 H89 N O5 | 18.58 | 95.18 | −1.79 | 712.6814 | 712.6802 | 694.6694, 676.6593, 658.6466, 640.6314, 318.3008, 300.2892, 282.2794, 264.2685, 252.2697, 60.0444 |
| 147 Cer (d14:1/16:0) | C30 H59 N O3 | 11.07 | 85.53 | −2.51 | 482.4568 | 482.4561 | 464.4052, 226.2164, 208.2064, 196.2068, 60.0444 |
| 148 Cer (d14:1/18:0) | C32 H63 N O3 | 12.06 | 70.12 | 3.25 | 510.4881 | 510.4866 | 244.1701, 226.2159, 244.1489, 60.0443 |
| 149 Cer (d14:1/18:1) | C32 H61 N O3 | 11.32 | 75.17 | −1.78 | 508.4724 | 508.4715 | 490.4637, 226.2164, 208.2065, 196.2068, 60.0443 |
| 150 Cer (d14:1/18:2) | C32 H59 N O3 | 11.16 | 91.52 | −2.46 | 506.4568 | 506.4553 | 488.4472, 470.6828, 226.2163, 208.2048, 196.2048, 60.0438 |
| 151 Cer (d14:1/20:0) | C34 H67 N O3 | 13.25 | 60.57 | 2.67 | 538.5194 | 538.5200 | 520.5080, 502.4976, 490.4968, 226.2163, 208.2055, 196.2052, 60.0445 |
| 152 Cer (d14:1/20:4) | C34 H59 N O3 | 11.68 | 79.05 | 2.68 | 530.4568 | 530.4548 | 512.4422, 226.2152, 208.2064, 196.2070, 60.0442 |
| 153 Cer (d14:1/22:0) | C36 H71 N O3 | 14.63 | 98.78 | 0.32 | 566.5507 | 566.5507 | 548.5370, 530.5258, 226.2165, 208.2067, 196.2065, 60.0445 |
| 154 Cer (d14:1/22:4) | C37 H71 N O3 | 15.10 | 97.85 | −0.99 | 580.5663 | 580.5664 | 562.5615, 544.5448, 226.2158, 208.2063, 196.2063, 60.0444 |
| 155 Cer (d14:1/24:0) | C38 H75 N O3 | 16.03 | 85.79 | 0.26 | 594.5820 | 594.5817 | 576.5717, 558.5551, 546.5523, 226.2164, 208.2067, 196.2065, 60.0445 |
| 156 Cer (d14:2/16:0) | C30 H57 N O3 | 10.78 | 94.25 | 2.38 | 480.4411 | 480.4400 | 462.3710, 224.2009, 206.1906, 194.1890, 60.0445 |
| 157 Cer (d14:2/18:2) | C32 H57 N O3 | 11.06 | 77.82 | 3.59 | 504.4411 | 504.4390 | 242.1975, 224.1959, 206.1905, 194.1914, 60.0443 |
| 158 Cer (d14:2/20:4) | C34 H57 N O3 | 10.96 | 85.99 | 3.65 | 528.4411 | 528.4393 | 510.4281, 238.2157, 224.2026, 206.1893, 60.0438 |
| 159 Cer (d14:2/20:5) | C34 H55 N O3 | 10.48 | 86.16 | 4.11 | 526.4255 | 526.4235 | 508.4086, 206.1894, 60.0437 |
| 160 Cer (d14:2/20:6) | C34 H53 N O3 | 10.13 | 80.80 | 3.88 | 524.4098 | 524.4069 | 506.3812, 224.2058, 206.1891, 60.0437 |
| 161 Cer (d14:2/24:3) | C38 H67 N O3 | 14.15 | 88.75 | −3.97 | 586.5194 | 586.5169 | 568.5049, 538.4920, 224.2005, 206.1909, 194.1884, 60.0444 |
| 162 Cer (d14:2/25:3) | C39 H69 N O3 | 14.82 | 80.84 | −4.03 | 600.5350 | 600.5324 | 582.5183, 552.5139, 224.2065, 206.1907, 194.1917, 60.0444 |
| 163 Cer (d14:2/26:3) | C40 H71 N O3 | 15.53 | 88.32 | −3.66 | 614.5507 | 614.5484 | 596.5388, 566.5217, 224.2010, 206.1905, 194.1142, 60.0444 |
| 164 Cer (d15:1/20:0) | C35 H69 N O3 | 13.88 | 73.53 | −0.17 | 552.5350 | 552.5341 | 534.5190, 504.5190, 240.2322, 222.2219, 210.2216, 60.0444 |
| 165 Cer (d15:1/22:0) | C37 H73 N O3 | 15.08 | 87.15 | −0.67 | 580.5663 | 580.5656 | 562.5619, 544.5423, 240.2324, 222.2221, 210.2222, 60.0444 |
| 166 Cer (d15:1/22:1) | C37 H71 N O3 | 14.68 | 75.69 | −1.61 | 578.5507 | 578.5499 | 560.5363, 542.5317, 530.5252, 240.2324, 222.2220, 210.2218, 60.0444 |
| 167 Cer (d15:2/22:1) | C37 H69 N O3 | 14.00 | 69.76 | −1.63 | 576.5350 | 576.5342 | 558.5212, 238.2157, 220.2064, 208.2057, 60.0444 |
| 168 Cer (d16:1/22:0) | C38 H75 N O3 | 15.83 | 93.75 | 0.01 | 594.5820 | 594.5818 | 576.5789, 558.5592, 546.5678, 272.2603, 254.2479, 236.2373, 224.2377, 60.0444 |
| 169 Cer (d16:1/22:1) | C38 H73 N O3 | 15.21 | 80.88 | 2.30 | 592.5663 | 592.5669 | 574.5528, 556.5449, 252.2364, 236.2364, 224.2380, 60.0438 |
| 170 Cer (d16:1/22:2) | C38 H71 N O3 | 15.07 | 62.36 | 0.33 | 590.5507 | 590.5485 | 572.5410, 272.2396, 254.2482, 236.2374, 224.2377, 60.0444 |
| 171 Cer (d16:1/24:0) | C40 H79 N O3 | 17.21 | 93.81 | 0.54 | 622.6133 | 622.6125 | 604.6023, 586.5933, 574.5919, 254.2468, 236.2370, 224.2236, 60.0439 |
| 172 Cer (d16:2/22:2) | C38 H69 N O3 | 14.61 | 77.60 | 4.60 | 588.5350 | 588.5335 | 570.5212, 252.2318, 234.2216, 222.2207, 60.0439 |
| 173 Cer (d16:2/23:1) | C39 H73 N O3 | 15.53 | 80.53 | 3.43 | 604.5663 | 604.5646 | 586.5535, 568.5508, 252.2267, 234.2215, 222.2207, 60.0444 |
| 174 Cer (d16:2/23:2) | C39 H71 N O3 | 15.08 | 86.09 | 3.94 | 602.5507 | 602.5485 | 584.5293, 568.2318, 252.2321, 234.2216, 222.2215, 60.0444 |
| 175 Cer (d16:2/24:2) | C40 H73 N O3 | 16.08 | 75.32 | 3.60 | 616.5663 | 616.5642 | 598.5288, 252.2318, 234.2220, 222.2215, 60.0445 |
| 176 Cer (d18:1/14:1) | C32 H61 N O3 | 11.56 | 88.80 | −3.29 | 508.4724 | 508.4722 | 300.2695, 246.1842, 226.2684, 252.2678, 60.0443 |
| 177 Cer (d18:1/16:0) | C34 H67 N O3 | 13.25 | 92.16 | 2.67 | 538.5194 | 538.5200 | 520.5080, 502.4976, 490.4968, 300.2920, 282.2788, 264.2682, 252.2681, 60.0438 |
| 178 Cer (d18:1/16:1) | C34 H65 N O3 | 12.70 | 94.00 | −0.28 | 536.5037 | 536.5037 | 518.4883, 500.4830, 488.4807, 300.2890, 282.2789, 264.2688, 252.2689, 60.0444 |
| 179 Cer (d18:1/17:0) | C35 H69 N O3 | 13.88 | 80.51 | −0.37 | 552.5350 | 552.5345 | 534.5235, 516.5156, 504.5099, 282.2786, 264.2680, 252.2697, 60.0438 |
| 180 Cer (d18:1/17:1) | C35 H67 N O3 | 13.35 | 94.17 | 0.45 | 550.5194 | 550.5194 | 532.5075, 520.5060, 514.4981, 300.2866, 282.2784, 264.2683, 60.0439 |

TABLE 11-continued

524 SPLs identified including 275 new SPLs (bolded) from wild *Cordyceps* by using UHPLC-UHD iFunnel Q-TOF MS/MS

| No. | Name | RT | Score | Diff (ppm) | Formula | Theoretical [M+H]+ m/z | [M+H]+ m/z | MS/MS fragment m/z |
|---|---|---|---|---|---|---|---|---|
| 181 | Cer (d18:1/18:0) | 14.51 | 98.8 | −1.01 | C36 H71 N O3 | 566.5507 | 566.5512 | 548.5392, 530.5392, 300.2905, 282.2787, 264.2683, 252.2691, 60.0437 |
| 182 | Cer (d18:1/18:1) | 13.95 | 90.93 | −0.81 | C36 H69 N O3 | 564.5350 | 564.5355 | 546.5240, 528.5261, 300.2706, 282.2789, 264.2685, 252.2689, 60.0444 |
| 183 | Cer (d18:1/18:2) | 13.50 | 99.22 | −0.60 | C36 H67 N O3 | 562.5194 | 562.5197 | 544.5092, 526.4973, 282.2799, 264.2687, 252.2134, 60.0445 |
| 184 | Cer (d18:1/20:0) | 15.75 | 94.73 | −0.43 | C38 H75 N O3 | 594.5820 | 594.5823 | 576.5726, 558.5505, 282.2785, 264.2683, 252.2677, 60.0445 |
| 185 | Cer (d18:1/20:1) | 15.23 | 75.43 | −0.45 | C38 H73 N O3 | 592.5663 | 592.5668 | 574.5589, 556.5482, 300.2693, 282.2785, 264.2677, 252.2622, 60.0438 |
| 186 | Cer (d18:1/21:0) | 16.46 | 72.25 | 1.68 | C39 H77 N O3 | 608.5976 | 608.5974 | 590.5844, 572.5753, 282.2788, 264.2683, 252.2695, 60.0433 |
| 187 | Cer (d18:1/22:0) | 17.18 | 65.73 | 0.12 | C40 H79 N O3 | 622.6133 | 622.6122 | 604.5901, 586.5897, 574.5606, 300.2874, 282.2793, 264.2685, 252.2692, 60.0443 |
| 188 | Cer (d18:1/22:1) | 16.53 | 75.34 | −3.54 | C40 H77 N O3 | 620.5976 | 620.5969 | 602.5862, 584.5745, 300.2867, 282.2782, 264.2676, 252.2681, 60.0438 |
| 189 | Cer (d18:1/22:2) | 16.32 | 61.25 | −3.06 | C40 H75 N O3 | 618.5820 | 618.5790 | 600.5703, 582.5579, 300.2832, 282.2801, 264.2685, 252.2690, 60.0444 |
| 190 | Cer (d18:1/23:0) | 17.88 | 68.37 | −1.02 | C41 H81 N O3 | 636.6289 | 636.6282 | 618.6271, 600.6136, 588.6035, 282.2794, 264.2686, 252.2680, 60.0445 |
| 191 | Cer (d18:1/23:1) | 17.02 | 66.13 | 0.08 | C41 H79 N O3 | 634.6133 | 634.6129 | 616.5984, 598.5948, 300.2891, 282.2786, 264.2688, 252.2680, 60.0444 |
| 192 | Cer (d18:1/23:5) isomer | 13.16 | 75.79 | −3.03 | C41 H71 N O3 | 626.5507 | 626.5537 | 608.5416, 590.5322, 300.2876, 282.2781, 264.2680, 252.2646, 60.0438 |
| 193 | Cer (d18:1/24:0) | 18.65 | 70.23 | −0.73 | C42 H83 N O3 | 650.6446 | 650.6431 | 632.6388, 614.6308, 602.6239, 300.2876, 282.2794, 264.2686, 252.2689, 60.0444 |
| 194 | Cer (d18:1/24:1) | 17.81 | 64.02 | 1.52 | C42 H81 N O3 | 648.6289 | 648.6287 | 630.6203, 612.6077, 600.6053, 300.2895, 282.2793, 264.2688, 252.2689, 60.0444 |
| 195 | Cer (d18:1/24:2) | 17.59 | 70.45 | −2.54 | C42 H79 N O3 | 646.6133 | 646.6106 | 628.6036, 610.5821, 282.2786, 264.2679, 252.2686, 60.0439 |
| 196 | Cer (d18:1/24:5) | 13.16 | 83.53 | −2.66 | C42 H73 N O3 | 640.5663 | 640.5683 | 622.5577, 604.5419, 300.2869, 282.2816, 264.2679, 252.2646, 60.0438 |
| 197 | Cer (d18:1/25:0) | 19.59 | 72.04 | −0.01 | C43 H85 N O3 | 664.6602 | 664.6593 | 646.6523, 282.2787, 252.2657, 60.0435 |
| 198 | Cer (d18:1/25:1) | 18.60 | 63.55 | −3.53 | C43 H83 N O3 | 662.6446 | 662.6426 | 644.6228, 300.2881, 282.2784, 264.2683, 252.2673, 60.0444 |
| 199 | Cer (d18:1/25:2) | 18.41 | 61.26 | 1.29 | C43 H81 N O3 | 660.6289 | 660.6258 | 300.2914, 282.2794, 264.2686, 252.2697, 60.0445 |
| 200 | Cer (d18:1/25:4) | 16.64 | 70.95 | 5.11 | C43 H77 N O3 | 656.5976 | 656.5949 | 638.6064, 620.5934, 300.2920, 282.2783, 264.2673, 252.2687, 60.0437 |
| 201 | Cer (d18:1/26:0) | 20.51 | 77.01 | 1.09 | C44 H87 N O3 | 678.6759 | 678.6747 | 660.6770, 282.2806, 264.2682, 252.2684, 60.0444 |
| 202 | Cer (d18:1/26:1) | 19.23 | 69.78 | 2.34 | C44 H85 N O3 | 676.6602 | 676.6574 | 658.6508, 640.6382, 282.2785, 264.2684, 60.0438 |
| 203 | Cer (d18:1/26:4) | 14.50 | 94.37 | 2.07 | C44 H77 N O3 | 668.5976 | 668.5991 | 650.5900, 300.2882, 282.2813, 264.2679, 60.0437 |
| 204 | Cer (d18:1/26:4) isomer | 13.20 | 77.90 | 0.99 | C44 H77 N O3 | 668.5976 | 668.5989 | 650.5833, 632.5784, 300.2890, 282.2784, 264.2678, 252.2683, 60.0483 |
| 205 | Cer (d18:1/27:5) | 15.75 | 70.79 | −5.50 | C45 H79 N O3 | 682.6133 | 682.6174 | 664.6041, 646.5940, 300.2891, 282.2779, 252.2679, 60.0438 |
| 206 | Cer (d18:1/28:4) | 19.28 | 70.34 | −4.32 | C46 H83 N O3 | 698.6446 | 698.6412 | 300.2862, 282.2787, 264.2677, 60.0439 |
| 207 | Cer (d18:1/28:5) | 15.76 | 71.59 | −3.93 | C46 H81 N O3 | 696.6289 | 696.6324 | 678.6159, 660.6082, 300.2740, 282.2785, 264.2679, 252.2684, 60.0438 |
| 208 | Cer (d18:1/29:5) | 16.41 | 77.15 | −3.69 | C47 H83 N O3 | 710.6446 | 710.6476 | 692.6337, 674.6262, 300.2887, 282.2789, 264.2679, 252.2682, 60.0439 |
| 209 | Cer (d18:1/32:4) | 17.80 | 61.11 | −1.99 | C50 H91 N O3 | 754.7072 | 754.7036 | 736.6524, 718.6279, 282.2788, 264.2689, 60.0436 |
| 210 | Cer (d18:1/32:5) | 17.08 | 76.56 | −2.45 | C50 H89 N O3 | 752.6915 | 752.6944 | 734.6812, 716.6725, 300.2906, 282.2783, 264.2678, 252.2644, 60.0437 |
| 211 | Cer (d19:1/24:0) | 19.58 | 76.42 | 1.15 | C43 H85 N O3 | 664.6602 | 664.6588 | 646.6520, 296.3310, 278.2849, 266.2833, 60.0436 |
| 212 | Cer (d19:2/16:0) | 13.03 | 98.78 | −0.26 | C35 H67 N O3 | 550.5194 | 550.5194 | 532.5097, 514.4927, 502.4931, 312.2890, 294.2785, 276.2685, 264.2688, 60.0445 |
| 213 | Cer (d19:2/16:1) | 12.83 | 96.12 | −0.77 | C35 H65 N O3 | 548.5037 | 548.5042 | 312.2895, 294.2790, 276.2687, 264.2683, 60.0444 |
| 214 | Cer (d19:2/16:2) | 10.32 | 78.16 | −5.54 | C35 H63 N O3 | 546.4881 | 546.4856 | 528.4767, 510.4620, 498.4630, 294.2815, 276.2684, 264.2674, 60.0445 |
| 215 | Cer (d19:2/18:2) | 13.88 | 60.45 | −5.37 | C37 H67 N O3 | 574.5194 | 574.5164 | 294.2772, 276.2690, 264.2683 |
| 216 | Cer (d19:2/18:3) | 13.42 | 72.89 | 2.89 | C37 H65 N O3 | 572.5037 | 572.5013 | 554.4765, 312.2939, 294.2777, 276.2684, 60.0444 |
| 217 | Cer (d19:2/18:4) | 12.23 | 63.95 | 6.10 | C37 H63 N O3 | 570.4881 | 570.4846 | 552.5073, 534.4846, 312.2876, 294.2783, 276.2674, 264.2675, 60.0439 |
| 218 | Cer (d19:2/20:0) | 15.83 | 70.56 | −3.24 | C39 H75 N O3 | 606.5820 | 606.5815 | 588.5678, 570.5591, 294.2788, 276.2676, 264.2673, 60.0438 |
| 219 | Cer (d19:2/20:4) | 13.35 | 90.84 | 3.17 | C39 H67 N O5 | 598.5194 | 598.5176 | 580.5293, 562.5256, 312.3244, 294.2816, 276.2678, 264.2680, 60.0439 |
| 220 | Cer (d19:2/21:5) | 12.36 | 71.01 | −6.14 | C40 H67 N O3 | 610.5194 | 610.5235 | 592.5112, 574.5010, 294.2754, 276.2675, 264.2670, 60.0438 |
| 221 | Cer (d19:2/22:1) | 16.92 | 60.44 | −0.83 | C41 H77 N O3 | 632.5976 | 632.5950 | 614.5356, 294.2783, 276.2680, 264.2694, 60.0443 |
| 222 | Cer (d19:2/24:1) | 17.70 | 66.77 | −2.57 | C43 H81 N O3 | 660.6267 | 660.6268 | 642.6215, 624.5982, 612.6075, 294.2784, 276.2682, 264.2677, 60.0444 |
| 223 | Cer (d19:2/24:2) | 17.91 | 61.37 | 2.94 | C43 H79 N O3 | 658.6133 | 658.6100 | 640.6160, 294.2813, 276.2669, 264.2683, 60.0438 |
| 224 | Cer (d19:3/17:4) | 11.28 | 70.54 | 2.13 | C36 H59 N O3 | 554.4568 | 554.4541 | 536.4232, 292.2621, 274.2524, 262.2497, 60.0438 |
| 225 | Cer (d20:1/24:1) | 19.54 | 80.43 | −2.35 | C44 H85 N O3 | 676.6602 | 676.6584 | 658.6530, 310.3071, 292.2995, 280.3015, 60.0438 |
| 226 | Cer (d20:1/25:0) | 21.29 | 65.70 | −1.52 | C45 H89 N O3 | 692.6915 | 692.6894 | 310.3110, 292.2997, 280.2976, 60.0443 |

TABLE 11-continued

524 SPLs identified including 275 new SPLs (bolded) from wild *Cordyceps* by using UHPLC-UHD iFunnel Q-TOF MS/MS

| No. | Name | Formula | RT | Score | Diff (ppm) | Theoretical [M + H]+ m/z | [M + H]+ m/z | MS/MS fragment m/z |
|---|---|---|---|---|---|---|---|---|
| 227 | Cer (d20:1/26:0) | C46 H91 N O3 | 22.05 | 63.42 | 1.16 | 706.7072 | 706.7055 | 688.7034, 670.6835, 328.3253, 310.3105, 292.2999, 280.2994 |
| 228 | Cer (d20:1/26:2) | C46 H87 N O3 | 21.17 | 60.14 | -3.86 | 702.6759 | 702.6720 | 684.6607, 338.3423, 328.3002, 310.3127, 292.2998, 280.2994, 60.0444 |
| 229 | Cer (d20:1/27:0) | C47 H93 N O3 | 22.55 | 64.89 | -0.93 | 720.7228 | 720.7207 | 702.7083, 684.7016, 310.3095, 292.2998, 280.3012, 60.0444 |
| 230 | Cer (d20:2/28:0) | C48 H93 N O3 | 21.24 | 83.22 | -4.72 | 732.7228 | 732.7198 | 714.7022, 326.3055, 308.2946, 290.2848, 278.2872, 60.0445 |
| 231 | Cer (d21:1/28:0) | C49 H97 N O3 | 23.42 | 68.25 | -1.47 | 748.7541 | 748.7518 | 730.6799, 324.3259, 306.3160, 294.3166, 60.0442 |
| 232 | Cer (d22:1/26:2) | C48 H91 N O3 | 22.42 | 74.07 | -4.33 | 730.7072 | 730.7034 | 712.7041, 356.3303, 338.3414, 320.3307, 308.3314, 60.0442 |
| 233 | Cer (d22:1/26:0) | C48 H95 N O3 | 22.99 | 62.45 | 1.73 | 734.7385 | 734.7370 | 716.7297, 698.7081, 338.3418, 320.3309, 308.3295, 60.0445 |
| 234 | Cer (d22:1/27:2) | C49 H93 N O3 | 22.89 | 71.79 | -5.40 | 744.7228 | 744.7184 | 726.6413, 320.3312, 308.3324, 60.0445 |
| 235 | Cer (d22:1/28:0) | C50 H99 N O3 | 23.85 | 78.70 | -0.61 | 762.7697 | 762.7679 | 744.7567, 726.7396, 338.3407, 320.3318, 308.3309, 60.0444 |
| 236 | Cer (d14:1/18:3(OH)) | C32 H57 N O4 | 13.62 | 97.64 | -0.54 | 520.4360 | 520.4354 | 226.2176, 208.2065, 196.2062, 60.0445 |
| 237 | Cer (d14:2/14:3(OH)) | C28 H47 N O4 | 9.03 | 89.60 | -1.61 | 462.3578 | 462.3571 | 444.3234, 206.1909, 60.0432 |
| 238 | Cer (d18:1/26:2(OH)) | C44 H83 N O4 | 18.55 | 87.88 | -3.14 | 690.6395 | 690.6376 | 672.6232, 300.2876, 282.2766, 264.2685, 252.2686, 60.0444 |
| 239 | Cer (d19:2/16:1(OH)) | C35 H65 N O4 | 11.98 | 99.09 | -0.05 | 564.4986 | 564.4859 | 546.4859, 528.4769, 510.4669, 498.4673, 312.2901, 294.2786, 276.2685, 264.2686, 60.0444 |
| 240 | Cer (d19:2/25:2(OH)) | C44 H81 N O4 | 17.90 | 68.92 | -0.54 | 688.6238 | 688.6235 | 670.6304, 294.2822, 276.2681, 264.2685, 60.0444 |
| 241 | Cer (d19:3/16:1(OH)) | C35 H63 N O4 | 10.27 | 86.35 | -1.54 | 562.4830 | 562.4823 | 544.4573, 526.4616, 514.4674, 310.2741, 292.2638, 274.2525, 262.2538, 60.0444 |
| 242 | Cer (d20:1/26:2(OH)) | C46 H87 N O4 | 19.50 | 74.11 | -5.66 | 718.6708 | 718.6666 | 700.6493, 328.3003, 310.2958, 292.2999, 280.3026, 60.0442 |
| 243 | Cer (d20:1/28:2(OH)) | C48 H91 N O4 | 21.22 | 81.71 | -4.48 | 746.7021 | 746.6990 | 728.6982, 328.3194, 310.3141, 292.3000, 280.3083, 60.0444 |
| 244 | Cer (t18:1/16:0) | C34 H67 N O4 | 12.07 | 98.07 | -0.36 | 554.5143 | 554.5140 | 536.5034, 518.4917, 500.4812, 488.4821, 316.2846, 298.2742, 280.2623, 262.2526, 250.2160, 60.0438 |
| 245 | Cer (t18:1/16:1) | C34 H65 N O4 | 11.36 | 80.67 | 0.67 | 552.4986 | 552.4988 | 534.4856, 516.4770, 316.2805, 298.2729, 280.2632, 262.2532, 250.2522, 60.0438 |
| 246 | Cer (t18:1/17:0) | C35 H69 N O4 | 12.61 | 99.87 | 0.34 | 568.5299 | 568.5297 | 550.5129, 532.5038, 514.4871, 502.4912, 316.2853, 298.2738, 280.2637, 262.2534, 250.2529, 60.0444 |
| 247 | Cer (t18:1/18:0) | C36 H71 N O4 | 12.90 | 99.97 | -0.14 | 582.5456 | 582.5457 | 564.5339, 546.5239, 528.5136, 316.2842, 298.2728, 280.2628, 262.2524, 250.2521, 60.0439 |
| 248 | Cer (t18:1/18:1) | C36 H69 N O4 | 12.36 | 98.28 | -0.95 | 580.5299 | 580.5303 | 562.5187, 544.5075, 526.4959, 316.2841, 298.2731, 280.2626, 262.2523, 250.2522, 60.0439 |
| 249 | Cer (t18:1/18:2) | C36 H67 N O4 | 11.68 | 98.06 | -0.26 | 578.5143 | 578.5140 | 560.4973, 542.4909, 524.4842, 512.4776, 316.2846, 298.2739, 280.2634, 262.2533, 250.2535, 60.0445 |
| 250 | Cer (t18:1/18:2) isomer | C36 H67 N O4 | 12.50 | 70.64 | 2.72 | 578.5143 | 578.5128 | 560.4902, 542.4856, 524.4864, 316.2853, 298.2732, 280.2627, 262.2526, 250.2529, 60.0439 |
| 251 | Cer (t18:1/18:3) | C36 H65 N O4 | 12.05 | 96.31 | 1.76 | 576.4986 | 576.4976 | 558.4670, 522.4742, 316.2826, 298.2727, 280.2623, 262.2526, 250.2441, 60.0438 |
| 252 | Cer (t18:1/18:4) | C36 H63 N O4 | 12.25 | 84.80 | -2.39 | 574.483 | 574.4811 | 556.4733, 538.4963, 516.4954, 316.2598, 298.2548, 280.2441, 262.2545, 250.2498, 60.0444 |
| 253 | Cer (t18:1/18:5) | C36 H61 N O4 | 11.65 | 71.61 | -2.02 | 572.4673 | 572.4655 | 554.5043, 536.4954, 518.4802, 316.2662, 298.2726, 280.2635, 262.2536, 250.2538, 60.0444 |
| 254 | Cer (t18:1/19:0) | C37 H73 N O4 | 13.97 | 72.22 | 1.09 | 596.5612 | 596.5609 | 578.5503, 560.5393, 316.2833, 298.2719, 280.2616, 262.2507, 250.2536, 60.0438 |
| 255 | Cer (t18:1/20:0) | C38 H75 N O4 | 14.53 | 89.85 | 2.91 | 610.5769 | 610.5751 | 592.5653, 574.5535, 556.5479, 316.2853, 298.2732, 280.2626, 262.2534, 250.2535, 60.0439 |
| 256 | Cer (t18:1/20:3) | C38 H69 N O4 | 13.85 | 72.92 | -0.03 | 604.5299 | 604.5302 | 586.5114, 298.2549, 280.2431, 262.2524, 250.1978, 60.0438 |
| 257 | Cer (t18:1/21:0) | C39 H77 N O4 | 15.18 | 67.91 | 2.25 | 624.5925 | 624.5937 | 606.5834, 588.5681, 570.5621, 316.2832, 298.2738, 280.2632, 262.2539, 250.2529, 60.0445 |
| 258 | Cer (t18:1/22:0) | C40 H79 N O4 | 15.85 | 97.62 | 0.17 | 638.6082 | 638.6090 | 620.5952, 602.5859, 584.5758, 316.2848, 298.2741, 280.2635, 262.2532, 250.2532, 60.0445 |
| 259 | Cer (t18:1/22:2) | C40 H75 N O4 | 15.06 | 60.13 | 4.36 | 634.5769 | 634.5737 | 616.5468, 598.5342, 316.2847, 298.2728, 280.2610, 262.2511, 250.2529, 60.0438 |
| 260 | Cer (t18:1/22:3) | C40 H73 N O4 | 15.16 | 63.73 | -1.93 | 632.5612 | 632.5615 | 614.5742, 316.2800, 298.2719, 280.2616, 262.2519, 250.2531, 60.0438 |
| 261 | Cer (t18:1/22:4) | C40 H71 N O4 | 14.78 | 83.30 | -1.66 | 630.5456 | 630.5442 | 612.5304, 582.5223, 298.3091, 298.2719, 262.2531, 250.2537, 60.0445 |
| 262 | Cer (t18:1/23:0) | C41 H81 N O4 | 16.50 | 92.67 | 0.77 | 652.6238 | 652.642 | 634.6119, 616.6029, 598.5842, 316.2845, 298.2736, 280.2635, 262.2533, 250.2528, 60.0445 |
| 263 | Cer (t18:1/24:0) | C42 H83 N O4 | 17.22 | 99.65 | 0.15 | 666.6395 | 666.6397 | 648.6274, 630.6160, 612.6058, 600.6070, 316.2843, 298.2740, 280.2634, 262.2634, 250.2533, 60.0445 |
| 264 | Cer (t18:1/24:1) | C42 H81 N O4 | 16.02 | 69.30 | -5.37 | 664.6238 | 664.6203 | 646.6081, 628.6009, 610.5899, 316.2840, 298.2740, 280.2635, 262.2534, 250.2534, 60.0445 |
| 265 | Cer (t18:1/24:2) | C42 H79 N O4 | 16.38 | 85.64 | 1.95 | 662.6082 | 662.6066 | 644.5780, 626.5889, 316.2825, 298.2740, 280.2626, 262.2524, 250.2533, 60.0443 |
| 266 | Cer (t18:1/25:0) | C43 H85 N O4 | 17.92 | 89.09 | -1.61 | 680.6551 | 680.6538 | 662.6423, 644.6316, 626.6167, 316.2841, 298.2737, 280.2636, 262.2533, 250.2534, 60.0444 |
| 267 | Cer (t18:1/25:1) | C43 H83 N O4 | 16.75 | 70.78 | 1.09 | 678.6395 | 678.6358 | 660.6205, 642.6185, 316.2843, 298.2730, 280.2629, 262.2528, 250.2533, 60.0439 |
| 268 | Cer (t18:1/25:2) | C43 H81 N O4 | 17.03 | 62.43 | -0.21 | 676.6238 | 676.6210 | 658.6035, 298.2738, 280.2636, 262.252, 250.2522, 60.0444 |
| 269 | Cer (t18:1/28:2) | C46 H87 N O4 | 18.82 | 74.21 | -5.47 | 718.6708 | 718.6671 | 700.6501, 316.3009, 298.2650, 280.2623, 262.2535, 250.2530, 60.0446 |
| 270 | Cer (t19:1/18:2) | C37 H69 N O4 | 13.13 | 60.05 | 0.69 | 592.5299 | 592.5319 | 574.5200, 556.5060, 538.4960, 330.3001, 312.2902, 294.2776, 276.2682, 264.2690, 60.0444 |
| 271 | Cer (t19:1/18:4) | C37 H65 N O4 | 12.43 | 69.84 | 4.72 | 588.4986 | 588.5018 | 570.4809, 552.5144, 540.4658, 330.2678, 312.2711, 294.2750, 276.2686, 264.2686, 60.0444 |
| 272 | Cer (t19:1/24:3) | C43 H79 N O4 | 16.48 | 63.51 | 0.95 | 674.6082 | 674.6109 | 656.5833, 638.6259, 312.2902, 294.2796, 276.2683, 264.2689, 60.0444 |

TABLE 11-continued

524 SPLs identified including 275 new SPLs (bolded) from wild *Cordyceps* by using UHPLC-UHD iFunnel Q-TOF MS/MS

| No. | Name | Formula | RT | Score | Diff (ppm) | Theoretical [M + H]+ m/z | [M + H]+ m/z | MS/MS fragment m/z |
|---|---|---|---|---|---|---|---|---|
| 273 | Cer (t18:1/14:0(OH)) | C32 H63 N O5 | 10.75 | 84.32 | -4.34 | 542.4779 | 542.4758 | 524.4441, 506.4253, 298.2735, 262.2541, 250.2532, 60.0444 |
| 274 | Cer (t18:1/16:0(OH)) | C34 H67 N O5 | 11.60 | 98.64 | -0.48 | 570.5092 | 570.5090 | 552.5002, 534.4891, 516.4795, 498.4646, 316.2839, 280.2638, 262.2539, 250.2745 |
| 275 | Cer (t18:1/17:1(OH)) | C35 H67 N O5 | 10.71 | 69.44 | 2.17 | 582.5092 | 582.5083 | 564.4905, 546.4905, 528.4662, 510.4205, 280.2633, 262.2536, 250.2218, 60.0438 |
| 276 | Cer (t18:1/18:0(OH)) | C36 H61 N O5 | 12.68 | 93.94 | 0.01 | 598.5408 | 598.5408 | 580.5296, 562.5184, 544.5077, 526.4997, 316.2731, 298.2731, 280.2628, 262.2527, 250.2529, 60.0439 |
| 277 | Cer (t18:1/18:1(OH)) | C36 H69 N O5 | 11.93 | 80.41 | 1.31 | 596.5253 | 596.5253 | 578.5137, 560.5027, 542.4910, 524.4786, 316.2838, 298.2731, 280.2626, 262.2529, 250.2523, 60.0439 |
| 278 | Cer (t18:1/18:2(OH)) | C36 H67 N O5 | 11.31 | 76.49 | -0.25 | 594.5089 | 594.5089 | 576.4935, 558.4820, 540.5487, 316.2872, 298.2740, 280.2632, 262.2531, 250.2535, 60.0444 |
| 279 | Cer (t18:1/20:0(OH)) | C38 H75 N O5 | 13.95 | 98.20 | -0.72 | 626.5718 | 626.5714 | 608.5597, 590.5487, 572.5378, 554.5298, 316.2840, 298.2738, 262.2532, 250.2534, 60.0444 |
| 280 | Cer (t18:1/20:1(OH)) | C38 H73 N O5 | 12.91 | 81.77 | 3.62 | 624.5562 | 624.5544 | 606.5258, 588.5149, 570.5020, 558.4867, 316.2678, 298.2537, 280.2629, 262.2524, 250.2495, 60.0439 |
| 281 | Cer (t18:1/21:0(OH)) | C39 H77 N O5 | 14.60 | 95.50 | -1.21 | 640.5875 | 640.5867 | 622.5744, 604.5642, 586.5536, 568.5433, 316.2847, 298.2737, 280.2631, 262.2532, 250.2532, 60.0446 |
| 282 | Cer (t18:1/22:0(OH)) | C40 H79 N O5 | 15.27 | 99.54 | -0.08 | 654.6031 | 654.6029 | 636.5919, 618.5810, 600.5713, 582.5578, 316.2846, 298.2743, 280.2631, 262.2534, 250.2534, 60.0446 |
| 283 | Cer (t18:1/22:1(OH)) | C40 H77 N O5 | 14.20 | 75.26 | -3.01 | 652.5875 | 652.5872 | 634.5772, 616.5650, 598.5531, 580.5426, 316.2847, 298.2741, 280.2636, 262.2535, 250.2533, 60.0445 |
| 284 | Cer (t18:1/22:2(OH)) | C40 H75 N O5 | 13.31 | 79.69 | 2.01 | 650.5718 | 650.5719 | 632.5596, 614.5493, 596.5443, 578.5311, 316.2829, 298.2727, 280.2643, 262.2515, 250.2188, 60.0438 |
| 285 | Cer (t18:1/23:0(OH)) | C41 H81 N O5 | 15.93 | 98.18 | 0.04 | 668.6186 | 668.6186 | 650.6073, 632.5966, 614.5859, 596.5749, 316.2842, 298.2743, 280.2638, 262.2535, 250.2532, 60.0446 |
| 286 | Cer (t18:1/23:1(OH)) | C41 H79 N O5 | 14.82 | 99.57 | 0.34 | 666.6031 | 666.6034 | 648.5920, 630.5808, 612.5697, 594.5572, 316.2837, 298.2740, 280.2740, 280.2635, 250.253, 60.0445 |
| 287 | Cer (t18:1/24:0(OH)) | C42 H83 N O5 | 16.37 | 98.79 | -0.04 | 682.6344 | 682.6344 | 664.6237, 646.6129, 628.6019, 610.5907, 316.2845, 298.2748, 280.2642, 262.2537, 250.2535, 60.0445 |
| 288 | Cer (t18:1/24:1(OH)) | C42 H81 N O5 | 15.45 | 75.04 | -6.75 | 680.6188 | 680.6139 | 662.6078, 644.5969, 626.5858, 608.5744, 316.2844, 298.2744, 280.2640, 262.2538, 250.2533, 60.0446 |
| 289 | Cer (t18:1/24:2(OH)) | C42 H79 N O5 | 15.76 | 70.31 | -1.28 | 678.6031 | 678.6025 | 660.5742, 642.5699, 316.2881, 298.2753, 280.2623, 262.2536, 250.2531, 60.0445 |
| 290 | Cer (t18:1/25:0(OH)) | C43 H85 N O5 | 17.28 | 99.74 | -0.16 | 696.6501 | 696.6498 | 678.6384, 660.6277, 642.6169, 624.6067, 316.2839, 298.2742, 280.2637, 262.2637, 250.2531, 60.0445 |
| 291 | Cer (t18:1/25:1(OH)) | C43 H83 N O5 | 16.10 | 90.26 | -3.91 | 694.6344 | 694.6318 | 676.6216, 658.6117, 640.6023, 622.5935, 610.5932, 316.2849, 298.2743, 280.2636, 262.2636, 250.2531, 60.0445 |
| 292 | Cer (t18:1/25:2(OH)) | C43 H81 N O5 | 16.41 | 79.78 | 0.90 | 692.6188 | 692.6172 | 674.6149, 316.2841, 298.2736, 280.2631, 262.2531, 250.2528, 60.0444 |
| 293 | Cer (t18:1/26:0(OH)) | C44 H87 N O5 | 17.97 | 94.21 | 0.28 | 710.6657 | 710.6655 | 692.6539, 674.6427, 656.6334, 638.6195, 316.2841, 298.2740, 280.2634, 262.2535, 250.2534, 60.0445 |
| 294 | Cer (t18:1/26:1(OH)) | C42 H83 N O5 | 16.70 | 91.89 | -3.09 | 682.6363 | 682.6363 | 316.2832, 298.2739, 280.2632, 262.2535, 250.2535, 60.0445 |
| 295 | Cer (t19:1/16:0(OH)) | C35 H69 N O5 | 12.38 | 73.27 | -2.15 | 584.5249 | 584.5251 | 566.5127, 548.5035, 530.4901, 512.4839, 330.3000, 316.2896, 312.2898, 294.2784, 276.2682, 264.2679, 60.0444 |
| 296 | Cer (t19:1/18:0(OH)) | C37 H73 N O5 | 13.62 | 98.14 | -0.08 | 612.5562 | 612.5563 | 594.5453, 576.5334, 558.5239, 540.5070, 330.2995, 312.2896, 294.2788, 276.2685, 264.2682, 60.0444 |
| 297 | Cer (t14:1/25:5(tOH)) | C39 H67 N O7 | 13.47 | 96.18 | 1.13 | 662.4990 | 662.5003 | 644.4842, 206.1907, 194.1889, 60.0444 |
| 298 | Cer (t14:1/22:1(tOH)) | C36 H69 N O7 | 13.52 | 93.45 | -0.88 | 628.5147 | 628.5139 | 610.5070, 592.4891, 224.1960, 206.1904, 194.1867, 60.0446 |
| 299 | Cer (t18:1/23:5(tOH)) | C41 H71 N O7 | 15.62 | 96.85 | 1.61 | 690.5354 | 690.5315 | 672.5053, 654.5093, 298.2734, 280.2632, 262.2542, 250.2532, 60.0445 |
| 300 | Cer (t20:1/33:5(tOH)) | C53 H95 N O7 | 20.40 | 84.46 | -0.20 | 858.7181 | 858.7198 | 840.6983, 328.3243, 310.3140, 292.3008, 280.2970, 60.0444 |
| 301 | Cer (t14:0/35:1(dOH)) | C51 H101 N O5 | 17.57 | 88.25 | -2.28 | 808.7753 | 808.7726 | 790.7624, 772.7514, 754.7339, 742.6503, 292.3002, 274.2732, 256.2636, 238.2538, 226.2518, 60.0444 |
| 302 | Cer (t14:1/16:1(dOH)) | C30 H57 N O6 | 10.45 | 88.75 | -4.41 | 528.4259 | 528.4237 | 510.4075, 492.3745, 224.2012, 206.1906, 194.1910, 60.0444 |
| 303 | Cer (t14:1/16:0(dOH)) | C30 H59 N O6 | 10.52 | 78.15 | -7.13 | 530.4415 | 530.4378 | 512.4034, 242.2020, 224.2008, 206.1906, 194.1910, 60.0444 |
| 304 | Cer (t14:1/22:1(dOH)) | C36 H69 N O6 | 14.23 | 89.45 | -2.04 | 612.5198 | 612.5184 | 594.4955, 206.1907, 60.0444 |
| 305 | Cer (t14:1/24:3(dOH)) | C38 H69 N O6 | 12.25 | 79.78 | 4.05 | 636.5198 | 636.5215 | 618.5123, 600.4934, 224.1984, 206.1905, 206.1908, 194.1917, 60.0445 |
| 306 | Cer (t14:1/25:3(dOH)) | C39 H71 N O6 | 12.40 | 85.88 | 4.23 | 650.5354 | 650.5378 | 632.4836, 614.5106, 596.4895, 206.1908, 194.1917, 60.0444 |
| 307 | Cer (t14:1/26:0(dOH)) | C40 H79 N O6 | 13.18 | 85.82 | 1.13 | 670.5980 | 670.5986 | 652.5095, 224.2007, 206.1906, 60.0442 |
| 308 | Cer (t18:0/23:4(dOH)) | C41 H75 N O6 | 12.68 | 75.74 | -1.98 | 678.5667 | 678.564 | 660.5306, 642.5226, 624.5197, 606.5229, 588.5120, 282.2790, 264.2688, 252.2674, 60.0446 |
| 309 | Cer (t18:1/24:1(dOH)) | C60 H117 N O6 | 25.19 | 93.66 | -2.24 | 948.8954 | 948.8931 | 930.8809, 912.8630, 894.8682, 318.3006, 300.2897, 282.2790, 264.2683, 252.2694, 60.0445 |
| 310 | Cer (t18:1/24:0(dOH)) | C42 H83 N O6 | 15.20 | 89.04 | -0.56 | 698.6293 | 698.6294 | 680.6160, 662.6006, 644.5878, 626.5221, 298.2730, 280.2628, 262.2537, 250.2530, 60.0444 |
| 311 | Cer (t18:1/29:2(dOH)) | C47 H89 N O6 | 17.30 | 84.29 | 1.08 | 764.6763 | 764.6775 | 746.6444, 728.6761, 298.2732, 280.2635, 262.2518, 250.2518, 60.0443 |
| 312 | Cer (t18:1/42:1(dOH)) | C60 H115 N O6 | 24.50 | 84.68 | -2.25 | 946.8797 | 946.8772 | 928.8625, 910.8667, 316.2841, 198.1740, 280.2623, 262.2525, 250.2535, 60.0444 |
| 313 | Cer (d18:1/16:1) | C34 H63 N O3 | 12.25 | 97.16 | 0.17 | 534.4881 | 534.4880 | 280.2631, 262.2531, 250.2532, 60.0445 |
| 314 | Cer (d18:2/16:2) | C34 H61 N O3 | 11.65 | 71.45 | 0.24 | 532.4724 | 532.4732 | 514.4609, 496.4503, 484.4485, 298.2506, 280.2633, 262.2533, 250.2530, 60.0444 |
| 315 | Cer (d18:2/16:3) | C34 H59 N O3 | 11.61 | 63.60 | 3.70 | 530.4568 | 530.4543 | 298.2545, 280.2631, 262.2532, 250.2530, 60.0444 |
| 316 | Cer (d18:2/18:2) | C36 H65 N O3 | 13.25 | 70.68 | -3.52 | 560.5037 | 560.5033 | 298.4927, 524.4891, 524.4891, 280.2626, 262.2525, 250.2527, 60.0438 |

TABLE 11-continued

524 SPLs identified including 275 new SPLs (bolded) from wild *Cordyceps* by using UHPLC-UHD iFunnel Q-TOF MS/MS

| No. | Name | Formula | RT | Score | Diff (ppm) | Theoretical [M + H]⁺ m/z | [M + H]⁺ m/z | MS/MS fragment m/z |
|---|---|---|---|---|---|---|---|---|
| 317 | Cer (d18:2/18:3) | C36 H63 N O3 | 12.82 | 88.60 | −3.35 | 558.4881 | 558.4860 | 540.4748, 280.2629, 262.2538, 250.2534, 60.0445 |
| 318 | Cer (d18:2/18:4) | C36 H61 N O3 | 11.86 | 80.97 | 4.51 | 556.4724 | 556.4700 | 538.4693, 298.2719, 280.2615, 262.2525, 60.0439 |
| 319 | Cer (d18:2/20:4) | C38 H65 N O3 | 13.00 | 69.46 | 7.36 | 584.5037 | 584.4994 | 566.4892, 262.2528, 250.1914, 60.0438 |
| 320 | Cer (d18:2/20:5) | C38 H63 N O3 | 12.18 | 70.99 | 1.35 | 582.4878 | 582.4870 | 564.5255, 546.5137, 298.2728, 280.2620, 262.2522, 250.2531, 60.0438 |
| 321 | Cer (d18:2/21:6) | C39 H63 N O3 | 11.90 | 67.85 | 2.25 | 594.4881 | 594.4871 | 576.4931, 298.2737, 280.2622, 262.2519, 250.2525, 60.0438 |
| 322 | Cer (d18:2/22:2) | C40 H73 N O3 | 16.05 | 62.40 | 0.06 | 616.5636 | 616.5636 | 598.5538, 568.5054, 298.2556, 280.2603, 262.2536, 250.2544, 60.0445 |
| 323 | Cer (d18:2/22:3) | C40 H71 N O3 | 15.32 | 80.34 | −4.22 | 614.5483 | 614.5507 | 596.5360, 566.5336, 280.2640, 262.2526, 250.2562, 60.0443 |
| 324 | Cer (d18:2/22:5) | C40 H67 N O3 | 11.61 | 81.34 | −3.89 | 610.522 | 610.5194 | 592.5096, 574.4995, 298.2544, 280.2623, 262.2520, 250.2536, 60.0438 |
| 325 | Cer (d18:2/23:2) | C41 H75 N O3 | 16.64 | 70.34 | 1.23 | 630.5814 | 630.5822 | 612.5974, 298.2717, 280.2628, 262.2519, 250.2534, 60.0437 |
| 326 | Cer (d18:2/23:3) | C41 H73 N O3 | 16.10 | 80.09 | 4.40 | 628.5636 | 628.5664 | 610.5100, 280.2624, 262.2528, 250.2525, 60.0444 |
| 327 | Cer (d18:2/23:5) | C41 H69 N O3 | 12.38 | 76.57 | −4.00 | 624.535 | 624.5379 | 606.5288, 588.5229, 280.2615, 262.2545, 250.2152, 60.4380 |
| 328 | Cer (d18:2/23:5) isomer | C41 H69 N O3 | 12.68 | 76.00 | −4.83 | 624.535 | 624.5385 | 606.5261, 588.5153, 576.5145, 298.2668, 262.2523, 250.2523, 250.2538, 60.0438 |
| 329 | Cer (d18:2/23:6) | C41 H67 N O3 | 11.88 | 74.18 | −5.81 | 622.5194 | 622.5232 | 604.5097, 586.4975, 298.2719, 280.2618, 262.2653, 250.2506, 60.0438 |
| 330 | Cer (d24:2/) | C42 H77 N O3 | 17.28 | 62.12 | 0.47 | 644.5976 | 644.5946 | 626.5802, 298.2727, 280.2618, 262.2527, 250.2538, 60.0445 |
| 331 | Cer (d18:2/24:3) | C42 H75 N O3 | 16.76 | 71.64 | 4.65 | 642.5820 | 642.5793 | 624.5718, 606.6093, 280.2631, 262.2526, 250.2534, 60.0441 |
| 332 | Cer (d18:2/24:5) | C42 H71 N O3 | 12.68 | 75.36 | −3.74 | 638.5507 | 638.5537 | 620.5418, 602.5312, 298.2736, 298.2616, 262.2525, 250.2528, 60.0439 |
| 333 | Cer (d18:2/25:4) | C43 H75 N O3 | 14.46 | 71.55 | −0.76 | 654.582 | 654.5842 | 636.5842, 618.5721, 298.2722, 280.2616, 262.2542, 60.0438 |
| 334 | Cer (d18:2/25:5) | C44 H73 N O3 | 13.91 | 66.86 | −3.43 | 652.5663 | 652.5705 | 634.5584, 616.5488, 280.2664, 262.2519, 250.2529, 60.0438 |
| 335 | Cer (d18:2/26:1) | C44 H83 N O3 | 19.29 | 81.79 | 3.66 | 674.6446 | 674.6417 | 280.2630, 262.2520, 250.2538, 60.0444 |
| 336 | Cer (d18:2/26:4) | C44 H75 N O3 | 12.65 | 84.76 | −2.07 | 666.582 | 666.5839 | 648.5699, 630.6019, 298.2825, 280.2615, 262.2528 |
| 337 | Cer (d18:2/26:4) isomer | C44 H75 N O3 | 13.91 | 84.28 | −3.52 | 666.582 | 666.5842 | 648.5761, 630.5651, 298.2521, 280.2613, 262.2519, 60.0437 |
| 338 | Cer (d18:2/27:5) | C45 H77 N O3 | 15.20 | 67.44 | −6.98 | 680.5976 | 680.6025 | 662.5883, 644.5798, 298.2722, 280.2623, 262.2522, 250.2533, 60.0438 |
| 339 | Cer (d18:2/27:6) | C45 H75 N O3 | 14.20 | 66.51 | −5.37 | 678.5849 | 678.5849 | 660.5730, 642.5627, 298.2722, 298.2736, 280.2631, 262.2525, 250.2154, 60.0439 |
| 340 | Cer (d18:2/28:5) | C46 H79 N O3 | 15.25 | 71.25 | −4.67 | 694.6133 | 694.6169 | 676.6053, 658.5963, 298.2730, 280.2736, 280.2616, 262.2616, 250.2528, 60.0438 |
| 341 | Cer (d18:2/29:5) | C47 H81 N O3 | 16.00 | 75.84 | −4.36 | 708.6289 | 708.6324 | 690.6200, 672.6090, 298.2621, 280.2757, 280.2621, 262.2616, 250.2538, 60.0438 |
| 342 | Cer (d18:2/29:6) | C47 H79 N O3 | 15.43 | 75.21 | −5.34 | 706.6133 | 706.6174 | 688.6041, 670.5932, 280.2622, 280.2622, 262.2523, 250.2517, 60.0438 |
| 343 | Cer (d18:2/32:5) | C50 H87 N O3 | 16.63 | 80.75 | −2.99 | 750.6759 | 750.6785 | 732.6651, 714.6544, 298.2742, 280.2615, 262.2526, 60.0437 |
| 344 | Cer (d18:2/32:6) | C50 H85 N O3 | 15.45 | 80.28 | −2.62 | 748.6602 | 748.6627 | 730.6497, 712.6394, 298.2758, 280.2614, 262.2520, 60.0435 |
| 345 | HexCer (d16:0/20:0) | C42 H83 N O8 | 13.78 | 82.30 | −3.99 | 730.6191 | 730.6173 | 568.5657, 550.5537, 532.5384, 274.2764, 238.2504 |
| 346 | HexCer (d14:1/20:1) | C40 H77 N O8 | 12.23 | 82.05 | −0.80 | 700.5722 | 700.5733 | 682.5608, 664.5436, 538.5210, 520.5076, 502.4982, 490.4893, 226.2179, 208.2061, 196.2063, 60.0445 |
| 347 | HexCer (d14:1/20:1) | C40 H75 N O8 | 11.66 | 80.78 | 0.56 | 698.5565 | 698.5570 | 680.4985, 536.5011, 518.4918, 500.4774, 226.2159, 208.2064, 196.2065, 60.0442 |
| 348 | HexCer (d14:1/20:0) | C42 H81 N O8 | 13.39 | 83.31 | −3.57 | 728.6008 | 728.6035 | 710.5921, 692.5776, 566.5464, 548.5397, 530.5278, 226.2155, 208.2063, 196.2071 |
| 349 | HexCer (d14:1/22:1) | C42 H79 N O8 | 13.07 | 89.12 | −2.04 | 726.5878 | 726.5868 | 708.5369, 564.5222, 546.5222, 534.5254, 528.4775, 226.2150, 208.2064, 196.2066, 60.0445 |
| 350 | HexCer (d14:2/20:1) | C40 H73 N O8 | 11.51 | 70.67 | −0.65 | 696.5407 | 696.5407 | 678.5317, 534.4861, 516.4769, 498.4646, 242.2475, 224.2013, 206.1907, 194.1898, 60.0444 |
| 351 | HexCer (d14:2/22:1) | C42 H77 N O8 | 12.45 | 93.86 | 2.18 | 724.5722 | 724.5738 | 562.5194, 544.5097, 224.2012, 206.1906, 194.1903, 60.0448 |
| 352 | HexCer (d14:2/23:1) | C43 H79 N O8 | 13.18 | 80.54 | 2.35 | 738.5878 | 738.5868 | 576.5356, 558.523, 206.1909, 60.0445 |
| 353 | HexCer (d14:2/24:1) | C44 H81 N O8 | 13.64 | 77.56 | −1.67 | 752.6015 | 752.6035 | 710.5920, 590.5407, 572.5334, 224.2033, 254.2468, 236.2367, 224.2384 |
| 354 | HexCer (d16:1/20:0) | C44 H81 N O8 | 13.26 | 76.45 | 3.56 | 728.6023 | 728.6035 | 708.5822, 564.5342, 546.5233, 528.5157, 254.2460, 236.2371, 224.2382, 60.0445 |
| 355 | HexCer (d16:1/20:1) | C42 H79 N O8 | 12.92 | 78.09 | 2.80 | 726.5868 | 726.5868 | 708.5822, 564.5342, 546.5233, 528.5157, 254.2460, 236.2371, 224.2382, 60.0445 |
| 356 | HexCer (d16:2/20:1) | C42 H77 N O8 | 12.53 | 80.67 | 1.67 | 724.5722 | 724.5716 | 706.5766, 544.5088, 532.5085, 526.5054, 234.2216, 222.2269, 60.0444 |
| 357 | HexCer (d16:2/22:1) | C44 H81 N O8 | 13.70 | 96.62 | 0.70 | 752.6035 | 752.6042 | 734.5937, 590.5480, 572.5391, 560.5364, 252.2295, 234.2214, 60.0446 |
| 358 | HexCer (d18:1/16:0) | C40 H77 N O8 | 12.17 | 80.87 | −0.05 | 700.5722 | 700.5711 | 682.5674, 520.5051, 502.4979, 490.4942, 282.2790, 264.2685, 252.2677, 60.0445 |
| 359 | HexCer (d18:2/16:0) | C40 H75 N O8 | 11.66 | 96.87 | 0.07 | 698.5569 | 698.5569 | 680.5451, 536.4983, 518.4929, 500.4820, 488.4819, 280.2634, 262.2536, 250.2532, 60.0446 |
| 360 | HexCer (d18:2/16:1) | C40 H73 N O8 | 11.38 | 83.13 | −3.01 | 696.5385 | 696.5385 | 678.5227, 534.4875, 516.4767, 504.4772, 498.4617, 280.2639, 262.2535, 250.2532, 60.0446 |
| 361 | HexCer (d18:2/24:1) | C48 H89 N O8 | 16.11 | 87.98 | −3.34 | 808.6661 | 808.6632 | 790.5420, 646.6109, 628.6012, 280.2616, 262.2507, 250.2531 |

TABLE 11-continued

524 SPLs identified including 275 new SPLs (bolded) from wild *Cordyceps* by using UHPLC-UHD iFunnel Q-TOF MS/MS

| No. | Name | Formula | RT | Score | Diff (ppm) | Theoretical [M + H]+ m/z | [M + H]+ m/z | MS/MS fragment m/z |
|---|---|---|---|---|---|---|---|---|
| 362 | HexCer (d19:2/16:0) | C41 H77 N O8 | 11.98 | 97.44 | −0.29 | 712.5722 | 712.5721 | 694.5606, 550.5427, 532.5072, 514.4975, 502.4963, 352.3203, 334.3071, 294.2787, 276.2684, 264.2679, 60.0444 |
| 363 | HexCer (d19:2/18:1) | C43 H79 N O8 | 12.54 | 96.41 | 1.07 | 738.5878 | 738.5890 | 720.5697, 576.5332, 558.5228, 546.5198, 540.5313, 312.2896, 294.2786, 276.2684, 264.2679, 60.0441 |
| 364 | HexCer (d19:2/18:2) | C43 H77 N O8 | 12.28 | 98.46 | −0.70 | 736.5722 | 736.5718 | 718.5645, 574.5181, 556.5074, 538.4971, 526.4960, 294.2792, 276.2684, 264.268, 60.0446 |
| 365 | HexCer (d19:2/24:1) | C49 H91 N O8 | 16.24 | 96.04 | −1.53 | 822.6817 | 822.6809 | 660.6272, 642.6167, 630.6187, 294.2768, 276.2681, 264.2620, 60.0446 |
| 366 | HexCer (d19:3/16:0) | C41 H75 N O8 | 10.25 | 77.37 | −4.29 | 710.5565 | 710.5546 | 692.5443, 548.5000, 530.4913, 512.4820, 310.2715, 292.2629, 274.2538, 262.2495, 60.0445 |
| 367 | HexCer (d14:1/22:0(OH)) | C42 H81 N O9 | 13.16 | 96.64 | −0.30 | 744.5984 | 744.5985 | 726.5847, 564.5321, 546.5212, 534.5353, 526.5212, 226.2169, 208.2062, 196.2067, 60.0441 |
| 368 | HexCer (d16:1/20:0(OH)) | C42 H81 N O9 | 13.01 | 80.87 | −3.45 | 744.5984 | 744.5970 | 726.5842, 564.5338, 546.5227, 534.5226, 528.5104, 254.2447, 236.2368, 224.2379, 60.0444 |
| 369 | HexCer (d16:1/22:0(OH)) | C44 H85 N O9 | 13.98 | 89.55 | −2.41 | 772.6297 | 772.6290 | 754.6134, 592.5647, 574.5525, 562.5538, 254.2461, 236.2365, 224.2378, 60.0443 |
| 370 | HexCer (d16:1/22:3(OH)) | C44 H79 N O9 | 12.90 | 87.5 | −3.93 | 766.5828 | 766.5797 | 748.5944, 604.5479, 586.5357, 254.2475, 236.2365, 224.2430, 60.0445 |
| 371 | HexCer (d16:1/23:4(OH)) | C45 H79 N O9 | 13.29 | 86.78 | −4.32 | 778.5828 | 778.5806 | 760.5765, 616.5275, 598.5212, 254.2500, 236.2363, 224.1961 |
| 372 | HexCer (d16:2/22:3(OH)) | C44 H77 N O9 | 12.51 | 93.67 | 1.58 | 764.5671 | 764.5681 | 746.5606, 602.5221, 584.5130, 252.2246, 234.2210, 222.2234, 60.0445 |
| 373 | HexCer (d16:2/24:3(OH)) | C46 H81 N O9 | 13.73 | 87.46 | −4.29 | 792.5984 | 792.5949 | 774.6076, 630.5431, 612.5243, 594.5556, 252.2358, 234.2214, 60.0439 |
| 374 | HexCer (d18:2/15:1(OH)) | C39 H71 N O9 | 10.66 | 82.07 | −1.26 | 698.5202 | 698.5185 | 680.5060, 518.4526, 500.4441, 488.4421, 482.4338, 470.4337, 280.2637, 262.2533, 250.2530 |
| 375 | HexCer (d18:2/16:1(OH)) | C40 H73 N O9 | 11.03 | 98.18 | −0.21 | 712.5358 | 712.5358 | 694.5237, 676.5147, 658.5090, 628.4878, 550.3294, 532.4718, 514.4613, 502.4604, 496.4503, 484.4502, 348.2893, 330.2793, 318.2781, 280.2632, 262.2534, 250.2531, 60.0445 |
| 376 | HexCer (d18:2/24:0(OH)) | C48 H91 N O9 | 16.11 | 89.41 | −0.81 | 826.6767 | 826.6749 | 808.6616, 646.6104, 628.6013, 616.4943, 280.2639, 262.2540, 250.2532, 60.0444 |
| 377 | HexCer (d19:2/16:0(OH)) | C41 H77 N O9 | 11.66 | 97.81 | −0.33 | 528.5671 | 528.5670 | 710.5554, 692.5369, 566.5116, 548.5028, 530.4924, 518.4912, 512.4760, 368.3158, 350.305, 338.3050, 294.2779, 276.2685, 264.2663, 60.0445 |
| 378 | HexCer (d19:2/16:1(OH)) | C41 H75 N O9 | 10.90 | 96.97 | −0.59 | 726.5515 | 726.5512 | 708.5381, 690.5310, 672.5060, 564.4936, 546.4868, 528.4763, 516.4755, 510.4657, 498.4657, 366.2989, 348.2896, 330.2800, 294.2792, 276.2685, 264.2688, 60.0444 |
| 379 | HexCer (d19:2/16:1(OH)) Isomer | C41 H75 N O9 | 11.31 | 99.37 | 0.19 | 726.5515 | 726.5515 | 708.5403, 690.5291, 678.5261, 660.5179, 654.5106, 564.5011, 546.488, 528.4775, 516.4765, 510.4669, 498.4661, 366.3000, 348.2899, 330.2794, 312.2906, 294.2789, 276.2689, 264.2686, 60.0444 |
| 380 | HexCer (d19:2/17:0(OH)) | C42 H79 N O9 | 12.05 | 99.50 | 0.71 | 742.5828 | 742.5833 | 724.5694, 706.5595, 580.5255, 562.5169, 544.5066, 532.5063, 312.2908, 294.2786, 276.268, 264.2664, 286.2726, 268.2624, 60.0443 |
| 381 | HexCer (d19:2/17:1(OH)) | C42 H77 N O9 | 11.62 | 94.99 | 2.28 | 740.5671 | 740.5691 | 722.5555, 704.5431, 560.5010, 542.4941, 524.4816, 512.4827, 294.2781, 276.2688, 264.2661, 60.0451 |
| 382 | HexCer (d19:2/17:3(OH)) | C42 H73 N O9 | 11.53 | 94.43 | −0.59 | 736.5358 | 736.5354 | 718.5402, 700.5376, 574.4999, 556.4960, 548.5025, 530.4925, 542.4941, 524.4816, 512.4827, 530.4925, 546.5222, 540.5139, 294.2782, 276.2680, 300.2890, 264.2676, 60.0444 |
| 383 | HexCer (d19:2/18:0(OH)) | C43 H81 N O9 | 12.73 | 95.49 | −0.47 | 756.5984 | 756.5986 | 738.5860, 720.5687, 594.5412, 576.5332, 558.5229, 546.5222, 540.5139, 294.2782, 276.2680, 300.2890, 282.2782, 60.0441 |
| 384 | HexCer (d19:2/18:1(OH)) | C43 H79 N O9 | 12.28 | 96.12 | −1.02 | 754.5828 | 754.5822 | 736.5712, 718.5549, 700.5467, 688.5226, 574.5182, 556.5078, 544.5070, 538.4975, 526.4982, 394.3317, 376.3196, 358.3115, 294.2781, 276.2685, 264.2680, 60.0445 |
| 385 | HexCer (d19:2/18:3(OH)) | C43 H75 N O9 | 11.56 | 97.17 | 1.13 | 750.5515 | 750.5521 | 732.5364, 588.4946, 570.4868, 312.2699, 294.2792, 276.2687, 264.2685, 60.0444 |
| 386 | HexCer (d19:2/19:2(OH)) | C44 H79 N O9 | 13.11 | 76.89 | −1.24 | 766.5828 | 766.5804 | 748.5866, 604.5307, 586.5315, 294.2765, 276.2672, 264.2675 |

TABLE 11-continued

524 SPLs identified including 275 new SPLs (bolded) from wild *Cordyceps* by using UHPLC-UHD iFunnel Q-TOF MS/MS

| No. | Name | Formula | RT | Score | Diff (ppm) | Theoretical [M + H]+ m/z | [M + H]+ m/z | MS/MS fragment m/z |
|---|---|---|---|---|---|---|---|---|
| 387 | HexCer (d19:2/19:3(OH)) | C44 H77 N O9 | 12.72 | 70.89 | -5.09 | 764.5671 | 764.5658 | 746.5423, 602.5324, 584.5122, 294.2823, 276.2680, 264.2565, 60.0445 |
| 388 | HexCer (d19:2/22:0(OH)) | C47 H89 N O9 | 14.96 | 83.69 | -2.41 | 812.6610 | 812.6600 | 632.5846, 614.5880, 294.2777, 276.2674, 264.2673, 60.0438 |
| 389 | HexCer (d19:2/24:0(OH)) | C49 H93 N O9 | 16.25 | 98.08 | -0.05 | 840.6923 | 840.6927 | 822.7358, 660.6249, 642.6172, 630.6112, 294.2798, 276.2685, 264.2668, 60.0451 |
| 390 | HexCer (d19:2/24:1(OH)) | C49 H91 N O9 | 15.12 | 97.01 | -0.85 | 838.6767 | 838.6764 | 820.6400, 658.6090, 640.6045, 622.5984, 312.2910, 294.2793, 276.2683, 264.2698, 60.0443 |
| 391 | HexCer (d19:3/16:1(OH)) | C41 H73 N O9 | 9.97 | 96.66 | -1.28 | 724.5358 | 724.5350 | 706.5223, 688.5122, 670.5009, 562.4805, 544.4712 526.4603, 514.4595, 508.4498, 496.4508, 362.3034, 310.2737, 292.2640, 274.2534, 262.2535, 60.0445 |
| 392 | HexCer (t18:0/24:0(OH)) | C48 H95 N O10 | 16.11 | 74.18 | -2.49 | 846.7029 | 846.7011 | 828.6888, 684.6478, 666.6396, 648.6284, 630.6240, 318.2983, 300.2911, 282.2791, 264.2702, 252.2739, 60.0446 |
| 393 | HexCer (t18:1/20:1(OH)) | C44 H83 N O10 | 11.66 | 70.63 | -2.56 | 786.609 | 786.6084 | 624.5406, 606.5329, 588.5269, 316.2826, 298.2738, 280.2633, 262.2531, 250.2521, 60.0443 |
| 394 | HexCer (t18:1/23:0(OH)) | C47 H91 N O10 | 14.74 | 91.88 | -2.19 | 830.6716 | 830.6706 | 668.6172, 650.6049, 632.5968, 614.5852, 298.2741, 280.2625, 262.2525, 250.2495, 60.0447 |
| 395 | HexCer (t18:1/24:0(OH)) | C48 H93 N O10 | 15.34 | 96.31 | -0.09 | 844.6872 | 844.6877 | 682.6328, 664.6240, 646.6130, 628.5991, 616.5984, 598.8370, 316.2823, 298.2736, 280.2633, 262.2523, 250.2517, 60.0448 |
| 396 | HexCer (t18:1/25:0(OH)) | C49 H95 N O10 | 16.00 | 91.29 | -1.79 | 858.7029 | 858.7025 | 696.6554, 678.6375, 660.6270, 642.6041, 630.6169, 316.2742, 298.2713, 280.2623, 262.2519, 250.2542, 60.0448 |
| 397 | Hex-HexCer (t19:1/16:1(OH)) | C41 H77 N O10 | 10.62 | 82.53 | 4.40 | 744.5563 | 744.562 | 726.5492, 708.5463, 582.4988, 564.4956, 546.4857, 534.4859, 528.4751, 516.4728, 330.2735, 312.2527, 294.2783, 276.2675, 264.2691, 270.2406 |
| 398 | HexCer (t19:1/19:3(OH)) | C44 H79 N O10 | 11.96 | 83.54 | -2.99 | 782.5777 | 782.575 | 764.5646, 620.5213, 602.5090, 312.2706, 294.2789, 276.2683, 264.2669, 60.0441 |
| 399 | HexCer (t19:2/16:1(OH)) | C41 H75 N O10 | 10.15 | 87.01 | 2.07 | 742.5464 | 742.5479 | 562.4829, 544.4709, 526.4709, 514.4611, 508.4462, 310.2724, 292.2633, 274.2530, 262.2517, 60.0446 |
| 400 | Hex-HexCer (d14:1/20:0) | C46 H87 N O13 | 11.67 | 96.61 | 0.51 | 862.625 | 862.6259 | 844.6009, 682.5667, 520.5094, 502.4976, 490.4990, 226.2156, 208.2055, 196.205, 60.0444 |
| 401 | Hex-HexCer (d14:1/22:0) | C48 H91 N O13 | 12.78 | 82.54 | -0.78 | 890.6563 | 890.6559 | 872.6427, 710.5885, 566.5476, 548.5383, 530.5210, 518.5210, 226.2129, 208.2049, 196.1995 |
| 402 | Hex-HexCer (d14:2/20:0) | C46 H83 N O13 | 11.05 | 88.72 | 1.59 | 858.5937 | 858.5949 | 840.5751, 696.5213, 534.4829, 516.4777, 504.4723, 498.4522, 224.1983, 206.1897, 194.1897, 60.0445 |
| 403 | Hex-HexCer (d14:2/22:1) | C48 H87 N O13 | 11.98 | 87.65 | 2.01 | 886.625 | 886.6265 | 562.5191, 544.5093, 224.2002, 206.1906, 194.1855, 60.0448 |
| 404 | Hex-HexCer (d14:2/24:3) | C50 H87 N O13 | 12.07 | 87.72 | 1.26 | 910.625 | 910.6265 | 892.6176, 764.5613, 602.5299, 584.4987, 234.2207, 206.1910, 60.0442 |
| 405 | Hex-HexCer (d14:1/22:0(OH)) | C48 H91 N O14 | 12.23 | 75.77 | -4.60 | 906.6512 | 906.6483 | 888.6385, 744.5524, 726.5879, 708.4134, 582.4979, 564.5340, 546.5415, 534.5238, 528.5236, 226.2147, 208.2059, 196.2064 |
| 406 | Hex-HexCer (d14:1/22:0(OH)) isomer | C48 H91 N O14 | 12.40 | 96.18 | -0.11 | 906.6512 | 906.6511 | 888.6391, 726.5862, 708.5717, 564.5337, 546.5256, 534.5237, 516.5081, 226.2165, 208.2063, 196.2061, 60.0457 |
| 407 | Hex-HexCer (d14:1/22:2(OH)) | C48 H85 N O14 | 11.38 | 82.94 | 1.40 | 900.6043 | 900.6035 | 882.6098, 738.5406, 558.4816, 226.2170, 208.2060, 196.2062, 60.0445 |
| 408 | Hex-HexCer (d14:2/25:3(OH)) | C51 H89 N O14 | 12.50 | 70.85 | 0.20 | 940.6356 | 940.6353 | 922.6240, 778.5800, 564.5266, 546.5250, 528.5132, 206.1907, 60.0437 |
| 409 | Hex-HexCer (d16:2/22:3(OH)) | C50 H87 N O14 | 12.13 | 75.85 | -1.65 | 926.6199 | 926.6166 | 908.6121, 764.5756, 602.5319, 252.2311, 234.2222, 222.2224, 60.0443 |

TABLE 11-continued

524 SPLs identified including 275 new SPLs (bolded) from wild *Cordyceps* by using UHPLC-UHD iFunnel Q-TOF MS/MS

| No. | Name | Formula | RT | Score | Diff (ppm) | Theoretical [M + H]+ m/z | [M + H]+ m/z | MS/MS fragment m/z |
|---|---|---|---|---|---|---|---|---|
| 410 | Hex-HexCer (t18:0/22:0(OH)) | C52 H101 N O15 | 13.75 | 77.36 | −2.86 | 980.7244 | 980.7222 | 962.7456, 800.6400, 656.6186, 638.6056, 620.5979, 602.5951, 590.5832, 300.2874, 282.2820, 264.2654, 252.2622, 60.0437 |
| 411 | Hex-HexCer (t18:0/24:0(OH)) | C54 H105 N O15 | 14.96 | 93.69 | −1.44 | 1008.7557 | 1008.7546 | 990.6811, 684.6489, 666.6379, 648.6313, 630.6152, 618.4686, 612.6008, 300.2853, 282.2794, 264.2704, 252.2678, 60.0447 |
| 412 | Hex-HexCer (t18:1/9:2(OH)) | C39 H69 N O15 | 11.05 | 76.1076 | 2.70 | 792.474 | 792.4762 | 774.5375, 630.5020, 468.4545, 262.2538 |
| 413 | Hex-HexCer (t18:1/22:0(OH)) | C52 H99 N O15 | 13.28 | 92.74 | −1.25 | 978.7087 | 978.7074 | 654.6025, 635.5882, 618.5809, 600.5689, 298.2776, 280.2603, 262.2516, 60.0441 |
| 414 | Hex-HexCer (t18:1/23:0(OH)) | C53 H101 N O15 | 13.88 | 85.89 | −1.19 | 992.7244 | 992.7229 | 974.7641, 956.6681, 812.6610, 668.6152, 650.6041, 632.5888, 614.5982, 602.5864, 298.2708, 280.2625, 262.2502, 250.2590, 60.0448 |
| 415 | Hex-HexCer (t18:1/24:0(OH)) | C54 H103 N O15 | 14.46 | 97.54 | −0.31 | 1006.74 | 1006.7402 | 988.7209, 826.6763, 682.6332, 664.6219, 646.6113, 628.6008, 616.6028, 316.2844, 298.2737, 280.2630, 262.2531, 250.2555, 60.0449 |
| 416 | Hex-HexCer (d18:2/18:3(OH)) | C48 H83 N O14 | 11.18 | 81.05 | −3.5 | 898.5886 | 898.5864 | 880.5949, 736.5459, 574.4968, 280.2660, 262.2524 |
| 417 | Hex-HexCer (d19:2/16:2) | C47 H83 N O13 | 10.86 | 77.85 | −2.14 | 870.5937 | 870.5915 | 852.5797, 708.5382, 690.5080, 546.4856, 528.4764, 510.4648, 498.4648, 294.2795, 276.2681, 264.2677, 60.0445 |
| 418 | Hex-HexCer (d19:2117:3) | C48 H83 N O13 | 11.21 | 86.48 | −2.96 | 882.5937 | 882.5914 | 864.5597, 720.5355, 558.4887, 294.2821, 276.2684, 60.0445 |
| 419 | Fuc-Fuc-Hex-Cer (d14:0/20:0(OH)) | C52 H99 N O17 | 11.75 | 85.16 | −3.85 | 1010.6986 | 1010.6953 | 992.6791, 846.6128, 700.5829, 538.5126, 520.5056, 2246.2436, 28.2319, 210.2207, 60.0447 |
| 420 | Fuc-Fuc-Hex-Cer (d14:1/22:4(OH)) | C54 H93 N O17 | 11.13 | 81.80 | −4.2 | 1028.6516 | 1028.6473 | 1010.6122, 964.5420, 818.6550, 536.5010, 518.4898, 500.4779, 226.2139, 208.2061, 196.2023 |
| 421 | Hex-Fuc-Hex-Cer (d14:2/22:1) | C54 H97 N O17 | 11.70 | 98.45 | 0.2 | 1032.6829 | 1032.6827 | 870.5406, 724.5298, 562.5184, 544.5095, 206.1894, 60.0449 |
| 422 | Fuc-Hex-Hex-Cer (d15:1/20:0(OH)) | C53 H99 N O18 | 11.58 | 90.59 | −0.15 | 1038.6935 | 1038.6935 | 874.6170, 712.5750, 550.5166, 532.5048, 520.5048, 240.2313, 222.2216, 210.2221 |
| 423 | Fuc-Hex-Hex-Cer (d15:1/22:0(OH)) | C55 H103 N O18 | 12.61 | 92.27 | −1.58 | 1066.7248 | 1066.7237 | 1048.7392, 902.6456, 740.5990, 578.5485, 560.5386, 548.5395, 240.2286, 222.2229, 210.2215, 60.0452 |
| 424 | Fuc-Hex-Hex-Cer (d16:1/22:0(OH)) | C56 H105 N O18 | 13.13 | 79.71 | 1.49 | 1080.7404 | 1080.7398 | 1062.7203, 934.6807, 916.6671, 754.6068, 610.5769, 592.5637, 574.5594, 562.5517, 236.2369, 224.2310 |
| 425 | Hex-Hex-Fuc-Cer (d16:0/22:0) | C56 H107 N O17 | 13.73 | 88.19 | −2.48 | 1066.7612 | 1066.7586 | 1048.7774, 886.6259, 742.5848, 596.5944, 578.5851, 560.5721, 530.3641, 274.2782, 256.2621, 238.2466, 60.0453 |
| 426 | Fuc-Hex-Hex-Cer (d14:1/20:0) | C52 H97 N O17 | 11.38 | 96.30 | 0.52 | 1008.6829 | 1008.6829 | 990.6597, 862.6073, 844.6046, 682.5569, 538.5091, 520.5072, 502.4942, 490.4958, 226.2156, 208.2053, 196.2062, 60.0454 |
| 427 | Fuc-Hex-Hex-Cer (d14:1/21:0) | C53 H99 N O17 | 11.93 | 79.55 | −4.17 | 1022.6986 | 1022.6955 | 1004.6830, 858.6256, 696.5795, 552.5327, 534.5233, 516.5134, 226.2155, 208.2061, 60.0444 |
| 428 | Fuc-Hex-Hex-Cer (d14:1/22:0) | C52 H99 N O17 | 10.85 | 98.00 | 0.90 | 1004.6524 | 1004.6524 | 986.7199, 858.5710, 840.5663, 696.5508, 678.5270, 534.4866, 516.4767, 504.4753, 498.4600, 224.1998, 206.1900, 194.1896, 60.0447 |
| 429 | Fuc-Hex-Hex-Cer (d14:2/20:1) | C54 H101 N O17 | 12.31 | 98.28 | −0.35 | 1036.7142 | 1036.7143 | 1018.6920, 910.6186, 872.6417, 728.6090, 710.5876, 566.5492, 548.5406, 530.5288, 518.5278, 226.2164, 208.206, 196.2054, 60.0448 |
| 430 | Fuc-Hex-Hex-Cer (d14:1/23:0) | C55 H103 N O17 | 13.03 | 76.70 | −4.06 | 1050.7299 | 1050.7266 | 1032.7153, 886.6516, 724.6127, 580.5622, 562.5540, 544.5385, 226.2148, 208.2063, 196.2023 |
| 431 | Fuc-Hex-Hex-Cer (d14:1/24:2) | C56 H101 N O17 | 12.66 | 97.87 | −0.91 | 1060.7142 | 1060.7134 | 932.6493, 914.6412, 752.5832, 590.5351, 226.2082, 208.2053, 60.0438 |
| 432 | Fuc-Hex-Hex-Cer (d16:1/22:0) | C56 H105 N O17 | 13.34 | 96.33 | −1.55 | 1064.7455 | 1064.7441 | 1046.7819, 900.8091, 576.5727, 558.7031, 546.5535, 254.2054, 236.2402 |

TABLE 11-continued

524 SPLs identified including 275 new SPLs (bolded) from wild *Cordyceps* by using UHPLC-UHD iFunnel Q-TOF MS/MS

| No. | Name | RT | Score | Formula | Diff (ppm) | Theoretical [M + H]+ m/z | [M + H]+ m/z | MS/MS fragment m/z |
|---|---|---|---|---|---|---|---|---|
| 433 | Fuc-Hex-Hex-Cer (d16:2/22:2) | 12.31 | 88.63 | C56 H99 N O17 | −2.63 | 1058.6986 | 1058.6959 | 1040.6571, 912.6178, 750.5503, 254.2685, 234.2219, 222.2215, 60.044 |
| 434 | Fuc-Hex-Hex-Cer (d14:1/20:0(OH)) | 11.33 | 95.88 | C52 H97 N O18 | −2.02 | 1024.6778 | 1024.6759 | 1006.6625, 860.6067, 716.5607, 698.5565, 682.5586, 554.5134, 536.4947, 518.4947, 506.4917, 500.4761, 226.2179, 208.2060, 196.2069, 60.0443 |
| 435 | Fuc-Hex-Hex-Cer (d14:1/22:0(OH)) | 12.10 | 94.05 | C54 H101 N O18 | 0.40 | 1052.7091 | 1052.7083 | 1034.6939, 888.6392, 672.6548, 726.5795, 564.5314, 546.5219, 226.2193, 208.2065, 196.2013 |
| 436 | Fuc-Hex-Hex-Cer (d14:1/22:2(OH)) | 11.14 | 89.89 | C54 H95 N O18 | 1.32 | 1046.6622 | 1046.6638 | 1028.6500, 900.6001, 884.6106, 738.5492, 206.1889, 60.0445 |
| 437 | Fuc-Hex-Hex-Cer (d14:2/22:2(OH)) | 10.85 | 96.95 | C54 H93 N O18 | −0.56 | 1044.6465 | 1044.6456 | 1026.6255, 898.5811, 882.5874, 736.5322, 574.4720, 556.4727, 516.4746, 206.1887, 194.1865, 60.0452 |
| 438 | Fuc-Hex-Hex-Cer (d14:2/23:2(OH)) | 11.68 | 86.58 | C55 H97 N O18 | −3.20 | 1060.6778 | 1060.6745 | 1042.6775, 896.6269, 572.5286, 224.2378, 206.1902 |
| 439 | Fuc-Hex-Hex-Cer (d14:2/24:2(OH)) | 12.08 | 80.34 | C56 H99 N O18 | 3.99 | 1074.6935 | 1074.6987 | 1056.6810, 928.6270, 912.6354, 766.5776, 748.5652, 586.5067, 224.2046, 206.1881 |
| 440 | Fuc-Hex-Hex-Cer (d14:2/26:2(OH)) | 13.08 | 92.25 | C58 H103 N O18 | −1.43 | 1102.7248 | 1102.7235 | 1094.5206, 956.6560, 794.6100, 224.1969, 206.1903, 60.0437 |
| 441 | Fuc-Hex-Hex-Cer (d16:2/23:2(OH)) | 12.63 | 87.02 | C57 H101 N O18 | 0.74 | 1088.7091 | 1088.7090 | 1070.7042, 942.6406, 780.6034, 600.5573, 234.2230, 222.2176, 60.0439 |
| 442 | Fuc-Hex-Hex-Cer (d16:2/24:3(OH)) | 12.83 | 84.03 | C58 H101 N O18 | −3.97 | 1100.7091 | 1100.7048 | 954.6499, 792.5919, 234.2203 |
| 443 | Fuc-Hex-GalNAc-Cer (t14:1/22:0) | 12.31 | 89.92 | C56 H104 N2 O18 | −1.43 | 1093.7357 | 1093.7339 | 1075.7279, 929.6562, 767.5977, 564.5304, 546.5210, 528.5132, 224.1969, 206.1909 |
| 444 | Hex-Hex-Hex-Cer (t18:1/22:0(OH)) | 12.78 | 97.53 | C58 H109 N O20 | −0.82 | 1140.7612 | 1140.7602 | 1122.7736, 960.7059, 816.6430, 798.6366, 654.6012, 636.5895, 618.5802, 600.5672, 588.5734, 316.2856, 298.2717, 280.2631, 262.2524, 250.2536 |
| 445 | HexCer (d15:1/20:0(OH)) | 12.30 | 85.54 | C41 H79 N O9 | −4.16 | 730.5828 | 730.5799 | 712.5738, 568.5410, 550.5103, 532.5108, 520.5057, 240.2324, 222.2217, 210.2229, 60.0445 |
| 446 | Hex-HexCer (d14:1/20:0(OH)) | 11.40 | 91.64 | C46 H87 N O14 | 1.09 | 878.6199 | 878.6203 | 860.6228, 698.5590, 680.5396, 536.4992, 518.4907, 506.4896, 488.4824, 226.2154, 208.2054, 196.2062, 60.0439 |
| 447 | Fuc-Hex-HexCer (t18:1/24:1(OH)) | 13.42 | 84.71 | C54 H101 N O15 | −4.11 | 1004.7244 | 1004.7198 | 986.7189, 680.6189, 662.6025, 644.5919, 626.5755, 298.2669, 280.2640, 262.253, 60.0454 |
| 448 | SM (d14:0/18:0) | 11.53 | 96.35 | C37 H77 N2 O6 P | −1.47 | 677.5592 | 677.5586 | 210.2175, 184.0730, 86.0962, 60.0807 |
| 449 | SM (d14:0/20:0) | 12.63 | 96.58 | C39 H81 N2 O6 P | −0.47 | 705.5905 | 705.5906 | 210.2215, 184.0732, 86.0961, 60.0802 |
| 450 | SM (d14:1/18:0) | 11.18 | 96.34 | C37 H75 N2 O6 P | −0.60 | 675.5436 | 675.5433 | 657.5325, 598.4578, 208.2065, 184.0739, 166.0624, 124.9994, 104.1066, 86.0961, 60.0803 |
| 451 | SM (d14:1/19:0) | 11.66 | 96.51 | C38 H77 N2 O6 P | −1.12 | 689.5592 | 689.5585 | 671.5479, 612.4722, 208.2071, 184.0735, 166.0628, 124.9992, 104.1071, 86.0962, 60.0802 |
| 452 | SM (d14:1/20:0) | 12.21 | 99.35 | C39 H79 N2 O6 P | −0.33 | 703.5749 | 703.5745 | 685.5620, 626.4898, 502.4955, 208.2065, 184.0737, 166.0632, 124.9994, 104.1068, 86.0960, 60.0802 |
| 453 | SM (d14:1/21:0) | 12.77 | 96.28 | C40 H81 N2 O6 P | 0.23 | 717.5905 | 717.5904 | 699.5758, 208.2041, 184.0735, 166.0624, 124.9993, 104.1069, 86.0962, 60.0801 |
| 454 | SM (d14:1/22:0) | 13.39 | 98.82 | C41 H83 N2 O6 P | −0.38 | 731.6062 | 731.6058 | 713.5940, 654.5197, 530.5280, 208.2065, 184.0738, 166.0626, 124.9994, 104.1067, 86.0961, 60.0802 |
| 455 | SM (d14:1/23:0) | 14.06 | 96.09 | C42 H85 N2 O6 P | 0.40 | 745.6218 | 745.6217 | 727.6071, 208.2070, 184.0736, 166.0623, 124.9995, 104.1063, 86.0961, 60.0802 |
| 456 | SM (d14:1/24:0) | 14.66 | 94.71 | C43 H87 N2 O6 P | −1.06 | 759.6375 | 759.6369 | 741.6242, 682.5510, 208.2074, 184.0738, 166.0620, 124.9993, 104.1067, 86.0962, 60.0799 |
| 457 | SM (d14:1/26:0) | 15.81 | 97.20 | C45 H91 N2 O6 P | 1.52 | 787.6688 | 787.6675 | 769.6570, 208.2076, 184.0735, 166.0643, 124.9993, 104.1057, 86.0959, 60.0801 |
| 458 | SM (d14:2/19:0) | 11.28 | 95.04 | C38 H75 N2 O6 P | −1.56 | 687.5436 | 687.5424 | 669.5349, 206.1905, 184.0735, 166.0612, 124.9993, 104.1068, 86.0961, 60.0799 |
| 459 | SM (d14:2/22:0) | 12.91 | 98.67 | C41 H81 N2 O6 P | −0.22 | 729.5905 | 729.5902 | 711.5790, 652.5042, 528.5123, 206.1906, 184.0744, 166.0627, 124.9994, 104.1068, 86.0962, 60.0802 |
| 460 | SM (d14:2/24:0) | 11.78 | 99.16 | C39 H77 N2 O6 P | −0.31 | 701.5592 | 701.5588 | 683.5472, 624.4718, 518.4923, 500.4823, 206.1908, 184.0739, 166.0628, 124.9997, 104.1007, 86.0964, 60.0803 |

TABLE 11-continued

524 SPLs identified including 275 new SPLs (bolded) from wild *Cordyceps* by using UHPLC-UHD iFunnel Q-TOF MS/MS

| No. | Name | Formula | RT | Score | Diff (ppm) | Theoretical [M + H]+ m/z | [M + H]+ m/z | MS/MS fragment m/z |
|---|---|---|---|---|---|---|---|---|
| 461 | SM (d15:1/8:0) | C28 H57 N2 O6 P | 11.79 | 92.78 | −1.69 | 549.4027 | 549.4018 | 531.2622, 222.2238, 184.0736, 124.9991, 86.0961, 60.0802 |
| 462 | SM (d15:1/20:0) | C40 H81 N2 O6 P | 12.74 | 96.21 | −1.13 | 717.5905 | 717.5898 | 699.5794, 640.5017, 222.2224, 184.0737, 166.0622, 124.9995, 104.1067, 86.0961, 60.0804 |
| 463 | SM (d15:1/22:0) | C42 H85 N2 O6 P | 13.99 | 94.36 | −1.28 | 745.6218 | 745.6210 | 727.6112, 668.5373, 222.2228, 184.0735, 166.0611, 124.9992, 104.1069, 86.0961, 60.0801 |
| 464 | SM (d15:1/24:0) | C44 H89 N2 O6 P | 15.13 | 82.71 | −4.52 | 773.6531 | 773.6497 | 222.2229, 184.0734, 166.0641, 124.9994, 104.1072, 86.0962, 60.0803 |
| 465 | SM (d15:1/27:1) | C47 H93 N2 O6 P | 16.14 | 78.04 | −5.03 | 813.6844 | 813.6809 | 795.6454, 222.2282, 184.0734, 124.9983, 104.1085, 60.0796 |
| 466 | SM (d15:2/20:0) | C40 H79 N2 O6 P | 12.29 | 96.57 | −0.66 | 715.5749 | 715.5744 | 697.5612, 638.4946, 514.4958, 220.2065, 184.0737, 166.0632, 124.9993, 104.1066, 86.0961, 60.0804 |
| 467 | SM (d15:2/22:0) | C42 H83 N2 O6 P | 13.49 | 97.97 | −0.54 | 743.6062 | 743.6057 | 725.5920, 666.5250, 560.5360, 542.5265, 220.2062, 184.0737, 166.0621, 124.9994, 104.1068, 86.0960, 60.0800 |
| 468 | SM (d16:2/18:2) | C39 H73 N2 O6 P | 11.18 | 71.12 | −4.13 | 697.5279 | 697.5244 | 234.2217, 184.0736, 166.0636, 124.9993, 104.1072, 86.0960, 60.0804 |
| 469 | SM (d16:2/22:0) | C43 H85 N2 O6 P | 14.16 | 99.38 | −0.15 | 757.6218 | 757.6216 | 739.6090, 680.5386, 574.5523, 556.5438, 364.3575, 234.2220, 184.0738, 166.0630, 124.9994, 104.1067, 86.0961, 60.0803 |
| 470 | SM (d18:1/16:0) | C39 H79 N2 O6 P | 12.09 | 98.84 | −0.44 | 703.5750 | 703.5750 | 685.5629, 264.2693, 184.0738, 166.0630, 124.9994, 104.1068, 86.0962, 60.0803 |
| 471 | SM (d18:1/18:0) | C41 H83 N2 O6 P | 13.23 | 98.92 | −0.42 | 731.6063 | 731.6063 | 713.5932, 264.2692, 184.0739, 166.0630, 124.9995, 104.1071, 86.0962, 60.0803 |
| 472 | SM (d18:1/20:0) | C43 H87 N2 O6 P | 14.48 | 96.41 | −0.21 | 759.6375 | 759.6378 | 741.6273, 264.2680, 184.0735, 166.0634, 124.9994, 104.1069, 86.0961, 60.0803 |
| 473 | SM (d18:1/22:0) | C45 H91 N2 O6 P | 15.81 | 95.69 | −2.34 | 787.6688 | 787.6669 | 769.6570, 710.5799, 264.2709, 184.0735, 166.0643, 124.9993, 104.1057, 86.0959, 60.0801 |
| 474 | SM (d18:2/22:0) | C45 H89 N2 O6 P | 15.38 | 91.72 | −2.1 | 785.6531 | 785.6513 | 767.6394, 262.2491, 184.0735, 166.0643, 124.9989, 104.1069, 86.0960, 60.0803 |
| 475 | SM (d18:2/23:0) | C46 H91 N2 O6 P | 15.61 | 88.29 | −2.82 | 799.6688 | 799.6667 | 262.2545, 184.0725, 104.1050, 86.0957, 60.0801 |
| 476 | SM (d14:0/27:2(OH) Isomer | C46 H91 N2 O7 P | 14.54 | 89.19 | −2.31 | 815.6637 | 815.6617 | 797.6074, 210.2230, 184.0733, 125.0007, 104.1060, 86.0962, 60.0799 |
| 477 | SM (d14:1/21:0(OH) | C40 H81 N2 O7 P | 12.21 | 91.68 | −2.52 | 733.5854 | 733.5836 | 715.5720, 208.2060, 184.0734, 166.0627, 124.9992, 104.1066, 86.0961, 60.0800 |
| 478 | SM (d14:2/21:0(OH) | C40 H79 N2 O7 P | 11.81 | 70.65 | −0.49 | 731.5698 | 731.5683 | 206.1901, 184.0734, 166.0641, 124.9988, 104.1068, 86.0960, 60.0802 |
| 479 | SM (d14:2/22:0(OH) | C41 H81 N2 O7 P | 12.38 | 94.97 | −0.49 | 745.5854 | 745.5853 | 727.5724, 668.5010, 562.5217, 544.5085, 206.1909, 184.0737, 166.0624, 124.9994, 104.1067, 86.0961, 60.0803 |
| 480 | SM (d14:2/22:0(OH) Isomer | C41 H81 N2 O7 P | 12.03 | 93.23 | −1.89 | 745.5854 | 745.5843 | 727.5719, 668.5038, 562.5172, 544.5083, 206.1907, 184.0735, 124.9991, 104.1070, 86.0962, 60.0796 |
| 481 | SM (d16:2/22:0(OH) | C43 H85 N2 O7 P | 13.46 | 76.15 | −0.01 | 773.6167 | 773.6164 | 755.6037, 234.2220, 184.0735, 166.0628, 124.9997, 104.1067, 86.0962, 60.0803 |
| 482 | SM (d17:1/16:0(OH) | C38 H77 N2 O7 P | 11.18 | 92.94 | −2.66 | 705.5541 | 705.5525 | 687.5396, 250.2533, 184.0733, 124.9991, 86.0958 |
| 483 | SM (d18:1/16:0(OH) | C39 H79 N2 O7 P | 11.64 | 99.08 | −0.09 | 719.5698 | 719.5698 | 701.5580, 664.4665, 642.4832, 536.4991, 518.4912, 500.4803, 264.2681, 184.0738, 166.0624, 124.9993, 104.1069, 86.0960, 60.0802 |
| 484 | SM (d18:1/16:1(OH) | C39 H77 N2 O7 P | 11.78 | 70.10 | 0.51 | 717.5541 | 717.5549 | 699.5538, 264.2683, 184.0737, 166.0629, 124.9994, 104.1069, 86.0962, 60.0803 |
| 485 | SM (d18:2/16:0(OH) | C39 H77 N2 O7 P | 11.31 | 97.55 | −0.48 | 717.5541 | 717.5539 | 699.5407, 640.4669, 534.4876, 516.4743, 262.2538, 184.0737, 166.0641, 124.999, 104.1062, 86.0961, 60.0802 |
| 486 | SM (d19:2/16:0(OH) | C40 H79 N2 O7 P | 11.49 | 96.51 | −1.96 | 731.5698 | 731.5685 | 713.5560, 654.4398, 276.2676, 184.0735, 166.0638, 125.0000, 104.1067, 86.0960, 60.0802 |
| 487 | SM (d19:2/16:1(OH) | C40 H77 N2 O7 P | 11.13 | 94.13 | −2.14 | 729.5541 | 729.5529 | 711.5380, 276.2675, 184.0733, 166.0644, 124.9996, 104.1051, 86.096, 60.0796 |
| 488 | SM (14:1/16:0) | C37 H77 N2 O7 P | 10.81 | 94.52 | −2.35 | 691.5385 | 691.5370 | 673.5273, 206.1906, 184.0735, 124.9995, 104.1063, 86.0959, 60.0802 |
| 489 | SM (16:0/18:0) | C39 H81 N2 O7 P | 12.03 | 91.16 | −2.53 | 721.5854 | 721.5837 | 703.5488, 236.2359, 184.0736, 166.0622, 124.9999, 104.1072, 86.0962, 60.0803 |
| 490 | SM (16:1/20:0) | C41 H83 N2 O7 P | 12.84 | 95.81 | −1.64 | 747.6011 | 747.6000 | 729.5861, 546.5229, 528.5122, 234.2208, 184.0736, 166.0628, 124.9995, 104.1065, 86.0961, 60.0798 |
| 491 | SM (14:0/25:3(OH) | C44 H85 N2 O8 P | 12.19 | 84.67 | −3.81 | 801.6116 | 801.6093 | 208.2070, 184.0735, 166.0651, 124.9983, 104.1072, 86.0961, 60.0798 |
| 492 | SM (16:0/24:3(OH) | C45 H89 N2 O8 P | 13.39 | 87.59 | −1.35 | 815.6273 | 815.6248 | 236.2357, 184.0736, 124.9991, 166.0736, 86.0963 |
| 493 | SM (14:1/23:0(OH) | C42 H85 N2 O8 P | 11.66 | 78.54 | −4.66 | 777.6116 | 777.6087 | 759.5995, 700.4833, 206.1900, 184.0732, 125.0000, 104.1082, 86.0961, 60.0795 |
| 494 | SM (14:1/26:3(OH) | C45 H85 N2 O8 P | 12.88 | 70.53 | −0.29 | 813.6078 | 813.6076 | 795.6000, 206.1902, 184.0735, 166.0601, 104.1063, 86.0961, 60.0805 |
| 495 | SM (14:1/27:3(OH) | C46 H87 N2 O8 P | 12.93 | 86.78 | −3.54 | 827.6273 | 827.6247 | 206.1905, 184.0737, 104.107, 86.0962 |
| 496 | SM (19:1/16:0(OH) | C40 H81 N2 O8 P | 10.21 | 96.77 | −1.45 | 749.5803 | 749.5795 | 731.5680, 672.4165, 294.2838, 276.2673, 184.0735, 166.0634, 124.9992, 104.1068, 86.0962, 60.0802 |
| 497 | SM (18:0/24:1(OH) | C47 H95 N2 O8 P | 15.33 | 91.74 | −2.73 | 847.6899 | 847.6876 | 829.8288, 264.2712, 184.0735, 124.9983, 86.0958, 60.0796 |

TABLE 11-continued

524 SPLs identified including 275 new SPLs (bolded) from wild *Cordyceps* by using UHPLC-UHD iFunnel Q-TOF MS/MS

| No. | Name | Formula | RT | Score | Diff (ppm) | Theoretical [M + H]+ m/z | [M + H]+ m/z | MS/MS fragment m/z |
|---|---|---|---|---|---|---|---|---|
| 498 | SM (d22:0) | C27 H57 N2 O6 P | 8.53 | 75.55 | −2.37 | 537.4027 | 537.4013 | 184.0735, 124.9997, 86.0961, 60.0805 |
| 499 | SM (d30:0) | C35 H73 N2 O6 P | 10.69 | 76.53 | −2.44 | 649.5279 | 649.5259 | 184.0734, 166.0604, 124.9984, 104.1058, 86.0958, 60.0796 |
| 500 | SM (d33:0) | C38 H79 N2 O6 P | 12.04 | 91.46 | −3.11 | 691.5749 | 691.5727 | 184.0735, 125.0000, 104.1074, 86.0967, 60.0801 |
| 501 | SM (d36:0) | C41 H85 N2 O6 P | 13.84 | 96.37 | −1.32 | 733.6218 | 733.6209 | 715.6104, 656.5398, 184.0736, 166.0622, 124.9993, 104.1070, 86.0961, 60.0802 |
| 502 | SM (d37:0) | C42 H87 N2 O6 P | 14.51 | 91.76 | −3.29 | 747.6375 | 747.6349 | 184.0733, 166.0632, 124.999, 104.1070, 86.0963, 60.0802 |
| 503 | SM (d38:0) | C43 H89 N2 O6 P | 15.09 | 92.74 | −2.60 | 761.6531 | 761.6512 | 184.0734, 124.9991, 104.1063, 86.0960, 60.0805 |
| 504 | SM (d40:0) | C45 H93 N2 O6 P | 16.38 | 92.32 | −2.91 | 789.6844 | 789.6821 | 184.0734, 124.9984, 104.1079, 86.0959 |
| 505 | SM (d41:1) | C46 H93 N2 O6 P | 16.44 | 92.84 | −2.65 | 801.6844 | 801.6824 | 783.6700, 184.0732, 104.1085, 86.0960 |
| 506 | SM (d42:1) | C47 H95 N2 O6 P | 17.11 | 93.74 | −2.26 | 815.7001 | 815.6984 | 184.0734, 124.9983, 104.1062, 86.0959, 60.0809 |
| 507 | SM (d44:3) | C49 H95 N2 O6 P | 16.68 | 87.38 | −2.38 | 839.7001 | 839.6974 | 184.0734, 166.0614, 124.9983, 86.0959, 60.0797 |
| 508 | SM (d44:3) Isomer | C49 H95 N2 O6 P | 16.16 | 88.46 | −2.62 | 839.7001 | 839.6974 | 184.0734, 166.0644, 124.999, 104.1050, 86.0962 |
| 509 | SM (d46:3) | C51 H99 N2 O6 P | 17.34 | 92.56 | −2.54 | 867.7314 | 867.7291 | 184.0733, 166.0643, 125.0003, 86.0961, 60.0796 |
| 510 | SM (t23:1) | C28 H57 N2 O7 P | 9.18 | 95.99 | −1.98 | 565.3976 | 565.3964 | 547.2640, 511.2883, 184.0734, 124.9992, 86.0961, 60.0802 |
| 511 | SM (t25:1) | C30 H61 N2 O7 P | 9.85 | 98.03 | −1.29 | 593.4289 | 593.4283 | 575.2683, 184.0734, 124.9995, 86.0960, 60.0799 |
| 512 | SM (t34:2) | C39 H77 N2 O7 P | 10.16 | 75.56 | −2.25 | 717.5541 | 717.5519 | 184.0734, 166.0627, 124.9989, 104.1073, 86.0960, 60.0803 |
| 513 | SM (t38:0) | C43 H89 N2 O7 P | 13.73 | 91.12 | −3.39 | 777.648 | 777.6454 | 759.6285, 184.0733, 166.0643, 124.999, 104.1061, 86.0960, 60.0803 |
| 514 | SM (t40:0) | C45 H93 N2 O7 P | 15.01 | 94.68 | −2.32 | 805.6793 | 805.6775 | 184.0733, 124.9994, 104.1066, 86.096, 60.0797 |
| 515 | SM (t41:0) | C46 H95 N2 O7 P | 15.68 | 88.37 | −3.66 | 819.695 | 819.6921 | 184.0735, 166.0642, 86.0958, 60.0806 |
| 516 | SM (t42:0) | C47 H97 N2 O7 P | 16.34 | 95.05 | −2.57 | 833.7106 | 833.7085 | 815.7026, 756.3451, 184.0734, 166.0643, 125.0099, 104.1083, 86.0968, 60.0798 |
| 517 | SM (q26:2) | C31 H61 N2 O8 P | 8.80 | 95.97 | −1.88 | 621.4238 | 621.4227 | 603.2866, 184.0736, 124.9994, 86.0961, 60.0803 |
| 518 | SM (q27:2) | C32 H63 N2 O8 P | 9.45 | 91.18 | −0.56 | 635.4395 | 635.4385 | 617.4091, 184.0734, 166.0633, 124.9992, 104.1064, 86.0961, 60.0802 |
| 519 | SM (q27:1) | C32 H65 N2 O8 P | 9.63 | 74.89 | −3.54 | 637.4551 | 637.4535 | 184.0735, 124.9983, 104.1066, 86.0957, 60.0814 |
| 520 | SM (q28:2) | C33 H65 N2 O8 P | 9.68 | 96.90 | −1.63 | 649.4551 | 649.4540 | 184.0735, 166.0609, 124.9993, 104.1067, 86.0961, 60.0805 |
| 521 | SM (q29:2) | C34 H67 N2 O8 P | 10.01 | 89.82 | −1.83 | 663.4708 | 663.4691 | 645.4603, 184.0736, 166.0632, 124.9993, 104.1053, 86.0962, 60.0802 |
| 522 | SM (q34:1) | C39 H79 N2 O8 P | 10.28 | 87.26 | −4.22 | 735.5647 | 735.5613 | 184.0735, 124.9999, 104.1061, 86.0963, 60.0797 |
| 523 | SM (q34:1) isomer | C39 H79 N2 O8 P | 10.48 | 93.38 | −2.78 | 735.5647 | 735.5630 | 717.5439, 184.0734, 166.0642, 124.9987, 104.1063, 86.0959, 60.0799 |
| 524 | SM (q41:3) | C46 H89 N2 O8 P | 13.38 | 89.08 | −3.37 | 829.6429 | 829.6404 | 184.0738, 104.1068, 86.0962, 60.0796 |

* 275 SPLs that were bolded in table were identified in this study firstly.

The invention claimed is:
1. A method of treating a subject suffering from inflammation comprising administering an effective amount of at least one sphingolipid portion to the subject, wherein the sphingolipid portion is selected from a sphingoid base portion comprising:
So (d18:5) having the following Formula (3) with x=1 and y=2:

Formula (3)
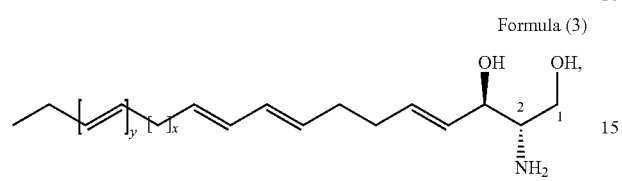

So(d20:3) having Formula (3) as given above with x=7 and y=0,
So(d22:5) having Formula (3) as given above with x=5 and y=2,
So(t15:2) having Formula (4) with x=4 and y=0:

Formula (4)
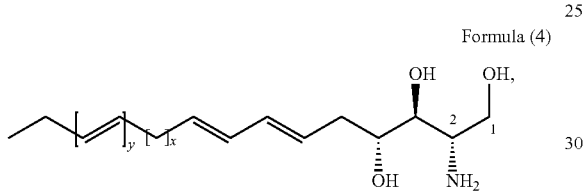

So(t15:3) having Formula (4) as given above with x=2 and y=1,
So(t19:2) having Formula (4) as given above with x=8 and y=0,
So(t21:3) having Formula (4) as given above with x=8 and y=1,
So(t21:4) having Formula (4) as given above with x=6 and y=2,
So(m22:1) having Formula (5) with x=12, y=0 and z=0:

Formula (5)
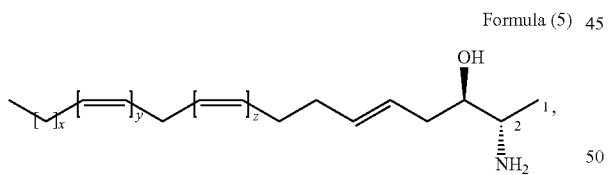

So(m22:2) having Formula (5) as given above with x=10, y=0 and z=1, and So(m22:3) having Formula (5) as given above with x=8, y=1 and z=1 isolated from *Cordyceps* by the method including the steps of:
(i) subjecting a *Cordyceps* material to a solvent extraction with at least a first and a second extracting solvent in order to obtain a sphingolipid crude extract, wherein the first and the second extracting solvent independently comprise an aliphatic alcohol and a halogenated hydrocarbon; and
(ii) subjecting the sphingolipid crude extract to at least a first and a second chromatographic separation step for obtaining the sphingolipid portion, which first chromatographic separation step includes liquid chromatography with a stationary phase comprising an unmodified silica and which second chromatographic separation step includes liquid chromatography with a stationary phase comprising silica modified with polar functional groups, wherein the sphingoid base portion includes a sphinogosine with at least one double bond present in a sphingolipid basic structure.

2. The method of claim 1, wherein the subject is a mammal.

3. A method of treating a subject suffering from inflammation comprising administering an effective amount of sphingoid bases, wherein said sphingoid bases comprise:
So (d18:5) having the following Formula (3) with x=1 and y=2:

Formula (3)
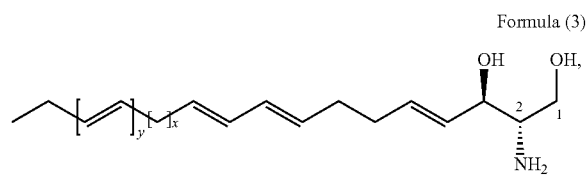

So(d20:3) having Formula (3) as given above with x=7 and y=0,
So(d22:5) having Formula (3) as given above with x=5 and y=2,
So(t15:2) having Formula (4) with x=4 and y=0:

Formula (4)
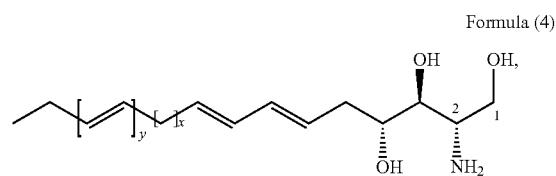

So(t15:3) having Formula (4) as given above with x=2 and y=1,
So(t19:2) having Formula (4) as given above with x=8 and y=0,
So(t21:3) having Formula (4) as given above with x=8 and y=1,
So(t21:4) having Formula (4) as given above with x=6 and y=2,
So(m22:1) having Formula (5) with x=12, y=0 and Z=0:

Formula (5)
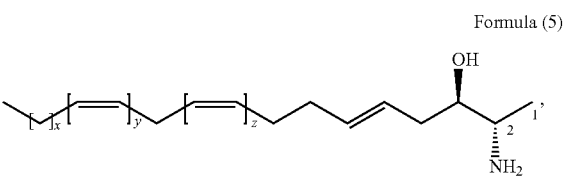

So(m22:2) having Formula (5) as given above with x=10, y=0 and z=1, and
So(m22:3) having Formula (5) as given above with x=8, y=1 and z=1.

4. The method of claim 3, wherein the subject is a human and wherein the concentration of the sphingoid bases is 1 μg/ml to 50 μg/ml.

5. The method of claim 3, wherein the sphingoid bases inhibit proliferation of lymphocytes in the subject.

* * * * *